United States Patent
Xie et al.

(10) Patent No.: US 11,572,382 B2
(45) Date of Patent: Feb. 7, 2023

(54) CAMPTOTHECIN DERIVATIVES AND PREPARATION METHODS AND APPLICATIONS THEREOF

(71) Applicant: TARGET BIOPHARMACEUTICAL TECHNOLOGY SHENZHEN COMPANY LIMITED, Shenzhen (CN)

(72) Inventors: Yongmei Xie, Shenzhen (CN); Xiangrong Song, Shenzhen (CN); Xifei Yang, Shenzhen (CN); Yu Zhao, Shenzhen (CN); Bo Luo, Shenzhen (CN)

(73) Assignee: TARGET BIOPHARMACEUTICAL TECHNOLOGY SHENZHEN COMPANY LIMITED, Shenzhen (CN)

(*) Notice: Subject to any disclaimer, the term of this patent is extended or adjusted under 35 U.S.C. 154(b) by 42 days.

(21) Appl. No.: 17/270,063

(22) PCT Filed: Aug. 15, 2019

(86) PCT No.: PCT/CN2019/100802
§ 371 (c)(1),
(2) Date: Feb. 22, 2021

(87) PCT Pub. No.: WO2020/038278
PCT Pub. Date: Feb. 27, 2020

(65) Prior Publication Data
US 2021/0246157 A1 Aug. 12, 2021

(30) Foreign Application Priority Data
Aug. 21, 2018 (CN) .......................... 201810951933.7

(51) Int. Cl.
C07H 19/056 (2006.01)
C07H 1/06 (2006.01)
C07H 15/26 (2006.01)

(52) U.S. Cl.
CPC ............. *C07H 19/056* (2013.01); *C07H 1/06* (2013.01); *C07H 15/26* (2013.01)

(58) Field of Classification Search
None
See application file for complete search history.

(56) References Cited

FOREIGN PATENT DOCUMENTS

| | | |
|---|---|---|
| CN | 104837508 A | 8/2015 |
| WO | 2007052308 A2 | 5/2007 |
| WO | 2011002852 A2 | 1/2011 |
| WO | 2015012904 A2 | 1/2015 |
| WO | 2016025129 A1 | 2/2016 |
| WO | 2009100194 A2 | 8/2019 |

OTHER PUBLICATIONS

Santi, et al., Macromolecular Prodrug that Provides the Irinotecan (CPT-11) Active-Metabolite Sn-38 with Ultralong Half-Life, Low C (Max), and Low Glucuronide Formation, Journal of Medicinal Chemistry, Mar. 27, 2014, 2303-2314, 57(6), ACS, Washington, D.C., U.S.A.
Tyle, et al., Lontophoretic Devices for Drug Delivery, Pharmaceutical Research, Dec. 1986, 318-326, vol. 3(6), Springer Nature, AG, Switzerland.
Angenault et al., Antibody Conjugates of 7-Ethyl-10-hydroxycamptothecin (SN-38) for Targeted Cancer Chemotherapy, J. Med. Chem., No. 51, Oct. 22, 2008, ISSN: 0960-894X, 6916.
Govindan et al., Improving the Therapeutic Index in Cancer Therapy by Using Antibody-Drug Conjugates Designed with a Moderately Cytotoxic Drug, J. Med. Chem. (Anti-Drug Conjugates), No. 12, Nov. 2014, 1836-1847.

*Primary Examiner* — Layla D Berry

(57) ABSTRACT

The invention relates to novel camptothecin derivatives and their applications, tumor cell growth inhibitors, ternary complexes, and a method for improving the solubility of the camptothecin derivatives. The camptothecin derivatives are prepared by modifying the substance shown as Formula I with glycosylated triazole at position $R^3$. In the structure shown as Formula I, $R^1$ represents H, $C_{1-10}$ alkyl, $C_{1-10}$ alkyl-D or $C_{1-10}$ haloalkyl; $R^2$ represents H, $CH_2N(CH_3)_2$ or $CH_2N(CD_3)_2$; and $R^4$ represents

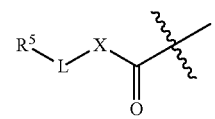

or H, wherein X represents N, O or S; and L represents polypeptide, $C_{1-20}$ linear alkyl or derivatives thereof, $C_{1-20}$ linear or branched acyl derivatives, $C_{2-100}$ ethylene glycol or derivatives thereof. The camptothecin derivatives have high solubility, the anticancer drugs prepared from them have the advantages of wide anticancer spectrum and high safety, and have in vivo anticancer activity higher than irinotecan hydrochloride.

13 Claims, 5 Drawing Sheets

CAMPTOTHECIN DERIVATIVES AND PREPARATION METHODS AND APPLICATIONS THEREOF

RELATED APPLICATIONS

The application is a national phase application of the International Application PCT/CN2019/100802 filed Aug. 15, 2019, which claims the benefit of the Chinese Patent Application CN201810951933.7 filed Aug. 21, 2018, each of which is incorporated herein by reference in its entirety.

FIELD OF THE INVENTION

The invention relates to novel camptothecin derivatives and their applications, tumor cell growth inhibitors, ternary complexes, and a method for improving the solubility of the camptothecin derivatives. The camptothecin derivatives can be used for preparing antitumor drugs.

BACKGROUND OF THE INVENTION

Camptothecin (CPT) is a quinoline-containing alkaloid first extracted from barks and fruits of *Camptotheca acuminata* (Nyssaceae) in China by American chemists Wall et al. in 1966. Early studies found that CPT had antitumor activity, but the poor solubility of CPT in water greatly reduced its clinical application value. Later, scientists increased its water solubility by hydrolyzing the ester ring in its molecule through salt-forming method, while its antitumor activity decreased. In addition, CPT itself has strong side effects, such as hemorrhagic cystitis, severe bone marrow suppression, etc. Because of these defects, scientists had to stop clinical studies of CPT in the 1970s. The discovery by Hsiang et al. in 1985 that CPT is a proprietary inhibitor of topoisomerase I (ToPoI) reinvigorated the study of CPT. On the basis of study of its pharmacological mechanism and study on structure-activity relationship, a series of camptothecin derivatives have been developed by researchers. Irinotecan hydrochloride (CPT-11) is a water-soluble camptothecin derivative commonly used in clinical treatment of colorectal cancer, lung cancer, breast cancer, etc. But it has low antitumor activity and high side effects. Development of various camptothecin derivatives and improvement on their medicinal properties are a challenge in development of antitumor drugs.

Topotecan, belotecan, 10-hydroxycamptothecin and other camptothecin derivatives have been developed and applied in human body, but compatibility between these derivatives and human body has always been a major challenge in pharmaceutical industry. For example, as metabolite of irinotecan, SN-38 has in vitro antitumor activity 100-1000 times of that of irinotecan, however it has poor solubility and is almost insoluble in common drug solvents and water, so that it has poor druggability (Santi et al., J Med Chem. 2014, 57(6): 2303-2314) and has great limitation in clinical application.

OBJECTS AND SUMMARY OF THE INVENTION

In view of this, it is one object of the invention to provide a camptothecin derivative with high water solubility.

In order to realize it, the invention adopts the following scheme:

The camptothecin derivative is prepared by modifying the substance shown as Formula I with glycosylated triazole at position $R^3$. In the structure shown as Formula I, $R^1$ represents H, $C_{1-10}$ alkyl, $C_{1-10}$ alkyl-D or $C_{1-10}$ haloalkyl; $R^2$ represents H, $CH_2N(CH_3)_2$ or $CH_2N(CD_3)_2$; and $R^4$ represents

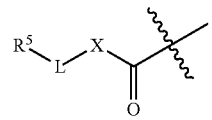

or H, wherein X represents N, O or S, and L represents polypeptide, $C_{1-20}$ linear alkyl or derivatives thereof, $C_{1-20}$ linear or branched acyl derivatives, $C_{2-100}$ ethylene glycol or derivatives thereof.

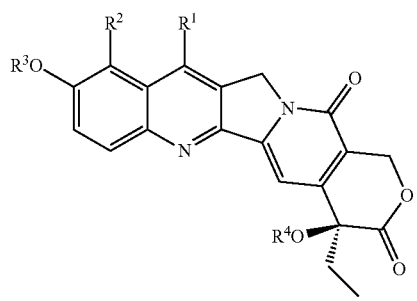

Further, in the Formula I, $R^3$ represents

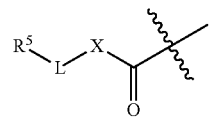

or H, $R^4$ represents

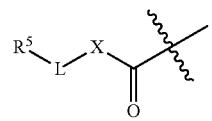

or H, while $R^3$ and $R^4$ are not H simultaneously; $R^5$ represents monoglycosyl residue or oligosaccharyl residue; and L represents polypeptide, $C_1$-$C_{20}$ linear alkyl or derivatives thereof, $C_1$-$C_{20}$ linear or branched acyl derivatives, $C_1$-$C_{20}$ ethylene glycol or derivatives thereof,

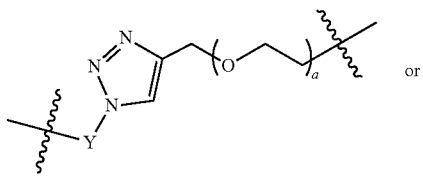

or

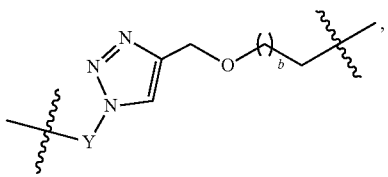

wherein Y is

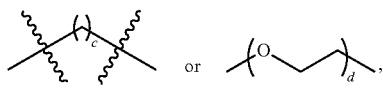

a is an integer of 0-100, b is an integer of 1-100, c is an integer of 0-100, and d is an integer of 0-100.

Further, in the Formula I, $R^1$ represents H or —$CH_2CH_3$; $R^2$ represents H, —$CH_2N(CH_3)_2$ or —$CH_2N(CD_3)_2$; $R^3$ represents

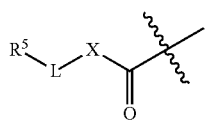

or H, $R^4$ represents

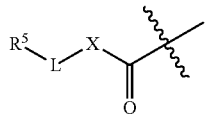

or H, while $R^3$ and $R^4$ are not H simultaneously; $R^5$ is selected from monoglycosyl residue or oligosaccharyl residue; X is selected from N or κ; and L is selected from $C_{1-20}$ linear or branched alkane and derivatives thereof, $C_{1-20}$ linear or branched acyl derivatives, $C_{2-100}$ ethylene glycol or derivatives thereof,

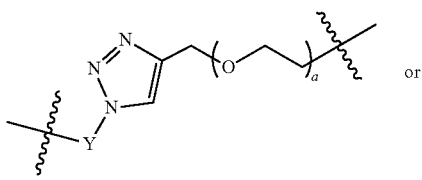

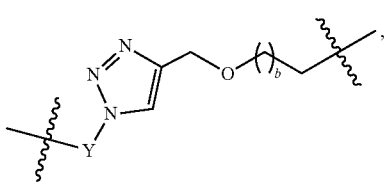

wherein Y is

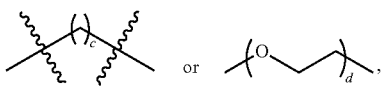

a is an integer of 0-100, b is an integer of 1-100, c is an integer of 0-100, and d is an integer of 0-100.

Further, a is 0, 2, 4, 6, 8, 10, 12, 14, 16, 18, 20, 30, 40, 50, 60, 70, 80, 90, 100.

Further b is 1, 2, 4, 6, 8, 10, 12, 14, 16, 18, 20, 30, 40, 50, 60, 70, 80, 90, 100.

Further, c is 0, 2, 4, 6, 8, 10, 12, 14, 16, 18, 20, 30, 40, 50, 60, 70, 80, 90, 100.

Further, d is 0, 2, 4, 6, 8, 10, 12, 14, 16, 18, 20, 30, 40, 50, 60, 70, 80, 90, 100.

Further, $R^1$ represents —$CH_2CH_3$; $R^2$ represents H; $R^3$ represents

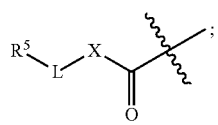

$R^4$ represents H; X represents N or O; and L represents

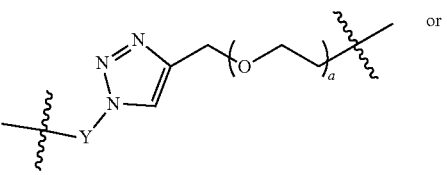

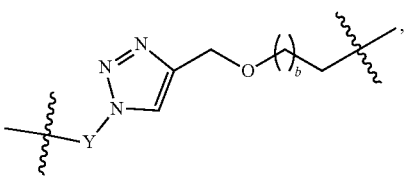

wherein Y is

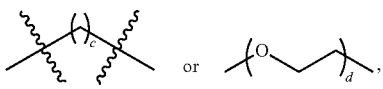

a is an integer of 1-20, b is an integer of 1-20, c is an integer of 0-20, and d is an integer of 0-20.

Further, the camptothecin derivative is 7-ethyl-10-hydroxycamptothecin derivative with structure shown as Formula II.

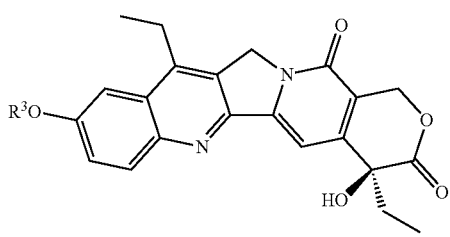
II
Further, the glycosylated triazole has structure shown as Formula III or IV, wherein Y is
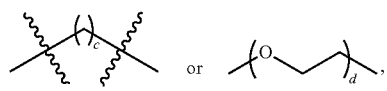
a is an integer of 0-100, b is an integer of 1-100, c is an integer of 0-100, d is an integer of 0-100, and $R^5$ is glycosyl residue or oligosaccharyl residue.
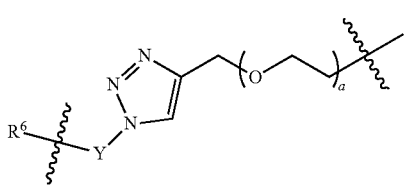
III
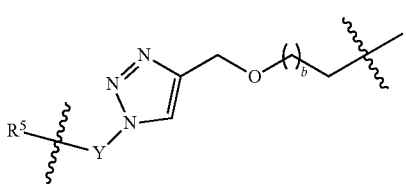
IV
Further, $R^5$ is selected from anyone of monoglycosyl residues shown as Formulas 5-28.
5
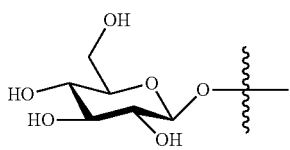
6
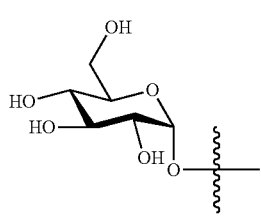
7
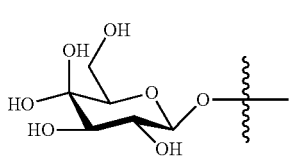
8
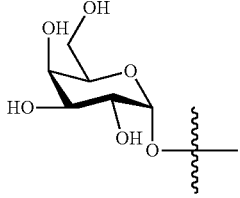
9
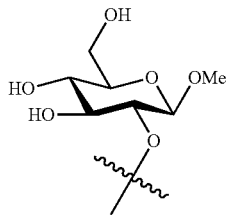
10
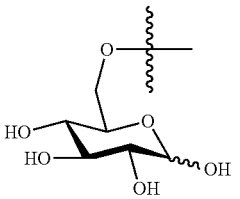
11
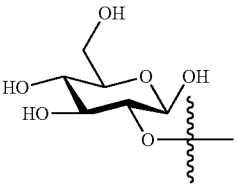
12
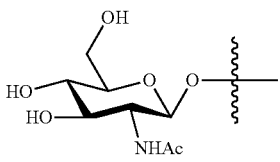
13
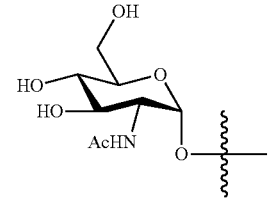
14
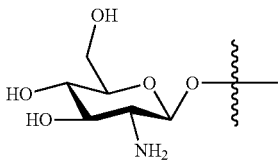
15
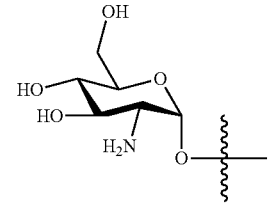

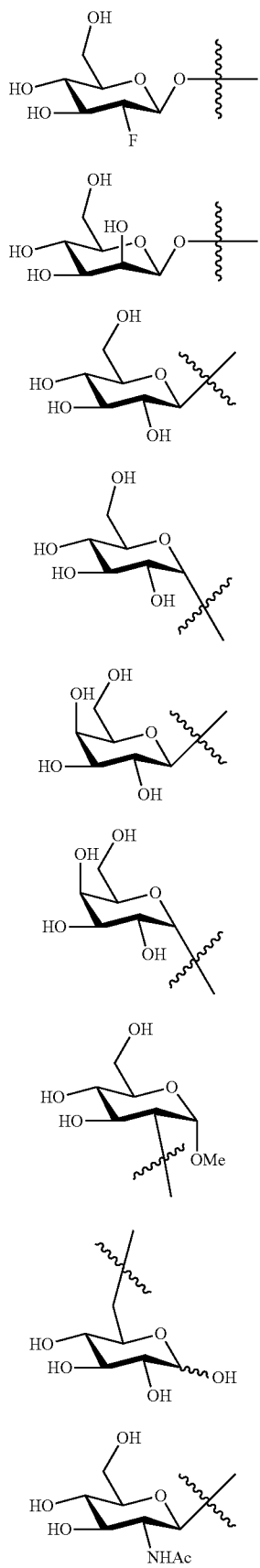
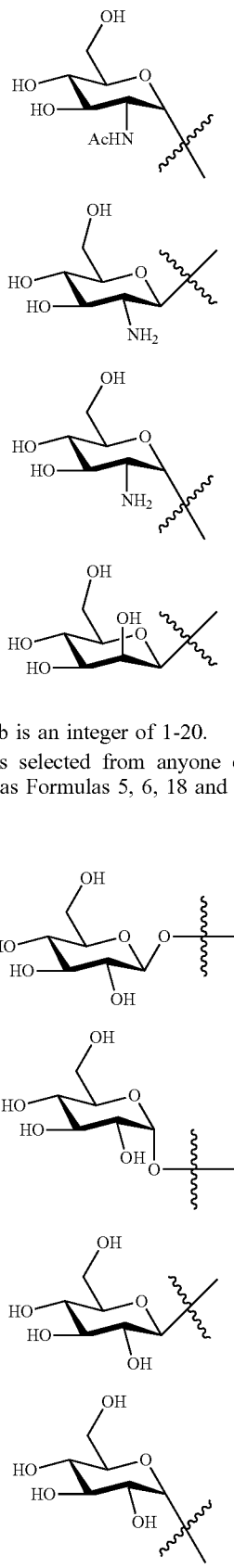
Further, a or b is an integer of 1-20.
Further, $R^5$ is selected from anyone of monoglycosyl residues shown as Formulas 5, 6, 18 and 19.

Further, the derivative is one of the following compounds:
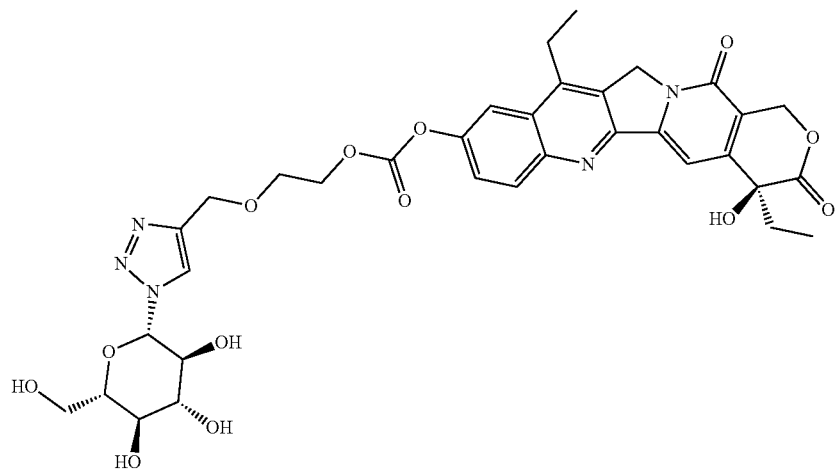
37
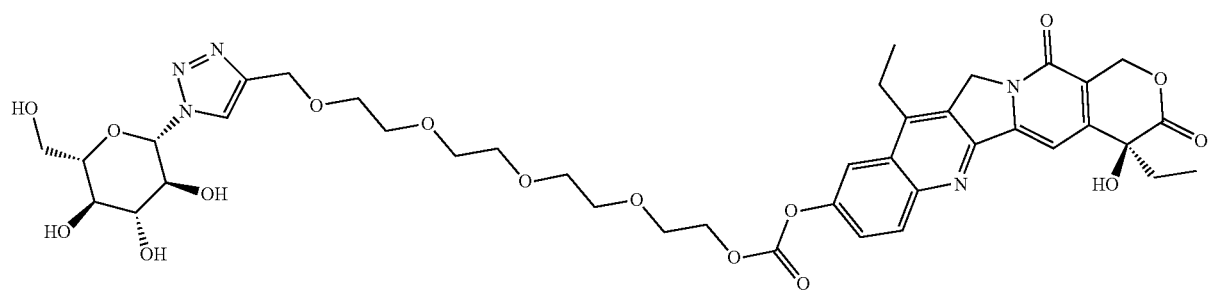
42
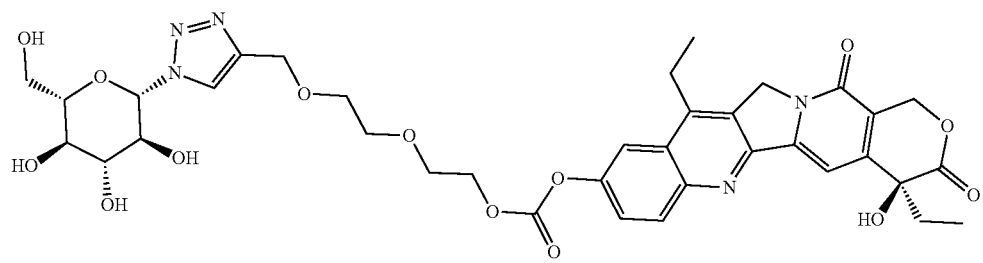
47
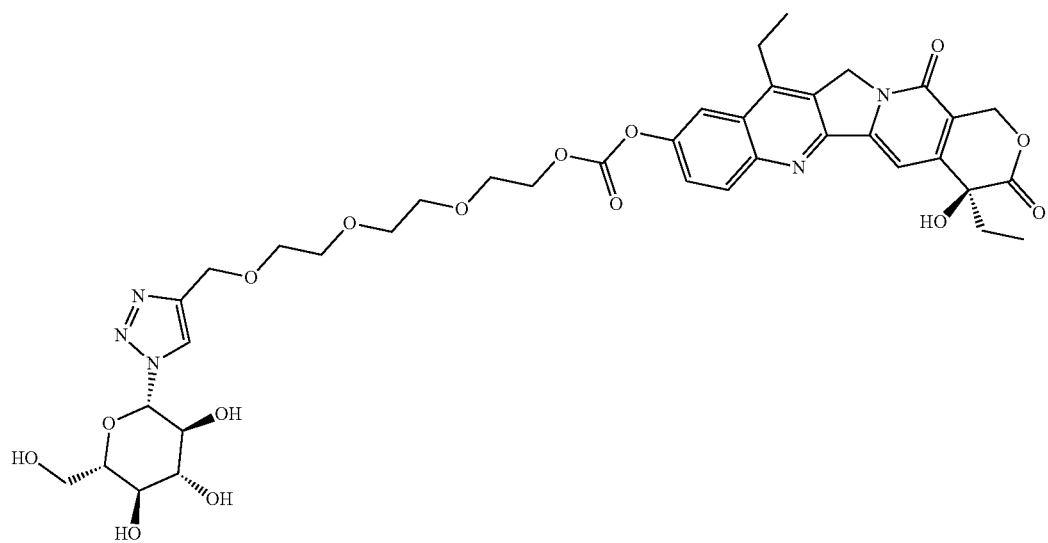
52

56
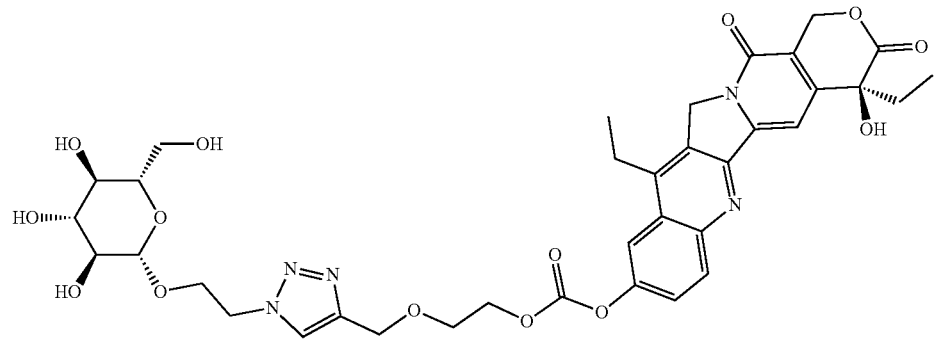
57
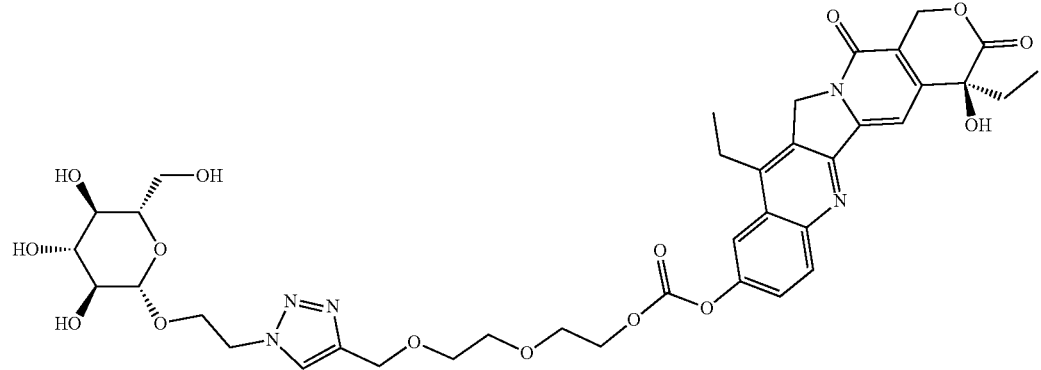
58
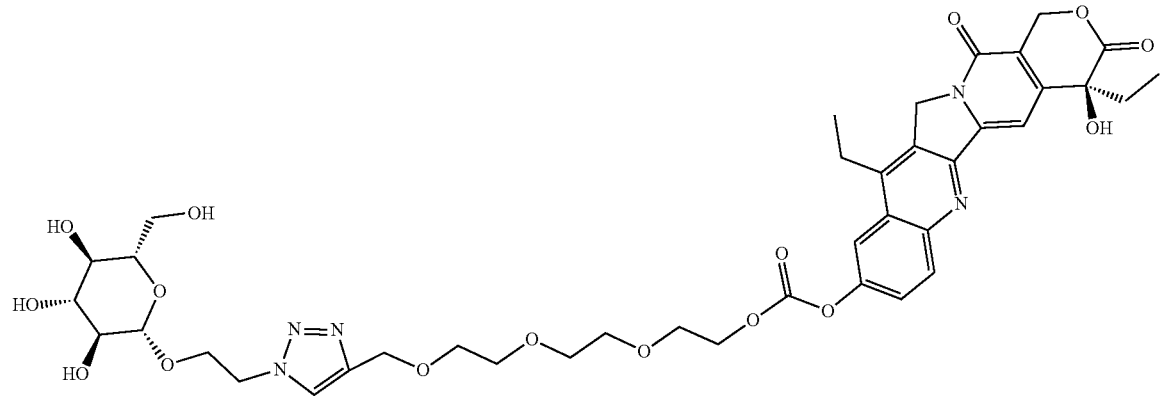
59
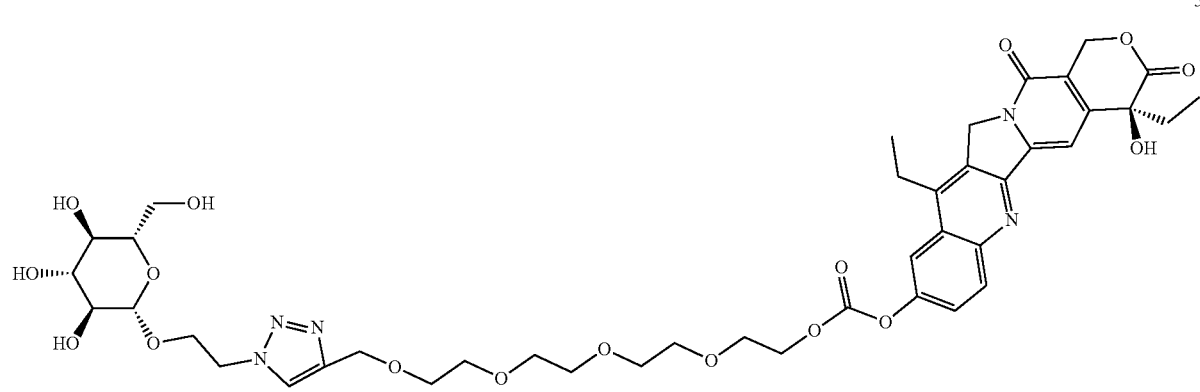

-continued
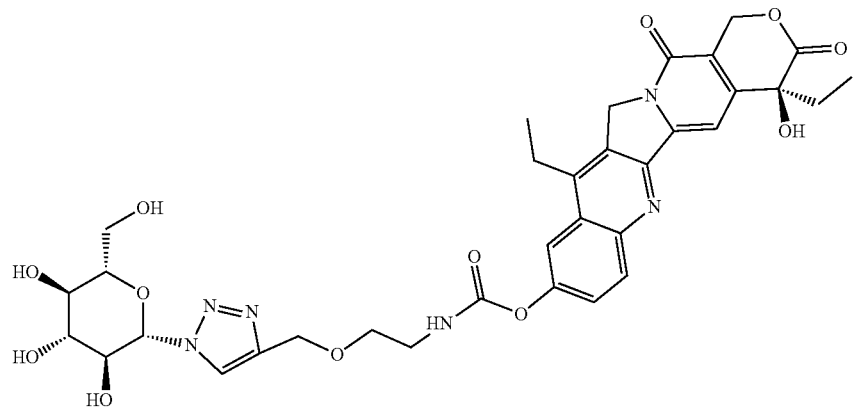
66
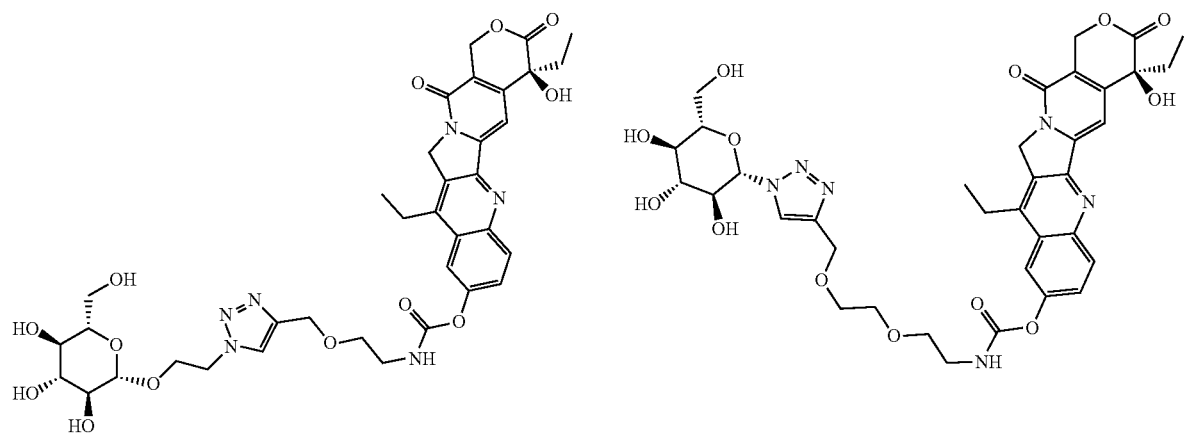
67
73
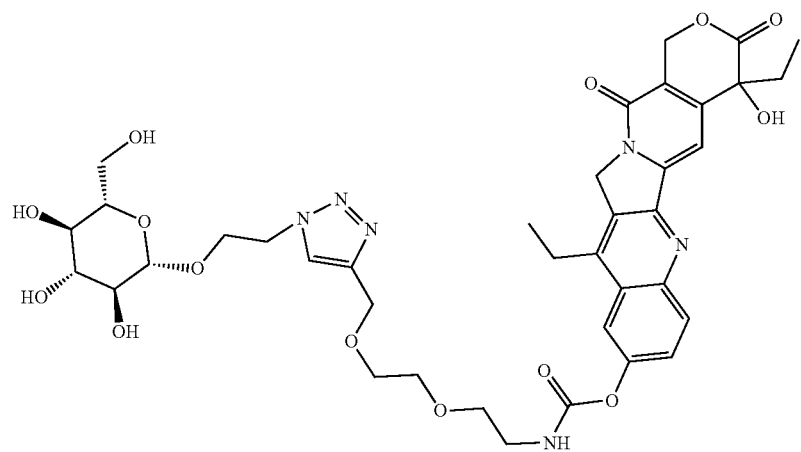
74

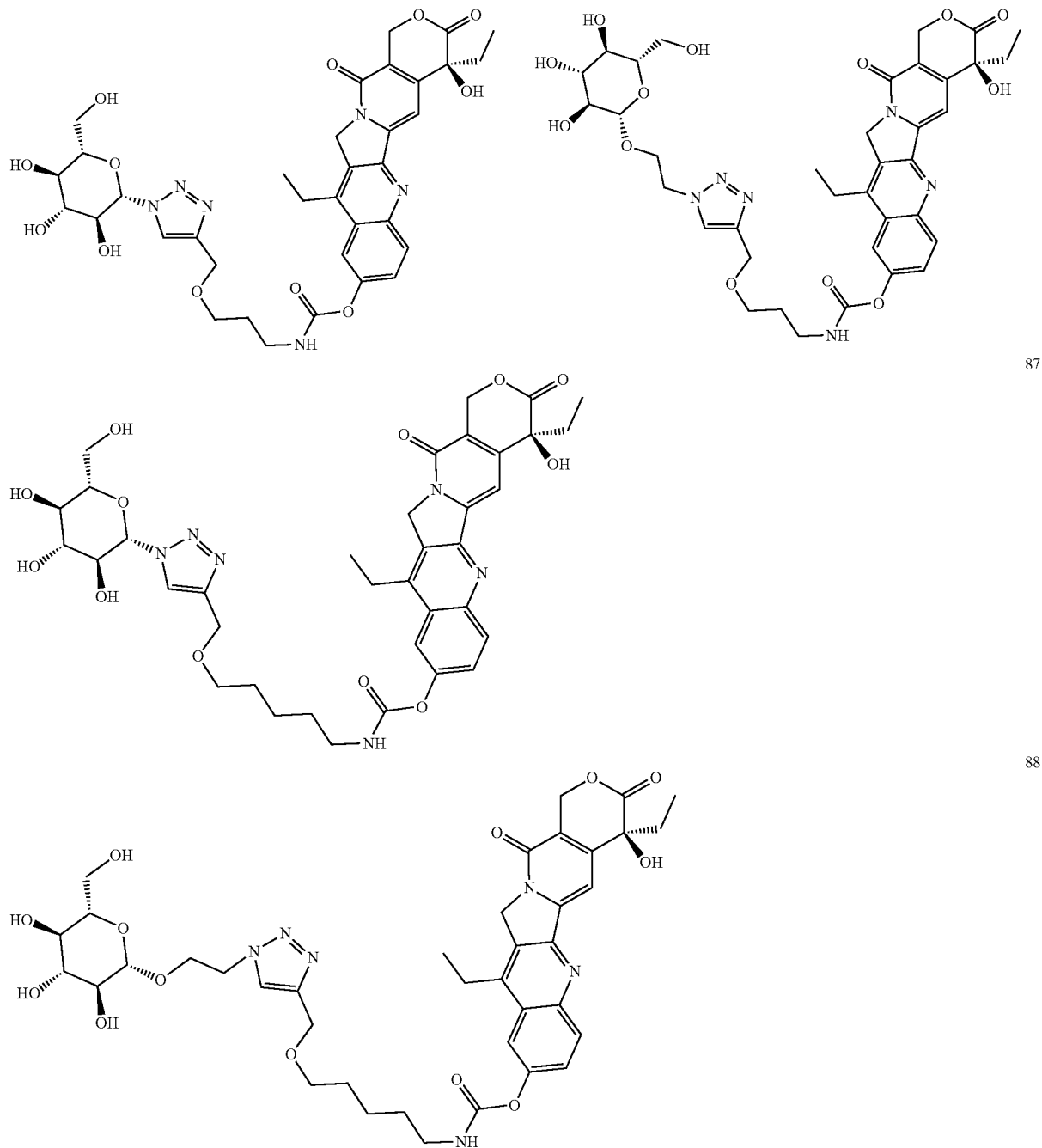

Further, X is selected from N or O.
Further, Y is

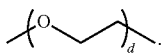

Further, d is an integer of 0-1.
Further, a is 1, and b is an integer of 1-4.

It is a second object of the invention to provide a method for synthesizing the camptothecin derivative, which can be applied in industrial production.

In order to realize it, the invention adopts the following scheme:

The method includes the following steps:
1) Synthesizing azide compound by chemical reaction;
2) Synthesizing terminated alkyne by chemical reaction; and
3) Dissolving the azide compound and the terminated alkyne in THF-H₂O, adding anhydrous copper sulfate and sodium ascorbate in sequence for click reaction, stirring at room temperature overnight, concentrating, and separating by column chromatography to obtain the camptothecin derivative.

The azide compound is

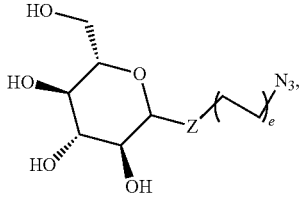

wherein Z is none or O, and e is 0-20.

Preferably, Z is none or O, and e is 0-1.

It is a third object of the invention to provide a method for improving solubility of camptothecin derivatives, which is suitable for industrial application.

In order to realize it, the invention adopts the following scheme:

The method includes modifying 7-ethyl-10-hydroxycamptothecin derivatives, which have structure shown as Formula II, with glycosylated triazole at position $R^3$. In the structure shown as Formula II, $R^3$ represents

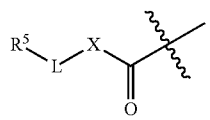

or H, wherein X represents N, O or S; L represents polypeptide, $C_1$-$C_{20}$ linear alkyl or derivatives thereof, $C_1$-$C_{20}$ linear or branched acyl derivatives. $C_1$-$C_{20}$ ethylene glycol or derivatives thereof,

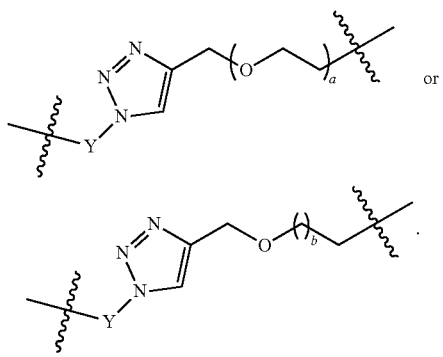

Further, the glycosylated triazole has structure shown as Formula III or IV, wherein Y is

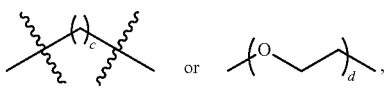

a is an integer of 0-100, b is an integer of 1-100, c is an integer of 0-100, d is an integer of 0-100, and $R^5$ is glycosyl residue or oligosaccharyl residue.

Further, $R^5$ has structure shown as anyone of Formulas 5-28.

Further, $R^5$ is selected from anyone of monoglycosyl residues shown as Formulas 5, 6, 18 and 19.

Further, a is 1, and b is an integer of 1-4.

Further, Y is

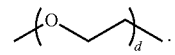

Further, d is an integer of 0-1.

It is a fourth object of the invention to provide a tumor cell growth inhibitor, which has anticancer effect.

In order to realize it, the invention adopts the following scheme:

A tumor cell growth inhibitor is prepared from the camptothecin derivative.

The camptothecin derivative can comprise any pharmaceutically acceptable carrier and/or adjuvant.

Further, the tumor cell growth inhibitor can break DNA chain by forming ternary complex with topoisomerase I and DNA, inhibit the growth of tumor and promote tumor cell apoptosis.

Further, the tumor is colorectal tumor, lung tumor, breast cancer, liver cancer, gastric cancer, esophageal carcinoma, leukemia, prostatic cancer, osteosarcoma, cervical cancer, thyroid cancer, ovarian cancer or pancreatic cancer.

It is a fifth object of the invention to provide a ternary complex capable of inhibiting growth of tumor cells.

In order to realize it, the invention adopts the following scheme:

The ternary complex is formed from the tumor cell growth inhibitor, topoisomerase I and DNA. The ternary complex breaks DNA chain, inhibits the growth of tumor and promotes tumor cell apoptosis.

It is a sixth object of the invention to provide an application of the camptothecin derivative, which provides a new idea for cancer treatment.

In order to realize it, the invention adopts the following scheme:

An application of the camptothecin derivative in preparation of anticancer drugs is provided.

Further, the cancer is colorectal cancer, lung cancer, breast cancer, liver cancer, gastric cancer, esophageal cancer, leukemia, prostatic cancer, osteosarcoma, cervical cancer, thyroid cancer, ovarian cancer or pancreatic cancer.

Further, the anticancer drugs can break DNA chain by forming ternary complex with topoisomerase I and DNA, inhibit the growth of tumor and promote tumor cell apoptosis so as to achieve anticancer effect, and the tumor cells are SW-480 and/or HT-29 and/or HCT-116 and/or A549 and/or H1975 and/or HepG2 and/or BGC-823 and/or ECA-109 and/or K562 and/or PC3 and/or 143B and/or MDA-MB-231 and/or Hela and/or TPC-1 and/or SKOV-3 and/or PANC-1.

It is a seventh object of the invention to provide a preparation, which can effectively inhibit growth of tumor cells.

In order to realize it, the invention adopts the following scheme:

The preparation is prepared from the camptothecin derivative.

Further, the preparation comprises pharmaceutically acceptable carriers and/or adjuvants.

The pharmaceutically acceptable preparation includes traditional Chinese medicine composition of the invention and optional one or more pharmaceutically acceptable carriers, diluents or excipients added at an appropriate step in the preparation process. The term "pharmaceutically acceptable" used in the invention refers to such compounds, raw materials, compositions and/or preparations that they are suitable for contact with the patient tissues without excessive toxicity, irritation, allergic effect or other problems and complications relative to reasonable benefit/risk ratio in a range of reasonable judgment of medicine and are effective in intended application.

Pharmaceutical preparations are suitable for being administrated through any appropriate route, such as oral (including oral cavity or sublingual), rectal, nasal, topical (including oral cavity, sublingual or percutaneous), vaginal or parenteral (including subcutaneous, intradermal, intramuscular, intra-articular, intrasynovial, intrasternal, intrathecal, intralesional, intravenous or dermal injection or infusion) administration route. Such preparations can be prepared by any known method in the field of pharmacy, for example by mixing an active ingredient with carriers or excipients. Oral administration, topical administration or injection administration is preferable. Pharmaceutical preparations suitable for oral administration are provided in separated units, such as solution or suspension in aqueous or non-aqueous liquids, capsule or tablet, powder or granule, and edible foam preparation or foaming preparation, etc.

For example, for oral administration in tablet or capsule form, an active drug ingredient can be mixed with a pharmaceutically acceptable oral non-toxic inert carrier (such as ethanol, glycerol, water, etc.). Powder can be prepared by pulverizing compound into suitable fine size and mixing with similarly pulverized medicinal carrier (edible sugar such as starch or mannitol). Corrigent, preservative, dispersant and colorant can also be present. Capsule can be prepared by filling the prepared powder mixture into a formed gelatin shell. Flow aid and lubricant (such as colloidal silica, talcum powder, magnesium stearate, calcium stearate or solid polyethylene glycol) can be added to the powder mixture before the filling operation. Disintegrant or solubilizer (such as agar, calcium carbonate or sodium carbonate) capable of improving drug availability when the capsule is administrated can also be added.

In addition, appropriate binder, lubricant, disintegrant and colorant can be added to the mixture when required or necessary. The appropriate binder includes starch, gelatin, natural sugar (such as glucose or β-lactose), corn sweetener, natural and synthetic gums (such as Arabic gum, tragacanth gum or sodium alginate), carboxymethyl cellulose, polyethylene glycol, etc. The lubricant includes sodium oleate, sodium chloride, etc.

The disintegrant includes, but is not limited to, starch, methylcellulose, agar, bentonite, xanthan gum, etc. For example, tablet is prepared by preparing powder mixture, granulating or pre-tabletting, adding lubricant and disintegrant, and pressing. The powder mixture is prepared by mixing appropriately pulverized compound with the above diluent or base material and optionally binder (such as carboxymethyl cellulose, alginate, gelatin or polyvinylpyrrolidone), dissolution inhibitor (such as paraffin), absorption accelerator (quaternary salt) and/or absorber (such as bentonite, kaolin and calcium dihydrogen phosphate). The powder mixture can be granulated after wetting with binder (such as syrup, starch slurry, Arabic gum or solution of cellulose or polymer material) and sieving under pressure. An alternative method of granulation is to pass the powder mixture through a tablet press, pulverize resulting unsatisfactory clumps and prepare into granule. The granules can be lubricated by adding stearic acid, stearate, talcum powder or mineral oil to prevent adhesion to the die of the tablet press. The lubricated mixture is then pressed into tablets. The compound of the invention can also be mixed with a free-flowing inert carrier and can be pressed into tablets without granulating or pre-tabletting step. A transparent or non-transparent protective coating material consisting of shellac seal coating, sugar coating or polymer material coating and wax polishing coating can be provided. Dye can be added to the coating materials to distinguish different unit doses.

Oral liquid preparations, such as solutions, syrups and elixirs, can be prepared in dose unit form to contain a predetermined amount of the compound. Syrup can be prepared by dissolving the compound in a suitably flavored aqueous solution, and elixir can be prepared by using a non-toxic solvent. Preservative and corrigent additive (such as peppermint oil or natural sweetener or saccharin or other artificial sweeteners) can also be added.

Pharmaceutical preparations suitable for transdermal administration can be used as discrete patches to maintain close contact with epidermis of recipient for a long time, for example, active ingredient can be delivered by an iontophoresis patch, usually referring to Pharmaceutical Research, 1986, 3(6), 318.

Pharmaceutical preparations suitable for topical administration can be prepared into ointment, cream, suspension, lotion, powder, solution, paste, gel, spray, aerosol, oil preparation or transdermal patch. Pharmaceutical preparations suitable for nasal administration (wherein the carrier is solid) include coarse powders with particle size of, for example, 20-500 microns, and are administrated by nasal aspiration, i.e., rapid inhalation through nasal passage from a coarse powder container close to the nose. Wherein appropriate preparations with liquid as carrier and suitable for nasal spray or nasal drop administration include aqueous solution or oil solution of active ingredient.

Pharmaceutical preparations suitable for inhalation administration include fine powder or fine spray, and can be prepared in differently-metered dose compressed aerosol, aerosol inhaler, insufflator or other devices suitable for delivery of aerosol spray. Pharmaceutical preparations suitable for parenteral administration include aqueous and non-aqueous aseptic injection solutions and aqueous and non-aqueous aseptic suspensions, and the aqueous and non-aqueous aseptic suspensions can contain antioxidant, buffer agent, bacteriostatic agent, and solute making the preparations and bloods of the intended recipients isotonic. The preparations can be provided in unit-dose or multi-dose containers, such as sealed ampules and vials, and can be preserved in freeze-drying (lyophilization) condition, and sterile liquid carrier such as water for injection is added before use. The injection solution prepared before use can be prepared from sterile powder for injection, granule and tablet.

Pharmaceutical preparations can be in unit dose form, each unit dose containing a predetermined amount of the active ingredient. The administration method can be used as long-term or short-term therapy. The amount of the active ingredient for preparing a single preparation by mixing carrier material changes according to to-be-treated disease, severity degree of disease, administration time, administration route, excretion rate of the used compound, treatment time and patient age, sex, weight and condition. The preferred unit preparation is the unit preparation containing daily dose or fractional dose or appropriate fraction of the active ingredient. A small dose clearly smaller than the optimal dose of compound is used at beginning of treatment, and then the dose is increased in small increment until the best effect is achieved in this case. In general, compounds are ideally administered at concentrations where usually effective antiviral result is provided without causing any harmful or toxic side effect.

The invention has the beneficial effects as following:
1) The invention provides a novel camptothecin derivative with solubility significantly higher than that of SN38;
2) The tumor cell growth inhibitor and the prepared anticancer drug of the invention have wide anticancer spectrum, and have anticancer activity higher than that of irinotecan hydrochloride; and
3) The tumor cell growth inhibitor and the prepared anticancer drug have high safety, and have no obvious side effect when used at high dose.

DETAILED DESCRIPTION OF THE EMBODIMENTS

Figure 1:
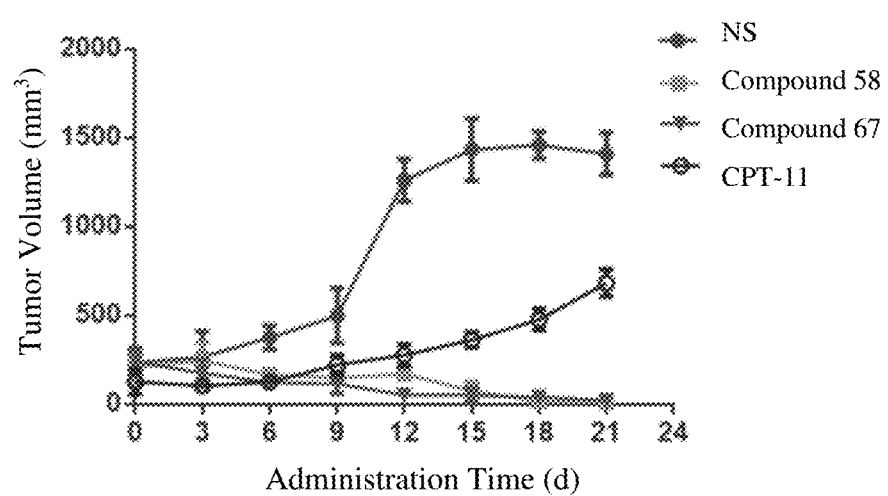
FIG. 1: Nude mouse tumor volume-time variation diagram.

The invention is further described below by specific embodiments, but it is to be understood that these embodiments are only for more detailed description and is not to be understood as limiting the invention in any way.

The invention gives general and specific descriptions of the materials used in the test and the experimental methods. Although many of the used materials and operation methods for realizing the purpose of the invention are known in the art, the invention describes herein as detailed as possible. Those skilled in the art should understand that, unless otherwise specified below, the used materials and operation methods hereinafter are known in the art.

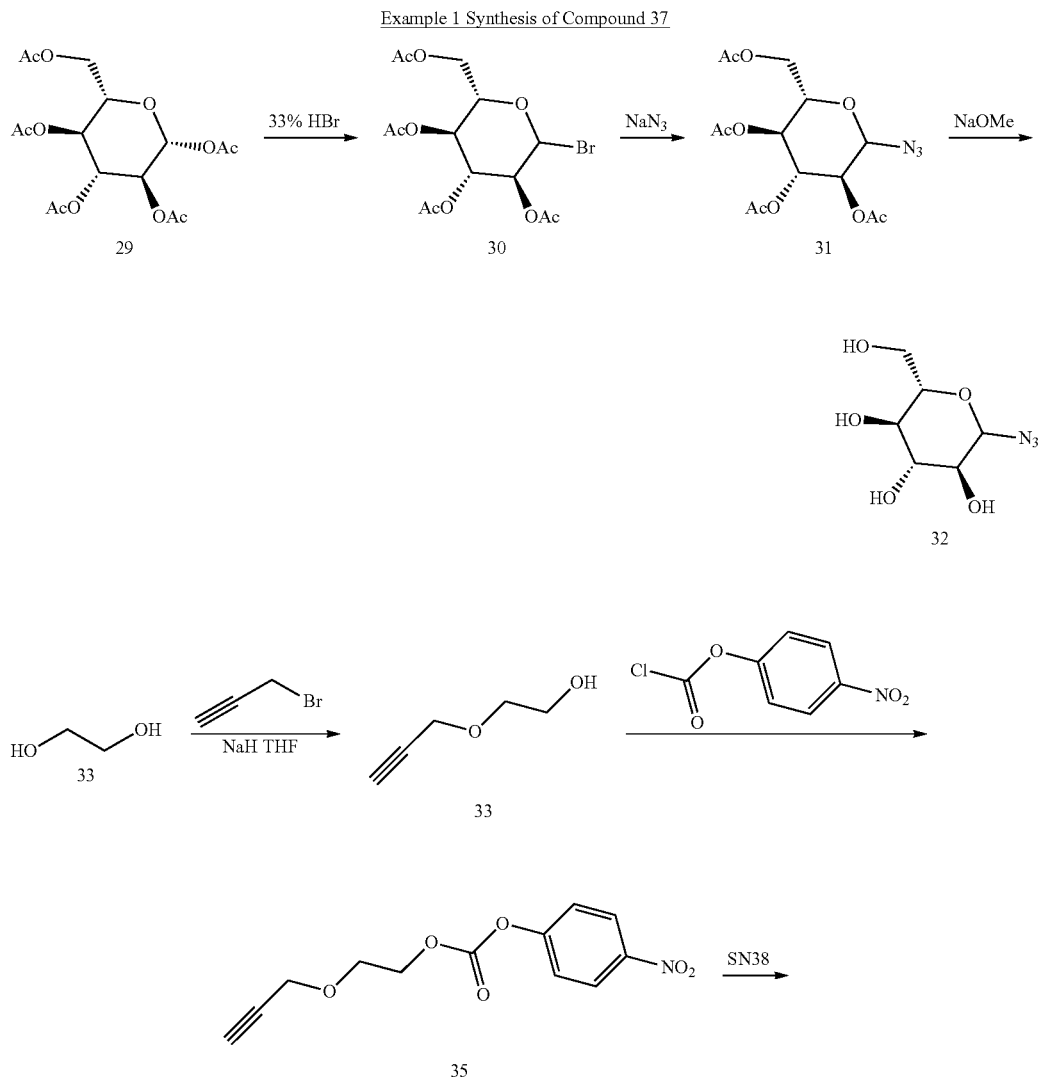

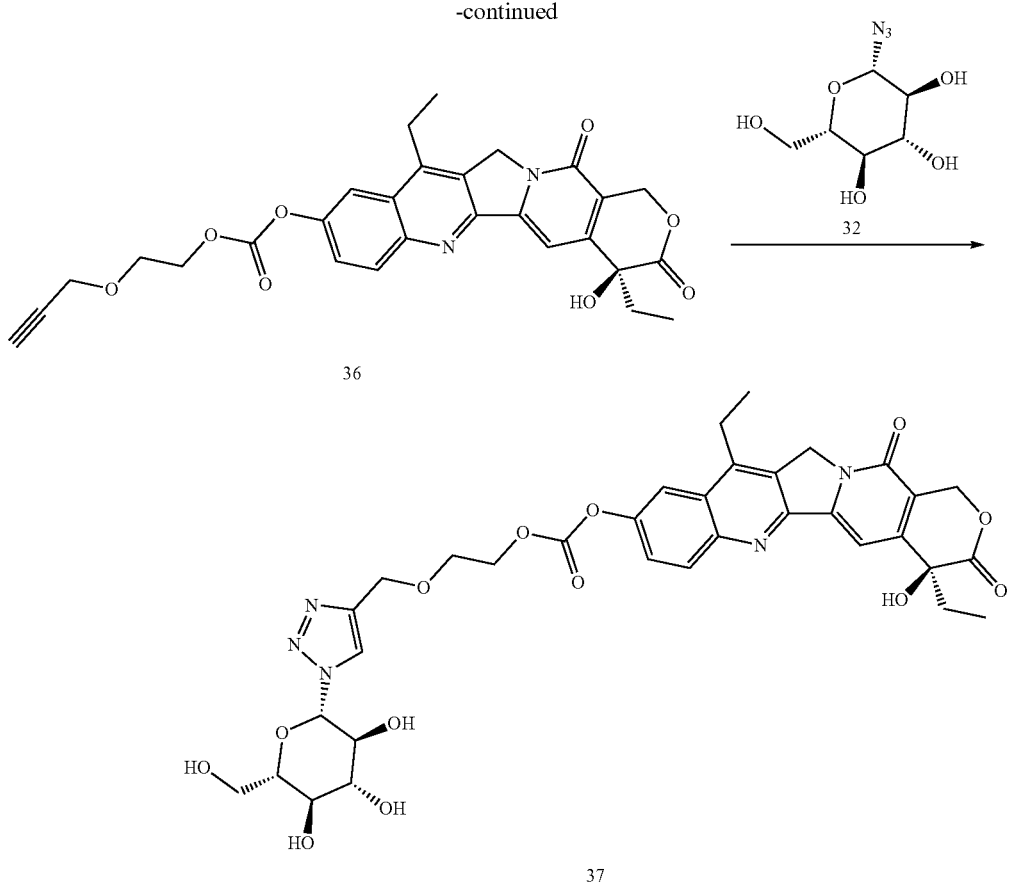

Weighing 9 g of compound 29, dissolving in 60 mL of dichloromethane, adding 25 mL of 33% acetic acid solution of hydrobromic acid, reacting at room temperature for 2 h while monitoring complete reaction by TLC, pouring into 50 mL of water, extracting with dichloromethane (50 mL×3), combining organic layers, washing with saturated sodium bicarbonate for one time, drying with anhydrous sodium sulfate, filtering, concentrating, and recrystallizing with mixed solvent of petroleum ether/ethyl acetate at 10/1 to obtain 8.2 g of compound 30 with yield of 86.7%. The structure of the compound is identified by hydrogen nuclear magnetic resonance spectroscopy.

$^1$H NMR (400 Hz, CDCl$_3$) δ 6.61 (d, J=4.4 Hz, 1H), 5.56 (t, J=9.6 Hz, 1H), 5.16 (t, J=9.8 Hz, 1H), 4.84 (dd, J=10.0, 4.0 Hz, 1H), 4.28-4.35 (m, 2H), 4.12-4.15 (m, 1H), 2.10 (s, 3H), 2.09 (s, 3H), 2.05 (s, 3H), 2.04 (s, 3H).

Dissolving 8.2 g of the compound 30 in 40 mL of DMSO, adding 1.56 g of sodium azide, stirring at room temperature for 1 h while monitoring complete reaction by TLC, pouring into 100 mL of water, extracting with ethyl acetate (50 mL×3), combining organic layers, dying with anhydrous sodium sulfate, filtering, concentrating, and recrystallizing with mixed solvent of petroleum ether/ethyl acetate at 10/1 to obtain 5.8 g of compound 31 with yield of 77.7%.

$^1$H NMR (400 Hz, CDCl$_3$) δ 5.22 (t, J=9.4 Hz, 1H), 5.11 (t, J=9.6 Hz, 1H), 4.96 (t, J=9.2 Hz, 1H), 4.65 (d, J=8.8 Hz, 1H), 4.26-4.30 (m, 2H), 4.16-4.19 (m, 1H), 3.78-3.82 (m, 1H), 2.11 (s, 3H), 2.08 (s, 3H), 2.03 (s, 3H), 2.01 (s, 3H).

Weighing 1 g of the compound 31, dissolving in 5 mL of anhydrous methanol, adding 10 mL of 0.5N NaOMe-MeOH solution, stirring at room temperature overnight, adding an appropriate amount of strong acid cation exchange resin, further stirring for 15 min, filtering when the pH value of the system is measured to be neutral or weakly acidic, and concentrating filtrate to obtain 420 mg of compound 32 with yield of 76.4%.

$^1$H NMR (400 Hz, D$_2$O) δ 4.68 (d, J=8.8 Hz, 1H), 3.84-3.88 (m, 1H), 3.66-3.71 (m, 1H), 3.46-3.48 (m, 2H), 3.29-3.38 (m, 1H), 3.21 (t, J=9.0 Hz, 1H).

Dissolving 23 mL of ethylene glycol (compound 33) in 100 mL of dried tetrahydrofuran, cooling to 0° C., adding 5.5 g of sodium hydride in small batches, further reacting at the temperature for 2 h, weighing 10 g of 3-bromo-1-propyne, dissolving in 30 mL of dried tetrahydrofuran, slowly and dropwise adding into the above reaction, reacting at room temperature overnight, adding 20 mL of water into the reaction system, removing tetrahydrofuran by concentration, extracting with ethyl acetate (40 mL×3), combining organic layers, dying with anhydrous sodium sulfate, filtering, concentrating, and separating by column chromatography to obtain 5.5 g of compound 34 with yield of 64.9%.

$^1$H NMR (400 Hz, DMSO-d$_6$) δ 4.64 (t, J=5.6 Hz, 1H), 4.14 (d, J=2.4 Hz, 2H), 3.49-3.52 (m, 2H), 3.44-3.47 (m, 2H), 3.88 (t, J=2.4 Hz, 1H).

Weighing 1 g of the compound 34, dissolving in 50 mL of dichloromethane, adding 2 g of triethylamine and 3 g of p-nitrophenyl chloroformate, stirring at room temperature overnight, concentrating, and separating by column chromatography to obtain 1 g of compound 35 with yield of 37.7%.

Weighing 392 mg of SN38, dissolving in 20 mL of 1:1 DCM-DMF mixed solvent, adding 200 mg of triethylamine and 310 mg of the compound 35 in sequence, stirring at room temperature overnight, vacuum concentrating, and separating by column chromatography to obtain 300 mg of compound 36 with yield of 57.9%.

$^1$H NMR (400 Hz, DMSO-$d_6$) δ 8.22 (d, J=9.2 Hz, 1H), 8.16 (d, J=2.8 Hz, 1H), 7.78 (dd, J=9.2, 2.4 Hz, 1H), 7.34 (s, 1H), 6.52 (s, 1H), 5.44 (s, 2H), 5.34 (s, 2H), 4.41-4.43 (m, 2H), 4.24 (d, J=2.4 Hz, 2H), 3.77-3.79 (m, 2H), 3.51 (t, J=2.4 Hz, 1H), 3.18-3.21 (m, 2H), 1.85-1.90 (m, 2H), 1.30 (t, J=7.6 Hz, 3H), 0.89 (t, J=7.4 Hz, 3H).

Dissolving 157 mg of the compound 36 and 63 mg of the compound 32 in 10 mL of 1:1 THF-H$_2$O, adding 25 mg of anhydrous copper sulfate and 30 mg of sodium ascorbate in sequence, stirring at room temperature overnight, concentrating, and separating by column chromatography to obtain 135 mg of compound 37 with yield of 61.6%.

$^1$H NMR (400 Hz, DMSO-$d_6$) δ 8.34 (s, 1H), 8.23 (d, J=9.2 Hz, 1H), 8.17 (d, J=2.4 Hz, 1H), 7.77 (dd, J=9.2, 2.8 Hz, 1H), 7.34 (s, 1H), 6.52 (s, 1H), 5.55 (d, J=9.2 Hz, 1H), 5.44 (s, 2H), 5.38 (d, J=6.0 Hz, 1H), 5.34 (s, 2H), 5.27 (d, J=4.8 Hz, 1H), 5.14 (d, J=5.6 Hz, 1H), 4.62-4.63 (m, 3H), 4.41-4.44 (m, 2H), 3.69-3.82 (m, 4H), 3.40-3.46 (m, 3H), 3.19-3.24 (m, 3H), 1.86-1.89 (m, 2H), 1.29 (t, J=7.6 Hz, 3H), 0.88 (t, J=7.2 Hz, 3H).

Example 2 Synthesis of Compound 42

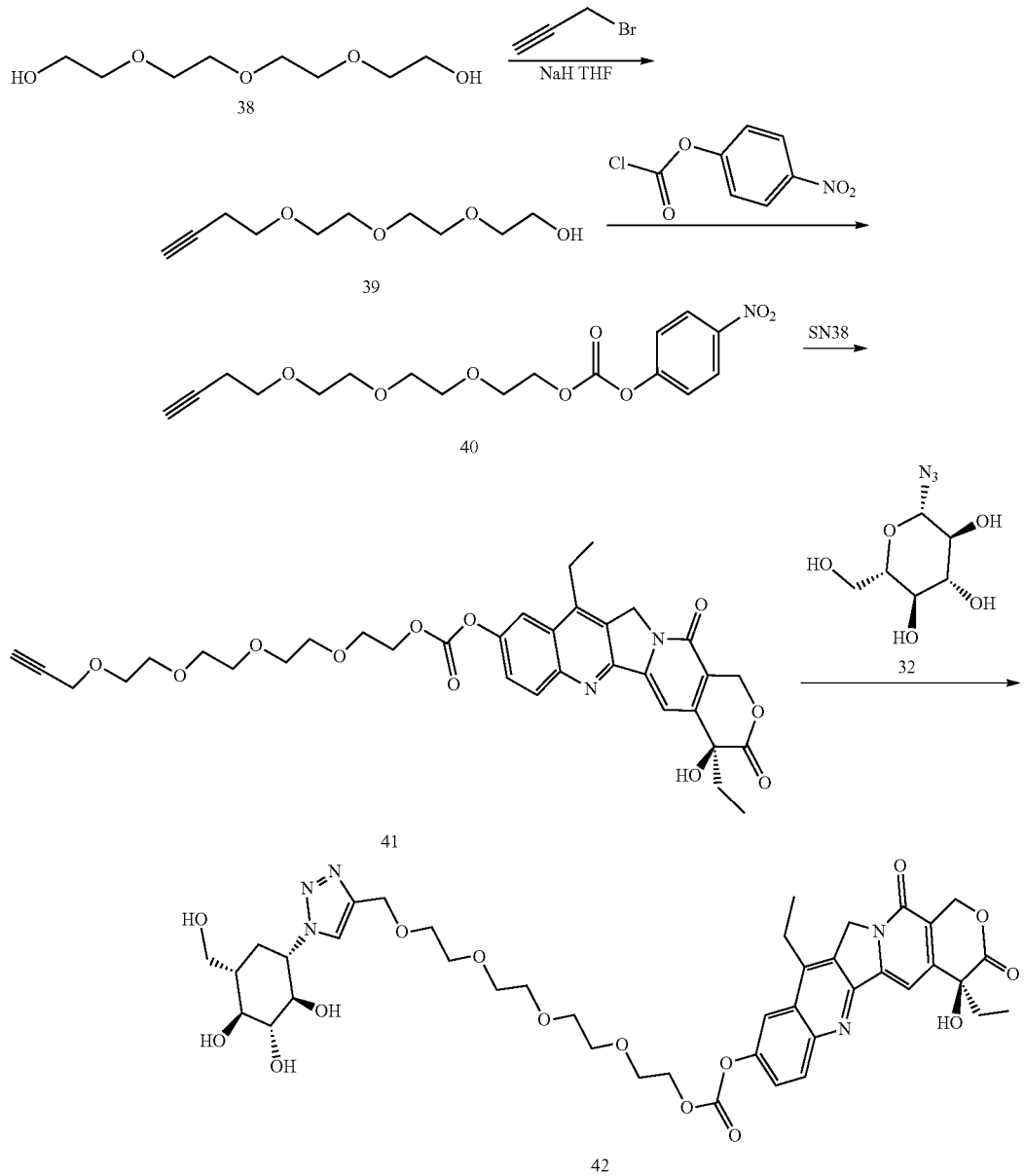

Dissolving 80 mL of tetraethylene glycol (compound 38) in 200 mL of dried tetrahydrofuran, cooling to 0° C., adding 5.5 g of sodium hydride in small batches, further reacting at the temperature for 2, weighing 10 g of 3-bromo-1-propyne, dissolving in 30 mL of dried tetrahydrofuran, slowly and dropwise adding into the above reaction, reacting at room temperature overnight, adding 20 mL of water into the reaction system, removing tetrahydrofuran by concentration, extracting with ethyl acetate (60 mL×3), combining organic layers, drying with anhydrous sodium sulfate, filtering, concentrating, and separating by column chromatography to obtain 11.7 g of compound 39 with yield of 59.5%.

$^1$H NMR (400 Hz, CDCl$_3$) δ 4.20-4.24 (m, 2H), 3.67-3.71 (m, 14H), 3.60-3.62 (m, 2H), 2.46 (t, J=2.4 Hz, 1H).

Weighing 1 g of the compound 39, dissolving in 50 mL of dichloromethane, adding 870 mg of triethylamine and 1.3 g of p-nitrophenyl chloroformate, stirring at room temperature overnight, concentrating, and separating by column chromatography to obtain 600 mg of compound 40 with yield of 35.1%.

Weighing 392 mg of SN38, dissolving in 20 mL of 1:1 DCM-DMF mixed solvent, adding 200 mg of triethylamine and 397 mg of the compound 40 in sequence, stirring at room temperature overnight, vacuum concentrating, and separating by column chromatography to obtain 391 mg of compound 41 with yield of 60.3%.

$^1$H NMR (400 Hz, DMSO-d$_6$) δ 8.22 (d, J=9.2 Hz, 1H), 8.16 (d, J=2.4 Hz, 1H), 7.78 (dd, J=9.2, 2.8 Hz, 1H), 7.34 (s, 1H), 6.52 (s, 1H), 5.44 (s, 2H), 5.33 (s, 2H), 4.38-4.41 (m, 2H), 4.14 (d, J=2.4 Hz, 2H), 3.73-3.76 (m, 2H), 3.51-3.57 (m, 12H), 3.40 (t, J=2.4 Hz, 1H), 3.18-3.21 (m, 2H), 1.86-1.90 (m, 2H), 1.30 (t, J=7.6 Hz, 3H), 0.89 (t, J=7.4 Hz, 3H).

Dissolving 160 mg of the compound 41 and 65 mg of the compound 32 in 10 mL of 1:1 THF-H$_2$O, adding 20 mg of anhydrous copper sulfate and 24 mg of sodium ascorbate in sequence, stirring at room temperature overnight, concentrating, and separating by column chromatography to obtain 60 mg of compound 42 with yield of 28.5%.

$^1$H NMR (400 Hz, DMSO-d$_6$) δ 8.27 (s, 1H), 8.23 (d, J=9.2 Hz, 1H), 8.17 (d, J=2.8 Hz, 1H), 7.78 (dd, J=9.2, 2.8 Hz, 1H), 7.34 (s, 1H), 6.52 (s, 1H), 5.51 (d, J=9.6 Hz, 1H), 5.44 (s, 2H), 5.36 (d, J=6.0 Hz, 1H), 5.34 (s, 2H), 5.26 (d, J=4.8 Hz, 1H), 5.13 (d, J=5.6 Hz, 1H), 4.62 (t, J=5.6 Hz, 1H), 4.53 (s, 2H), 4.38-4.40 (m, 2H), 3.72-3.76 (m, 4H), 3.53-3.57 (m, 10H), 3.42-3.46 (m, 2H), 3.18-3.28 (m, 4H), 1.84-1.90 (m, 4H), 1.29 (t, J=7.6 Hz, 3H), 0.87 (t, J=7.6 Hz, 3H).

Example 3 Synthesis of Compound 47

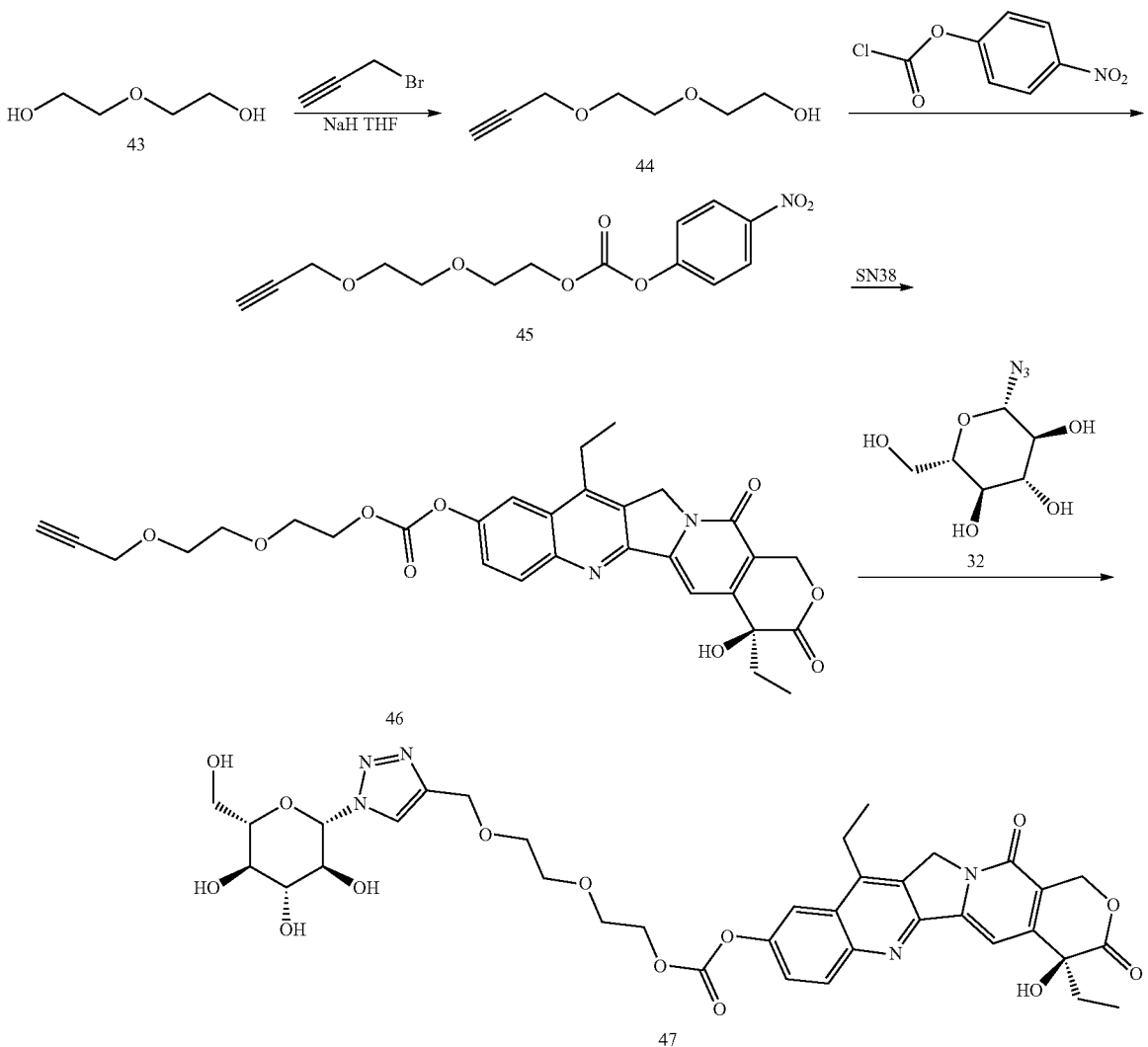

Dissolving 46 mL of diethylene glycol (compound 43) in 100 mL of dried tetrahydrofuran, cooling to 0° C., adding 5.5 g of sodium hydride in small batches, further reacting at the temperature for 2 h, weighing 10 g of 3-bromo-1-propyne, dissolving in 30 mL of dried tetrahydrofuran, slowly and dropwise adding into the above reaction, reacting at room temperature overnight, adding 20 mL of water into the reaction system, removing tetrahydrofuran by concentration, extracting with ethyl acetate (50 mL×3), combining organic layers, drying with anhydrous sodium sulfate, filtering, concentrating, and separating by column chromatography to obtain 5.53 g of compound 44 with yield of 45.3%.

$^1$H NMR (400 Hz, DMSO-d$_6$) δ 4.56 (t, J=5.6 Hz, 1H), 4.14 (d, J=2.4 Hz, 2H), 3.51-3.59 (m, 4H), 3.46-3.49 (m, 2H), 3.40-3.44 (m, 3H).

Weighing 1 g of the compound 44, dissolving in 50 mL of dichloromethane, adding 1.4 g of triethylamine and 2.1 g of p-nitrophenyl chloroformate, stirring at room temperature overnight, concentrating, and separating by column chromatography to obtain 603 mg of compound 45 with yield of 28.1%.

$^1$H NMR (400 Hz, DMSO-d$_6$) δ 7.56-7.58 (m, 2H), 6.91-6.95 (m, 2H), 4.37-4.39 (m, 2H), 4.16 (d, J=2.4 Hz, 2H), 3.70-3.72 (m, 2H), 3.59-3.62 (m, 4H), 3.42 (t, J=2.4 Hz, 1H).

Weighing 392 mg of SN38, dissolving in 20 mL of 1:1 DCM-DMF mixed solvent, adding 200 mg of triethylamine and 309 mg of the compound 45 in sequence, stirring at room temperature overnight, concentrating, and separating by column chromatography to obtain 357 mg of compound 46 with yield of 63.6%.

$^1$H NMR (400 Hz, DMSO-d$_6$) δ 8.23 (d, J=9.2 Hz, 1H), 8.16 (d, J=2.4 Hz, 1H), 7.78 (dd, J=9.2, 2.8 Hz, 1H), 7.34 (s, 1H), 6.52 (s, 1H), 5.44 (s, 2H), 5.34 (s, 2H), 4.38-4.41 (m, 2H), 4.18 (d, J=2.4 Hz, 2H), 3.72-3.75 (m, 2H), 3.60-3.62 (m, 4H), 3.44 (t, J=2.4 Hz, 1H), 3.18-3.21 (m, 2H), 1.86-1.90 (m, 2H), 1.30 (t, J=7.6 Hz, 3H), 0.89 (t, J=7.4 Hz, 3H).

Dissolving 95 mg of the compound 46 and 35 mg of the compound 32 in 10 mL of 1:1 THF-H$_2$O, adding 27 mg of anhydrous copper sulfate and 33 mg of sodium ascorbate in sequence, stirring at room temperature overnight, concentrating, and separating by column chromatography to obtain 80 mg of compound 47 with yield of 61.6%.

$^1$H NMR (400 Hz, DMSO-d$_6$) δ 8.31 (s, 1H), 8.22 (d, J=9.2 Hz, 1H), 8.17 (d, J=3.0 Hz, 1H), 7.78 (dd, J=9.2, 2.8 Hz, 1H), 7.34 (s, 1H), 6.52 (s, 1H), 5.53 (d, J=9.2 Hz, 1H), 5.44 (s, 2H), 5.13-5.33 (m, 5H), 4.57-4.63 (m, 3H), 4.38-4.40 (m, 2H), 3.67-3.79 (m, 4H), 3.64 (s, 4H), 3.37-3.45 (m, 3H), 3.17-3.25 (m, 3H), 1.82-1.91 (m, 2H), 1.29 (t, J=7.6 Hz, 3H), 0.89 (t, J=7.4 Hz, 3H).

Example 4 Synthesis of Compound 52

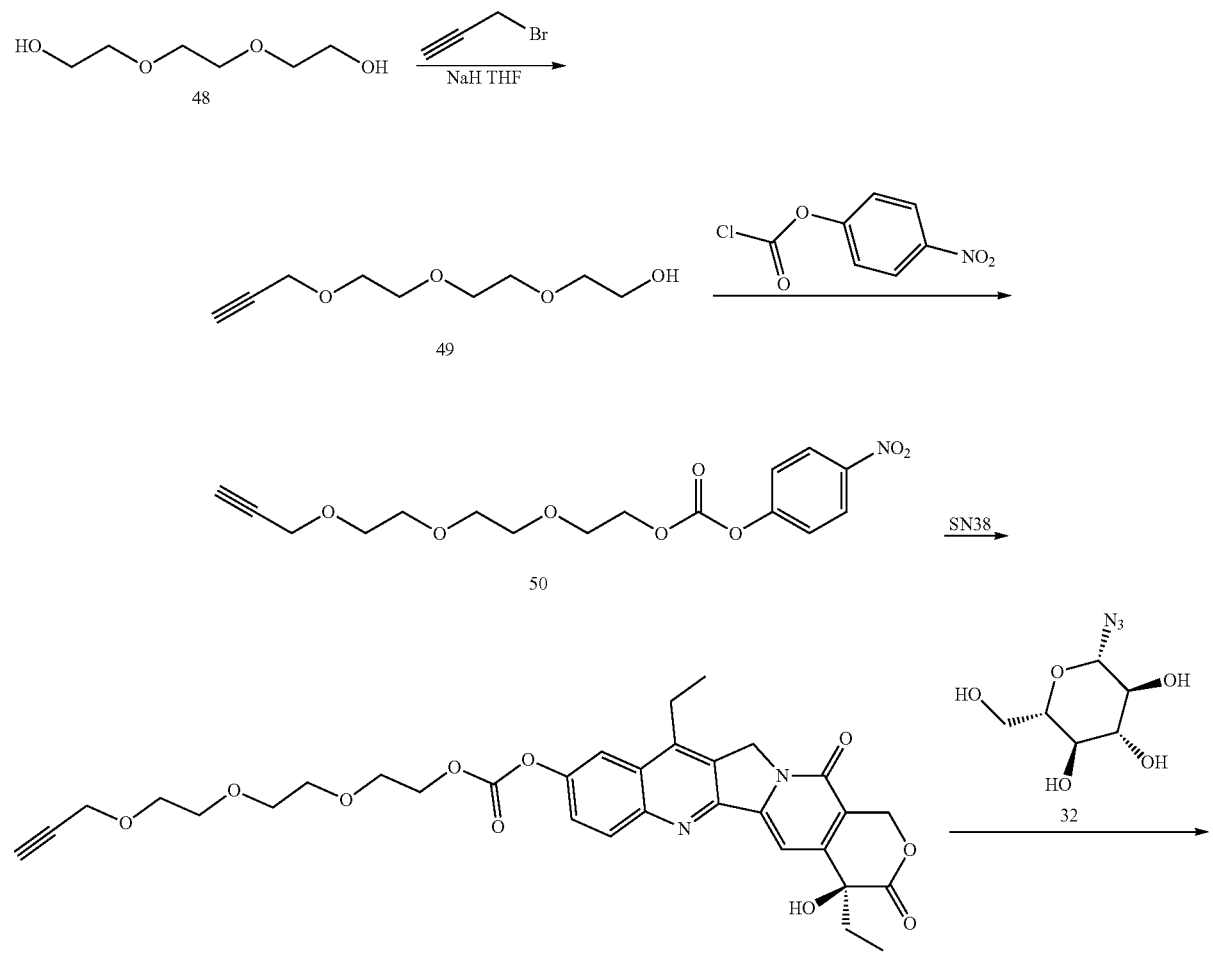

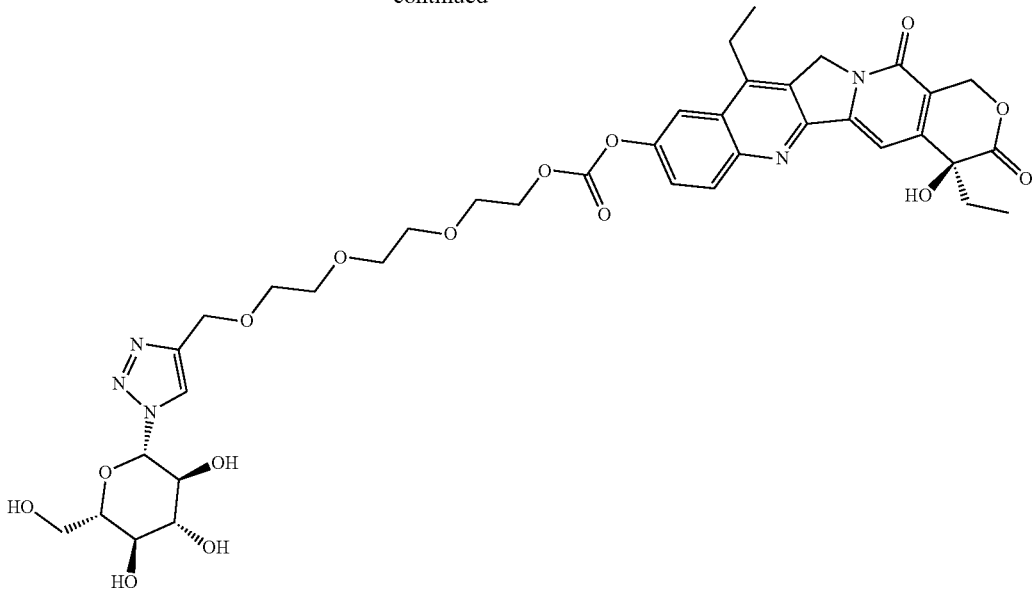

52

Dissolving 69 mL of triethylene glycol (compound 48) in 150 mL of dried tetrahydrofuran, cooling to 0° C., adding 5.5 g of sodium hydride in small batches, further reacting at the temperature for 2 h, weighing 10 g of 3-bromo-1-propyne, dissolving in 30 mL of dried tetrahydrofuran, slowly and dropwise adding into the above reaction, reacting at room temperature overnight, adding 20 mL of water into the reaction system, removing tetrahydrofuran by concentration, extracting with ethyl acetate (50 mL×3), combining organic layers, drying with anhydrous sodium sulfate, filtering, concentrating, and separating by column chromatography to obtain 7.6 g of compound 49 with yield of 47.8%.

$^1$H NMR (400 Hz, DMSO-$d_6$) δ 4.54 (t, J=5.4 Hz, 1H), 4.14 (d, J=2.4 Hz, 2H), 3.47-3.53 (m, 10H), 3.36-3.43 (m, 3H).

Weighing 1 g of the compound 49, dissolving in 50 mL of dichloromethane, adding 1.1 g of triethylamine and 1.6 g of p-nitrophenyl chloroformate, stirring at room temperature overnight, concentrating, and separating by column chromatography to obtain 685 mg of compound 50 with 36.5% yield.

Weighing 392 mg of SN38, dissolving in 20 mL of 1:1 DCM-DMF mixed solvent, adding 200 mg of triethylamine and 353 mg of the compound 50, stirring at room temperature overnight, vacuum concentrating, and separating by column chromatography to obtain 375 mg of compound 51 with yield of 61.9%.

$^1$H NMR (400 Hz, DMSO-$d_6$) δ 8.22 (d, J=9.2 Hz, 1H), 8.16 (d, J=2.4 Hz, 1H), 7.78 (dd, J=9.2, 2.4 Hz, 1H), 7.34 (s, 1H), 6.52 (s, 1H), 5.44 (s, 2H), 5.34 (s, 2H), 4.38-4.41 (m, 2H), 4.15 (d, J=2.4 Hz, 2H), 3.73-3.75 (m, 2H), 3.56-3.62 (m, 8H), 3.41 (t, J=2.4 Hz, 1H), 3.17-3.23 (m, 2H), 1.84-1.91 (m, 2H), 1.30 (t, J=7.6 Hz, 3H), 0.89 (t, J=7.4 Hz, 3H).

Dissolving 146 mg of the compound 51 and 50 mg of the compound 32 in 10 mL of 1:1 THF-$H_2O$, adding 39 mg of anhydrous copper sulfate and 48 mg of sodium ascorbate in sequence, stirring at room temperature overnight, concentrating, and separating by column chromatography to obtain 75 of mg compound 52 with yield of 38.5%.

$^1$H NMR (400 Hz, DMSO-$d_6$) δ 8.29 (s, 1H), 8.19 (d, J=9.2 Hz, 1H), 8.17 (d, J=2.8 Hz, 1H), 7.78 (dd, J=9.2, 2.8 Hz, 1H), 7.34 (s, 1H), 6.52 (s, 1H), 5.52 (d, J=9.6 Hz, 1H), 5.44 (s, 2H), 5.36 (d, J=6.0 Hz, 1H), 5.34 (s, 2H), 5.26 (d, J=4.8 Hz, 1H), 5.13 (d, J=5.6 Hz, 1H), 4.62 (t, J=5.6 Hz, 1H), 4.55 (s, 2H), 4.38-4.40 (m, 2H), 3.67-3.77 (m, 4H), 3.56-3.61 (m, 8H), 3.36-3.46 (m, 3H), 3.16-3.24 (m, 3H), 1.86-1.90 (m, 2H), 1.30 (t, J=7.2 Hz, 3H), 0.89 (t, J=7.2 Hz, 3H).

Example 5 Synthesis of Compound 56

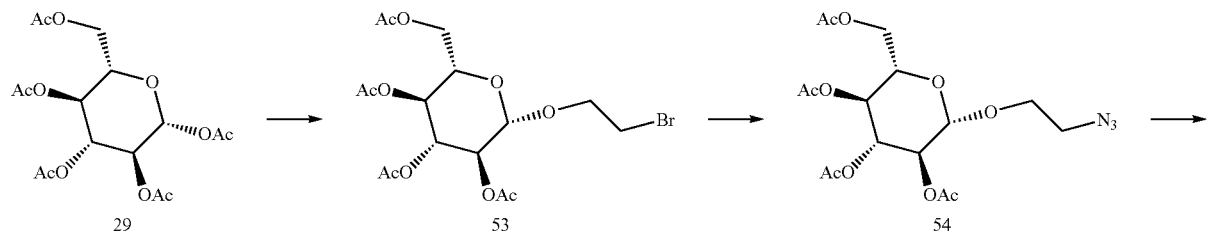

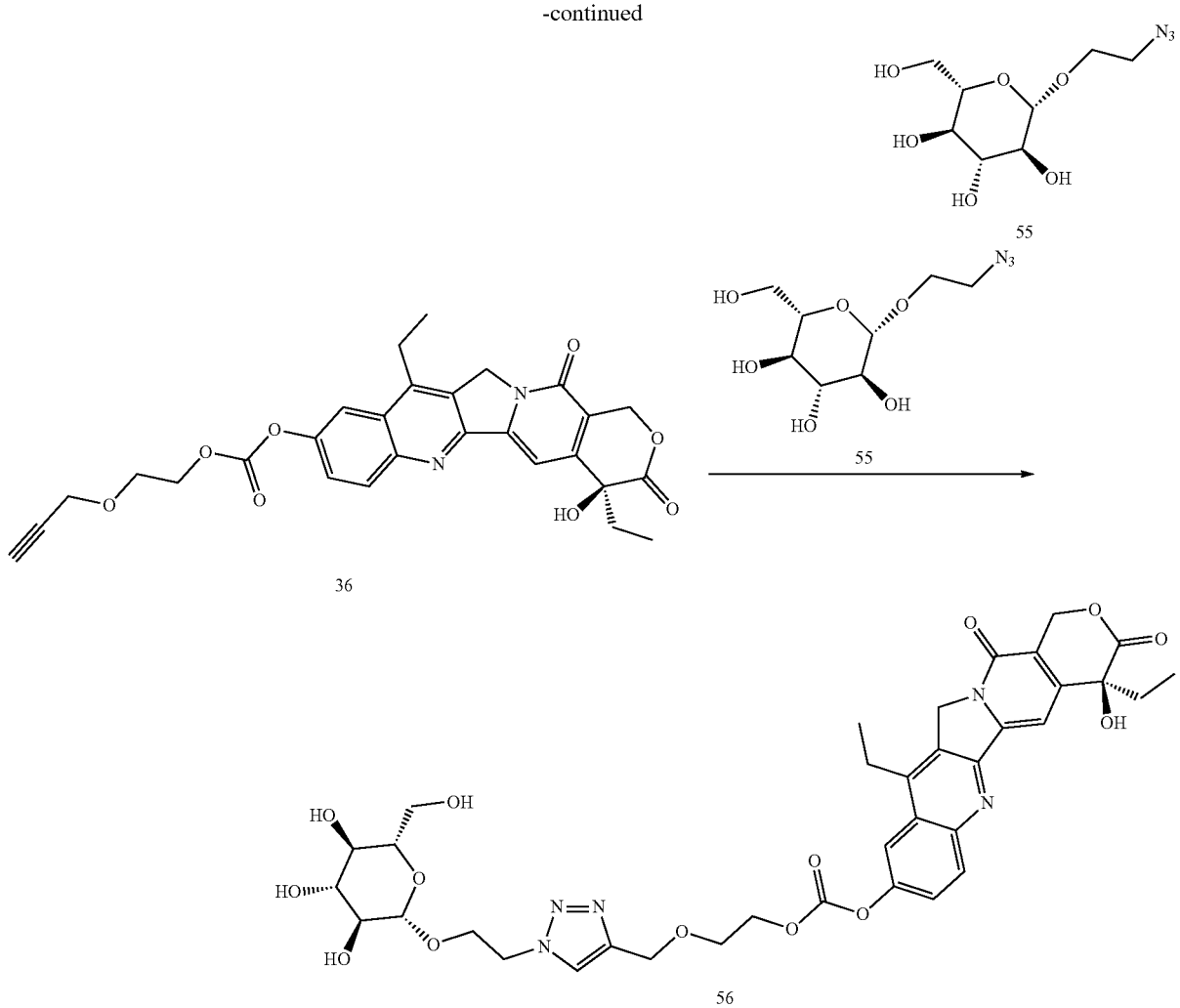

Weighing 18 g of compound 29, dissolving in 150 mL of dichloromethane, adding 6.3 g of bromoethanol and 8.7 mL of boron trifluoride diethyletherate, reacting at room temperature overnight, adding saturated sodium bicarbonate until no gas is produced, extracting with DCM for three times, combining organic layers, drying, concentrating, and separating by column chromatography to obtain 10 g of compound 53 with yield of 47.7%.

$^1$H NMR (400 Hz, CDCl$_3$) δ 5.25 (t, J=9.6 Hz, 1H), 4.87-4.93 (m, 2H), 4.77-4.81 (m, 1H), 4.15-4.20 (m, 1H), 3.96-4.00 (m, 2H), 3.77-3.82 (m, 1H), 3.55-3.62 (m, 2H), 2.02 (s, 3H), 2.00 (s, 3H), 1.98 (s, 3H), 1.94 (s, 3H).

Weighing 10 g of the compound 53, dissolving in 150 mL of DMF, adding 2.86 g of sodium azide, reacting at 60° C. overnight while monitoring complete reaction by TLC, cooling to room temperature, adding an appropriate amount of water, extracting with ethyl acetate (100 mL×3), removing the organic layer and a small amount of residual DMF by concentration, adding an appropriate amount of ethanol to separate out solid, and filtering to obtain 6.9 g of compound 54 with yield of 75.2%.

$^1$H NMR (400 Hz, CDCl$_3$) δ 5.22 (t, J=9.4 Hz, 1H), 5.10 (t, J=9.6 Hz, 1H), 5.00-5.04 (m, 1H), 4.60 (d, J=8.0 Hz, 1H), 4.24-4.28 (m, 1H), 4.14-4.17 (m, 1H), 4.02-4.05 (m, 1H), 3.67-3.74 (m, 2H), 3.46-3.53 (m, 1H), 3.27-3.32 (m, 1H), 2.09 (s, 3H), 2.05 (s, 3H), 2.03 (s, 3H), 2.01 (s, 3H).

Weighing 1 g of the compound 54, dissolving in 5 mL of anhydrous methanol, adding 10 mL of 0.5N NaOMe-MeOH solution, stirring at room temperature overnight, adding an appropriate amount of strong acid cation exchange resin, further stirring for 15 min, filtering when the pH value of the system is measured to be neutral or weakly acidic, and concentrating filtrate to obtain 430 mg of compound 55 with yield 72.0%.

$^1$H NMR (400 Hz, D$_2$O) δ 4.44 (d, J=8.0 Hz, 1H), 3.97-4.02 (m, 1H), 3.84-3.88 (m, 1H), 3.76-3.80 (m, 1H), 3.64-3.69 (m, 1H), 3.38-3.51 (m, 4H), 3.29-3.35 (m, 1H), 3.24 (t, J=8.0 Hz, 1H).

Dissolving 170 mg of the compound 36 and 82 mg of the compound 55 in 16 mL of THF-H$_2$O, adding 26 mg of anhydrous copper sulfate and 33 mg of sodium ascorbate in sequence, stirring at room temperature overnight, concentrating, and separating by column chromatography to obtain 110 mg of compound 56 with yield of 43.8%.

$^1$H NMR (400 Hz, DMSO-d$_6$) δ 8.22 (d, J=9.2 Hz, 1H), 8.20 (s, 1H), 8.17 (d, J=3.0 Hz, 1H), 7.78 (dd, J=9.2, 3.0 Hz, 1H), 7.34 (s, 1H), 6.52 (s, 1H), 5.44 (s, 2H), 5.34 (s, 2H), 4.91-5.01 (m, 3H), 4.57-4.61 (m, 4H), 4.40-4.42 (m, 2H), 4.24 (d, J=8.0 Hz, 1H), 4.07-4.11 (m, 1H), 3.89-3.95 (m, 1H), 3.78-3.80 (m, 2H), 3.68 (d, J=5.6 Hz, 1H), 3.42-3.46 (m, 1H), 2.96-3.17 (m, 7H), 1.82-1.91 (m, 2H), 1.31 (t, J=7.4 Hz, 3H), 0.89 (t, J=7.4 Hz, 3H).

Example 6 Synthesis of Compound 57

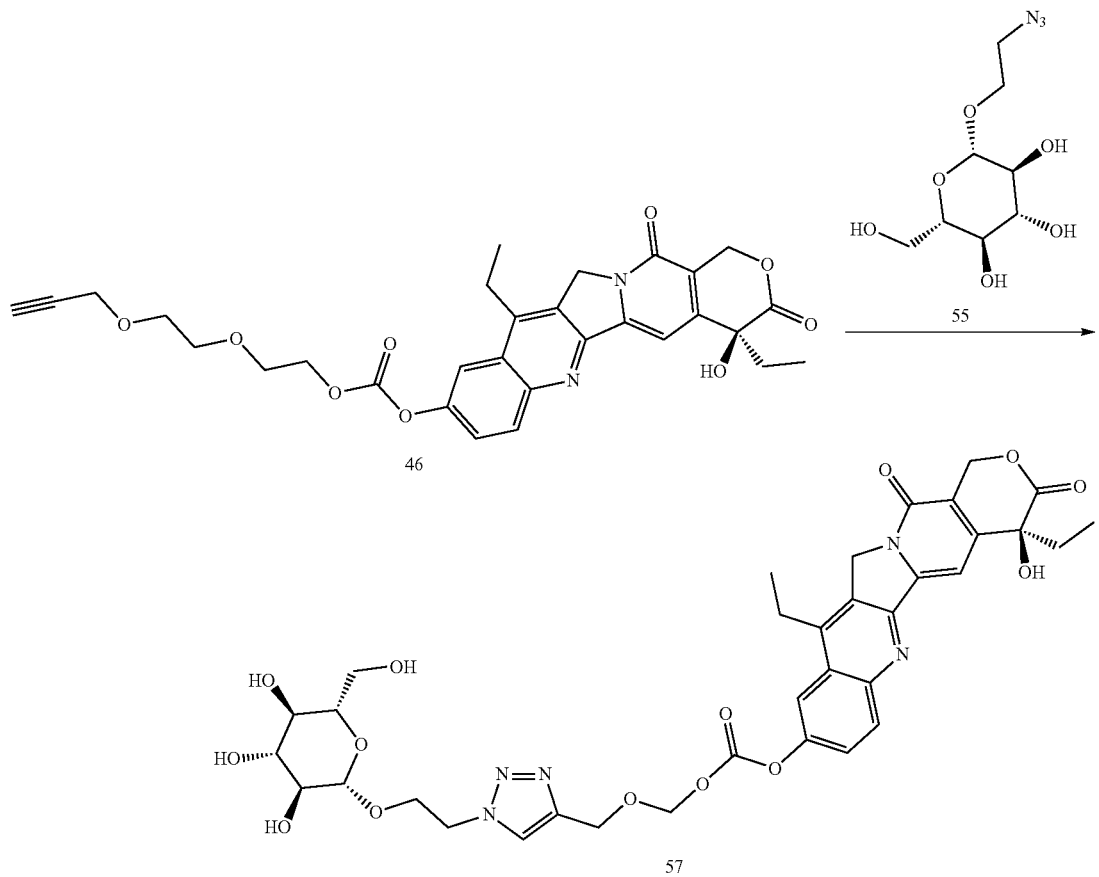

Dissolving 80 mg of the compound 46 and 36 mg of compound 55 in 14 mL of THF-H$_2$O, adding 23 mg of anhydrous copper sulfate and 28 mg of sodium ascorbate in sequence, stirring at room temperature overnight, concentrating, and separating by column chromatography to obtain 50 mg of compound 57 with yield of 43.3%.

$^1$H NMR (400 Hz, DMSO-d$_6$) δ 8.22 (d, J=9.2 Hz, 1H), 8.16 (s, 2H), 7.78 (dd, J=9.2, 2.4 Hz, 1H), 7.34 (s, 1H), 6.52 (s, 1H), 5.44 (s, 2H), 5.34 (s, 2H), 5.07 (d, J=4.8 Hz, 1H), 4.93 (dd, J=12.8, 4.8 Hz, 2H), 4.49-4.57 (m, 5H), 4.39 (t, J=4.4 Hz, 2H), 4.23 (d, J=7.6 Hz, 1H), 4.07-4.10 (m, 1H), 3.89-3.92 (m, 1H), 3.62-3.75 (m, 7H), 3.42-3.45 (m, 1H), 3.10-3.19 (m, 4H), 2.97-3.05 (m, 2H), 1.86-1.90 (m, 2H), 1.30 (t, J=7.6 Hz, 3H), 0.89 (t, J=7.2 Hz, 3H).

Example 7 Synthesis of Compound 58

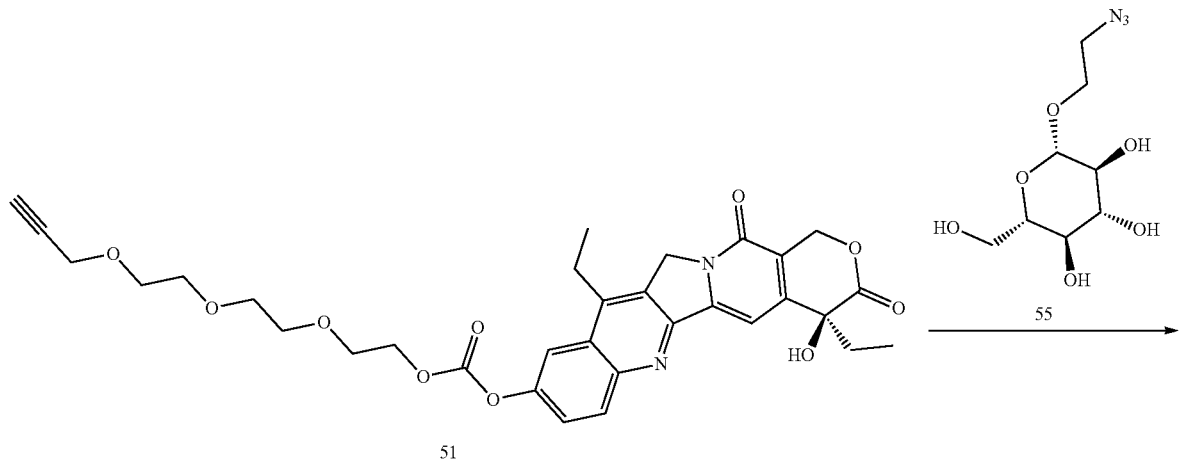

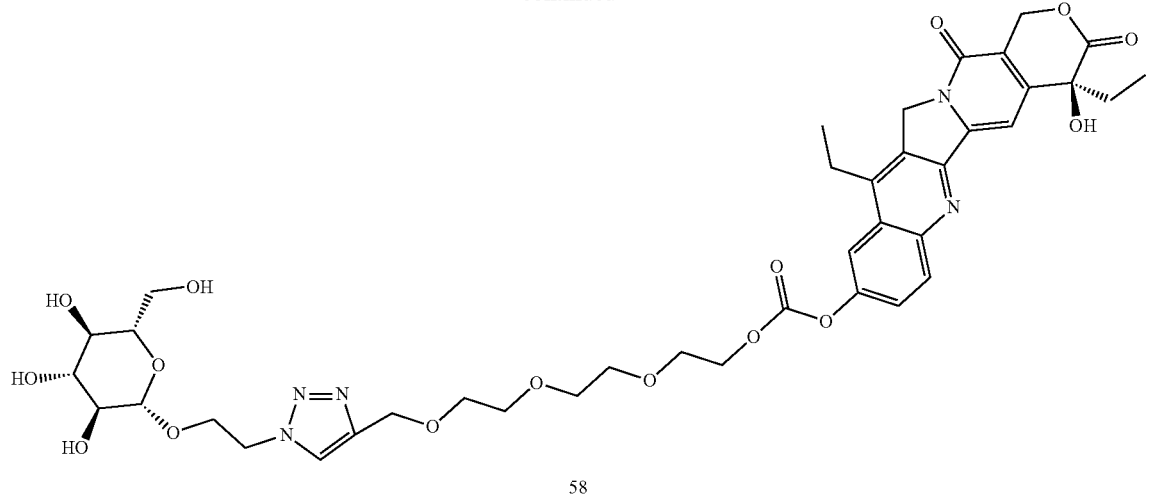

58

Dissolving 98 mg of the compound 51 and 40 mg of the compound 55 in 14 mL of THF-H$_2$O, adding 26 mg of anhydrous copper sulfate and 32 mg of sodium ascorbate in sequence, stirring at room temperature overnight, concentrating, and separating by column chromatography to obtain 65 mg of compound 58 with yield of 48.5%.

$^1$H NMR (400 Hz, DMSO-d$_6$) δ 8.22 (d, J=9.2 Hz, 1H), 8.16 (d, J=2.4 Hz, 1H), 8.15 (s, 1H), 7.78 (dd, J=9.2, 2.4 Hz, 1H), 7.34 (s, 1H), 6.52 (s, 1H), 5.44 (s, 2H), 5.34 (s, 2H), 5.07 (d, J=3.2 Hz, 1H), 4.92 (dd, J=12.8, 4.8 Hz, 2H), 4.49-4.58 (m, 5H), 4.38-4.39 (m, 2H), 4.22 (d, J=8.0 Hz, 1H), 4.07-4.09 (m, 1H), 3.89-3.92 (m, 1H), 3.73-3.75 (m, 2H), 3.65-3.69 (m, 1H), 3.56-3.61 (m, 8H), 3.42-3.45 (m, 1H), 3.10-3.18 (m, 4H), 2.96-3.05 (m, 2H), 1.86-1.90 (m, 2H), 1.30 (t, J=7.6 Hz, 3H), 0.89 (t, J=7.2 Hz, 3H).

Example 8 Synthesis of Compound 59

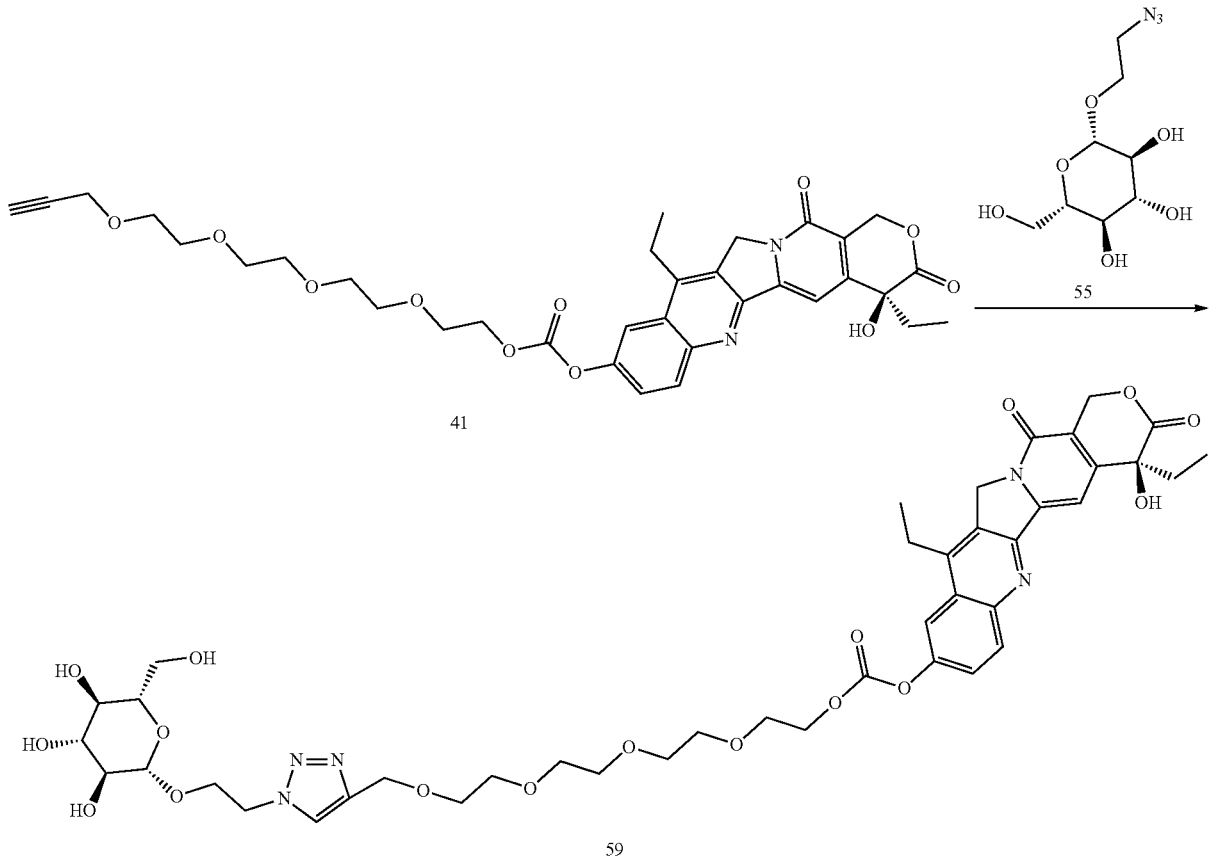

Dissolving 316 mg of the compound 41 and 121 mg of the compound 55 in 16 mL of THF-H₂O, adding 78 mg of anhydrous copper sulfate and 96 mg of sodium ascorbate in sequence, stirring at room temperature overnight, concentrating, and separating by column chromatography to obtain 100 mg of compound 59 with yield of 22.9%.

¹H NMR (400 Hz, DMSO-d₆) δ 8.23 (d, J=9.2 Hz, 1H), 8.16 (s, 1H), 8.14 (s, 1H), 7.78 (d, J=9.2 Hz, 1H), 7.34 (s, 1H), 6.52 (s, 1H), 5.44 (s, 2H), 5.34 (s, 2H), 5.06 (d, J=4.8 Hz, 1H), 4.92 (dd, J=12.8, 4.8 Hz, 2H), 4.51-4.56 (m, 5H), 4.39 (s, 2H), 4.22 (d, J=7.6 Hz, 1H), 4.06-4.09 (m, 1H), 3.89-3.91 (m, 1H), 3.66-3.74 (m, 3H), 3.53-3.55 (m, 11H), 3.37-3.44 (m, 1H), 3.13-3.18 (m, 5H), 2.96-3.04 (m, 2H), 1.86-1.90 (m, 2H), 1.30 (t, J=7.2 Hz, 3H), 0.89 (t, J=6.8 Hz, 3H).

Example 9 Synthesis of Compound 66

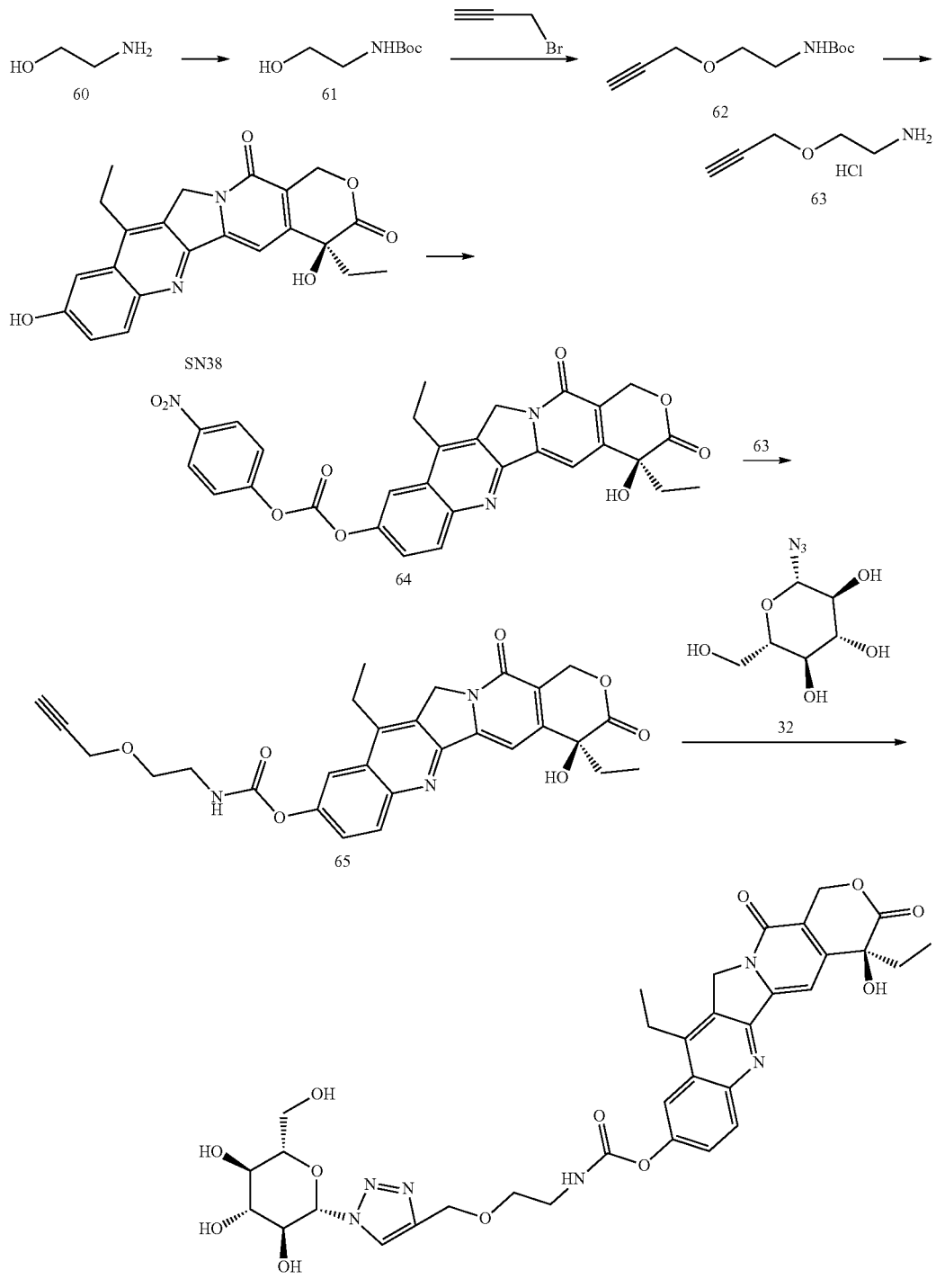

Weighing 5 g of compound 60 and 16.6 g of triethylamine, dissolving in 150 mL of dichloromethane, cooling to 0° C., slowly and dropwise adding 11.8 g of di-tert-butyl dicarbonate, reacting at room temperature overnight, washing the reaction liquid with 1N HCl (100 mL×3), combining organic layers, drying with anhydrous sodium sulfate, filtering, concentrating, and separating by column chromatography to obtain 5 g of compound 61 with yield of 37.9%.

$^1$H NMR (400 Hz, DMSO-$d_6$) δ 6.45 (s, 1H), 4.57 (t, J=5.6 Hz, 1H), 3.33-3.38 (m, 2H), 2.95-2.99 (m, 2H), 1.37 (s, 9H).

Weighing 2 g of the compound 61, dissolving in 40 mL of tetrahydrofuran, adding 458 mg of tetrabutylammonium iodide, 280 mg of sodium iodide and 1.77 g of 3-bromo-1-propyne, stirring at room temperature, adding 7 g of potassium hydroxide in small batches, reacting at room temperature overnight, removing tetrahydrofuran by concentration, adding 30 mL of water, extracting with ethyl acetate 30 mL×3), combining organic layers, drying with anhydrous sodium sulfate, filtering, concentrating, and separating by column chromatography to obtain 1.9 g of compound 62 with yield of 76.9%.

Weighing 1.8 g of the compound 62, dissolving in 20 mL of methanol, adding 20 mL of 3N HCl solution, stirring at room temperature overnight, and concentrating to obtain 900 mg of compound 63 with yield of 73.8%.

$^1$H NMR (400 Hz, $D_2O$) δ 4.22 (s, 2H), 3.78 (t, J=4.2 Hz, 2H), 3.18 (t, J=4.0 Hz, 2H).

Weighing 490 mg of SN38, dissolving in 30 mL of DMF, cooling to 0° C., adding 320 mg of DiPEA and 330 mg of p-nitrophenyl chloroformate, further reacting at the temperature for 0.5 h, reacting at room temperature for 3 h to obtain intermediate 64, adding 320 mg DiPEA and 253 mg of the compound 63, reacting at room temperature overnight while monitoring the reaction well proceeded by TLC, removing DMF by concentration, and separating by column chromatography to obtain 420 mg of crude compound 65.

Dissolving 210 mg of the compound 65 and 160 mg of the compound 32 into 16 mL of THF-$H_2O$, adding 124 mg of anhydrous copper sulfate and 153 mg of sodium ascorbate in sequence, stirring at room temperature overnight, concentrating, and separating by column chromatography to obtain 60 mg of compound 66 with two-step yield of 13.3%.

$^1$H NMR (400 Hz, DMSO-$d_6$) δ 8.33 (s, 1H), 8.17 (d, J=8.8 Hz, 1H), 8.04-8.05 (m, 1H), 7.96 (s, 1H), 7.64 (d, J=9.2 Hz, 1H), 7.33 (s, 1H), 6.51 (s, 1H), 5.54 (d, J=9.2 Hz, 1H), 5.44 (s, 2H), 5.38 (d, J=6.0 Hz, 1H), 5.33 (s, 2H), 5.28 (d, J=4.8 Hz, 1H), 5.14 (d, J=5.2 Hz, 1H), 4.60-4.62 (m, 3H), 3.68-3.78 (m, 2H), 3.60 (t, J=5.0 Hz, 2H), 3.37-3.46 (m, 4H), 3.16-3.26 (m, 4H), 1.86-1.90 (m, 2H), 1.30 (t, J=7.4 Hz, 3H), 0.89 (t, J=7.2 Hz, 3H).

Example 10 Synthesis of Compound 67

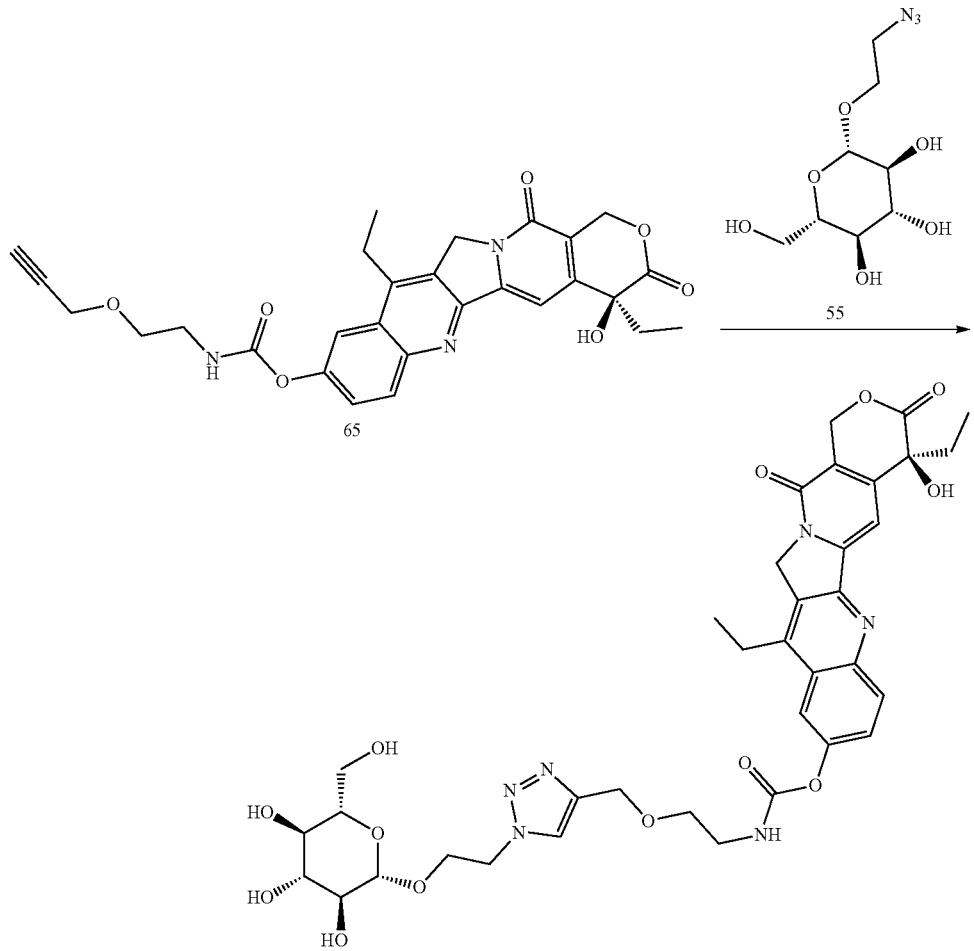

Dissolving 210 mg of the crude compound 65 and 160 mg of the compound 55 in 16 mL of THF-H₂O, adding 124 mg of anhydrous copper sulfate and 153 mg of sodium ascorbate in sequence, stirring at room temperature overnight, concentrating, and separating by column chromatography to obtain 60 mg of compound 67 with yield of 12.5%.

¹H NMR (400 Hz, DMSO-d₆) δ 8.16-8.19 (m, 2H), 8.01 (t, J=1.6 Hz, 1H), 7.95 (d, J=2.4 Hz, 1H), 7.64 (dd, J=9.2, 2.4 Hz, 1H), 7.33 (s, 1H), 6.51 (s, 1H), 5.44 (s, 2H), 5.34 (s, 2H), 5.08 (d, J=4.8 Hz, 1H), 4.94 (dd, J=14.4, 4.8 Hz, 2H), 4.50-4.58 (m, 5H), 4.23 (d, J=7.6 Hz, 1H), 4.07-4.11 (m, 1H), 3.90-3.93 (m, 1H), 3.66-3.70 (m, 1H), 3.58 (t, J=5.6 Hz, 2H), 3.41-3.46 (m, 2H), 3.10-3.20 (m, 5H), 2.95-3.07 (m, 2H), 1.84-1.91 (m, 2H), 1.30 (t, J=7.4 Hz, 3H), 0.88 (t, J=7.2 Hz, 3H).

Example 11 Synthesis of Compound 73

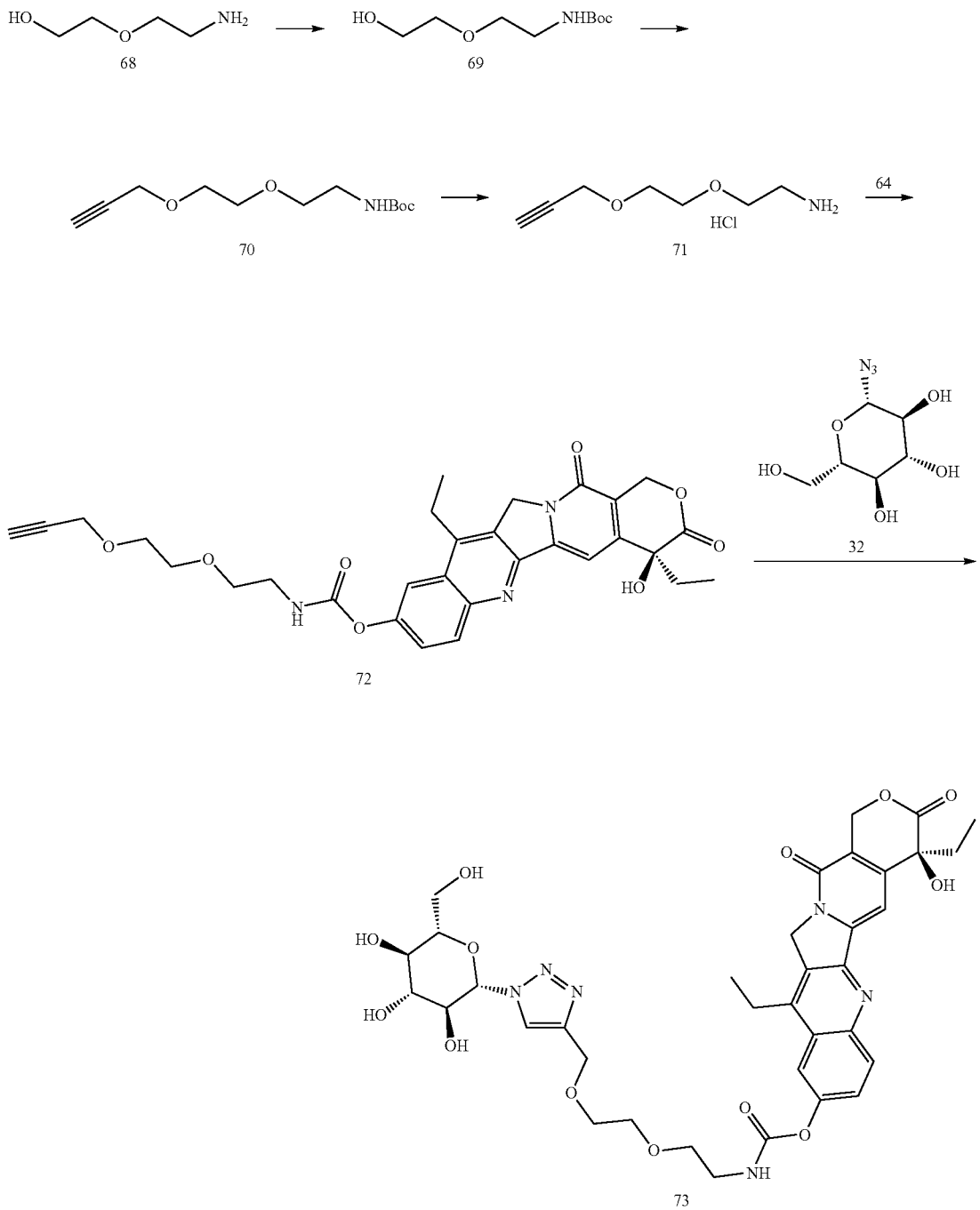

Weighing 10 g of compound 68 and 19.2 g of triethylamine, dissolving in 150 mL of dichloromethane, cooling to 0° C., slowly and dropwise adding 22.9 g of di-tert-butyl dicarbonate, reacting at room temperature overnight, washing the reaction liquid with 1N HCl (100 mL×3), combining organic layers, drying with anhydrous sodium sulfate, filtering, and concentrating to obtain 7.5 g of compound 69 with yield of 38.5%.

$^1$H NMR (400 Hz, DMSO-d$_6$) δ 6.75 (s, 1H), 4.55-4.58 (m, 1H), 3.46-3.50 (m, 2H), 3.36-3.40 (m, 4H), 3.05-3.09 (m, 2H), 1.38 (s, 9H).

Weighing 2 g of the compound 69, dissolving in 40 mL of tetrahydrofuran, adding 360 mg of tetrabutylammonium iodide, 220 mg of sodium iodide and 1.39 g of 3-bromo-1-propyne, stirring at room temperature, adding 5.5 g of potassium hydroxide in small batches, reacting at room temperature overnight, removing tetrahydrofuran by concentration, adding 30 mL of water, extracting with ethyl acetate (30 mL×3), drying organic layers with anhydrous sodium sulfate, filtering, concentrating, and separating by column chromatography to obtain 1.4 g of compound 70 with yield of 59.1%.

Weighing 1.3 g of the compound 70, dissolving in 20 mL of methanol, adding 20 mL of 3N HCl solution, stirring at room temperature overnight, and concentrating to obtain 600 mg of compound 71 with yield of 62.7%.

$^1$H NMR (400 Hz, D$_2$O) δ 4.21 (d, J=2.4 Hz, 2H), 3.68-3.74 (m, 6H), 3.16-3.18 (m, 2H), 2.87 (t, J=2.2 Hz, 1H).

Weighing 490 mg of SN38, dissolving in 30 mL of DMF, cooling to 0° C., adding 320 mg of DiPEA and 251 mg of p-nitrophenyl chloroformate, further reacting at the temperature for 0.5 h, reacting at room temperature for 3 h to obtain intermediate 64, adding 320 mg of DiPEA and 269 mg of compound 71, reacting at room temperature overnight while monitoring the reaction well proceeded by TLC, removing DMF by concentration, separating by column chromatography to obtain crude compound 72, dissolving 165 mg of the compound 72 and 117 mg of the compound 32 in 16 mL of THF-H$_2$O, adding 91 mg of anhydrous copper sulfate and 113 mg of sodium ascorbate in sequence, stirring at room temperature overnight, concentrating, and separating by column chromatography to obtain 60 mg of compound 73 with two-step yield of 12.5%.

$^1$H NMR (400 Hz, DMSO-d$_6$) δ 8.31 (s, 1H), 8.18 (d, J=9.2 Hz, 1H), 7.95-8.02 (m, 2H), 7.64 (dd, J=9.2, 2.0 Hz, 1H), 7.33 (s, 1H), 6.52 (s, 1H), 5.53 (d, J=9.2 Hz, 1H), 5.44 (s, 2H), 5.34-5.38 (m, 3H), 5.27 (d, J=4.8 Hz, 1H), 5.14 (d, J=5.6 Hz, 1H), 4.63 (t, J=5.6 Hz, 1H), 4.58 (s, 2H), 3.52-3.78 (m, 8H), 3.36-3.45 (m, 4H), 3.17-3.24 (m, 4H), 1.86-1.90 (m, 2H), 1.30 (t, J=7.4 Hz, 3H), 0.88 (t, J=7.4 Hz, 3H).

Example 12 Synthesis of Compound 74

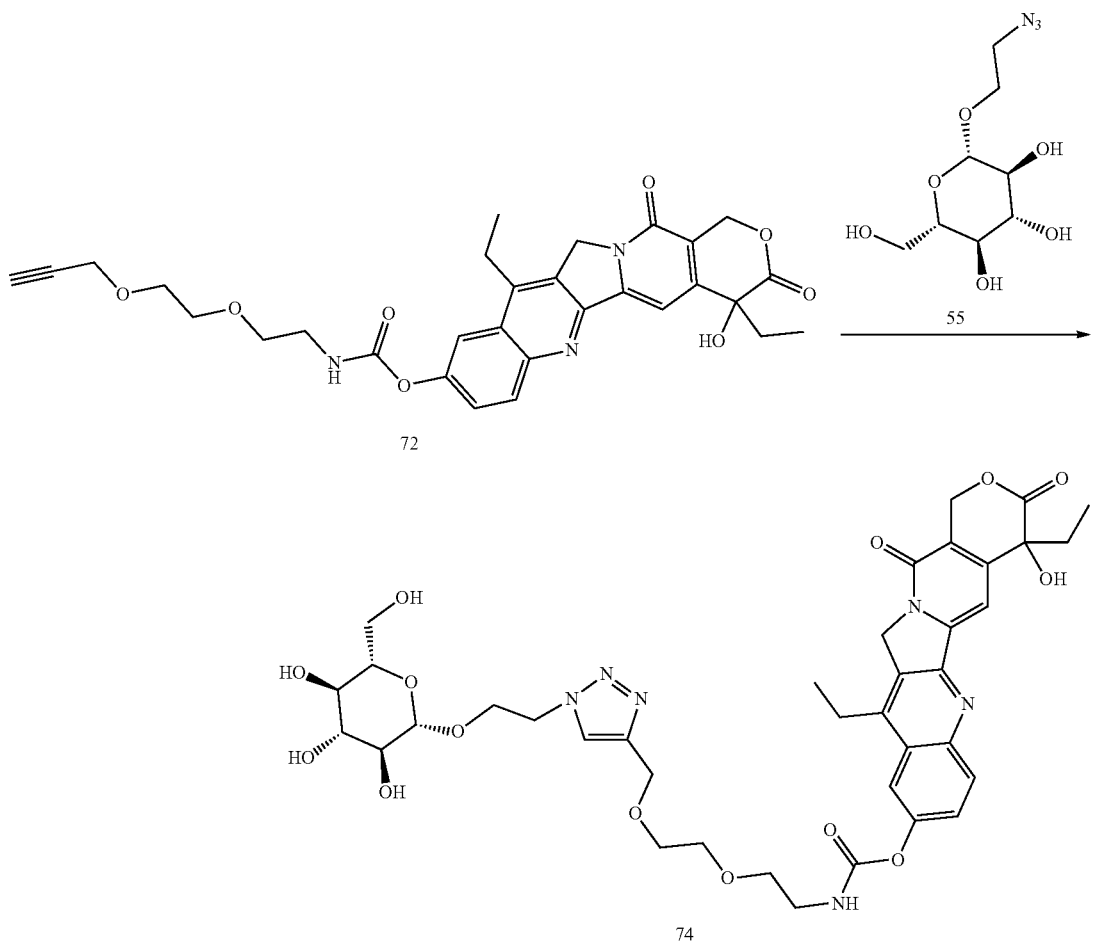

Dissolving 165 mg of the crude compound 72 and 125 mg of the compound 55 in 16 mL of THF-H$_2$O, adding 91 mg of anhydrous copper sulfate and 113 mg of sodium ascorbate in sequence, stirring at room temperature overnight, concentrating, and separating by column chromatography to obtain 50 mg of compound 74 with two-step yield of 9.9%.

$^1$H NMR (400 Hz, DMSO-d$_6$) δ 8.16-8.18 (m, 2H), 8.00 (d, J=5.6 Hz, 1H), 7.95 (s, 1H), 7.63 (d, J=8.8 Hz, 1H), 7.33 (s, 1H), 6.51 (s, 1H), 5.44 (s, 2H), 5.33 (s, 2H), 5.07 (d, J=4.8 Hz, 1H), 4.93 (dd, J=13.2, 4.4 Hz, 2H), 4.49-4.58 (m, 5H), 4.23 (d, J=6.8 Hz, 1H), 4.07-4.09 (m, 1H), 3.89-3.92 (m, 1H), 3.60-3.70 (m, 5H), 3.53 (t, J=6.0 Hz, 2H), 3.39-3.43 (m, 1H), 3.28-3.31 (m, 2H), 3.10-3.20 (m, 4H), 2.96-2.99 (m, 2H), 1.84-1.89 (m, 2H), 1.29 (t, J=7.6 Hz, 3H), 0.89 (t, J=7.2 Hz, 3H).

Example 13 Synthesis of Compound 80 ing the reaction liquid with 1N HCl (100 mL×3), drying organic layer by anhydrous sodium sulfate, filtering, and concentrating to obtain 7 g of compound 76 with yield of 60.3%.

$^1$H NMR (400 Hz, DMSO-d$_6$) δ 6.72 (s, 1H), 4.37 (t, J=9.2 Hz, 1H), 3.36-3.41 (m, 2H), 2.93-2.98 (m, 2H), 1.48-1.55 (m, 2H), 1.37 (s, 9H).

Weighing 3.5 g of the compound 76, dissolving in 60 mL of tetrahydrofuran, adding 1.09 g of tetrabutylammonium iodide, 450 mg of sodium iodide and 2.85 g of 3-bromo-1-propyne, stirring at room temperature, adding 11.2 g of potassium hydroxide in small batches, reacting at room temperature overnight, removing tetrahydrofuran by concentration, adding 30 mL of water, extracting with ethyl acetate (30 mL×3), drying organic layer with anhydrous sodium sulfate, filtering, concentrating, and separating by column chromatography to obtain 2.4 g of compound 77 with yield of 56.3%.

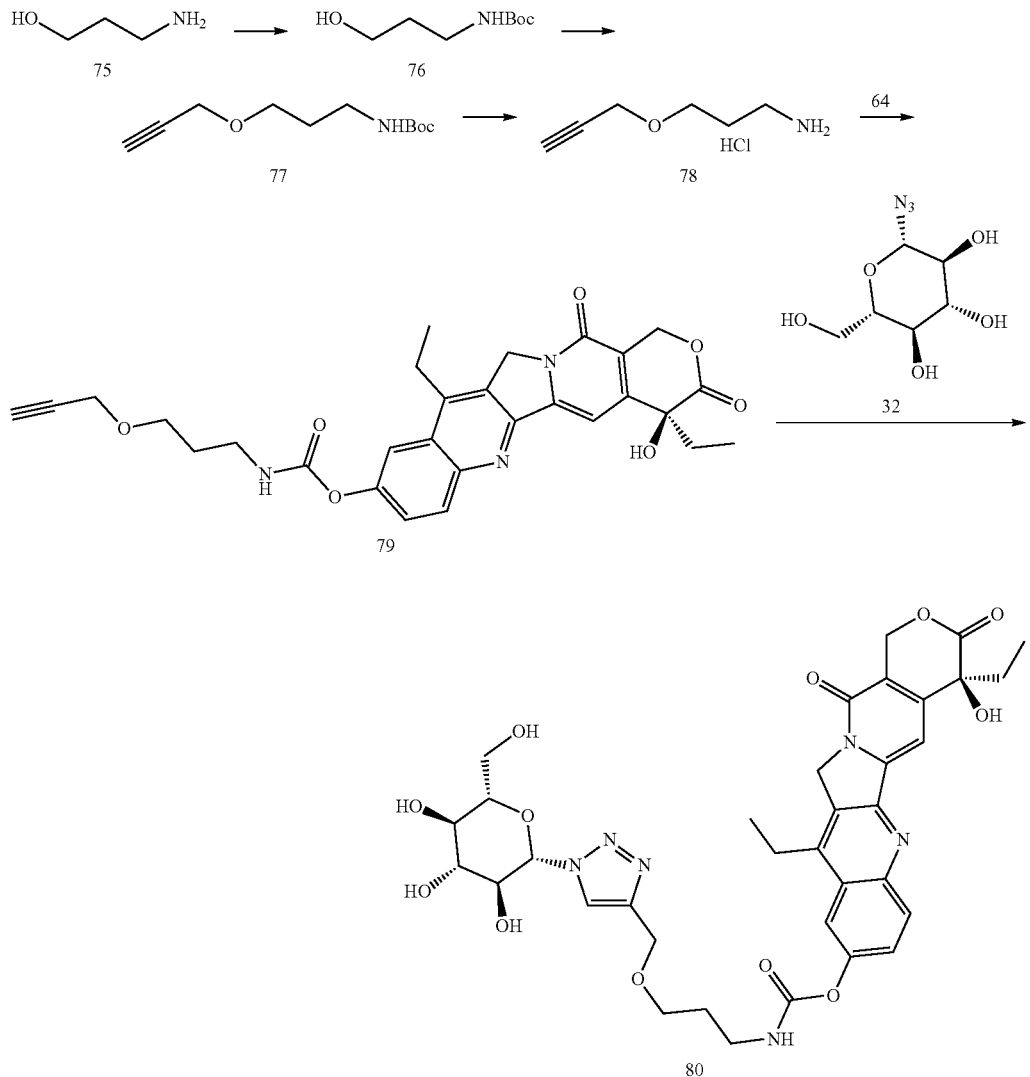

Weighing 5 g of compound 75 and 13.4 g of triethylamine, dissolving in 150 mL of dichloromethane, cooling to 0° C., slowly and dropwise adding 14.5 g of di-tert-butyl dicarbonate, reacting at room temperature overnight, wash- Weighing 1.3 g of the compound 77, dissolving in 20 mL of methanol, adding 20 mL of 3N HCl solution, stirring at room temperature overnight, and concentrating to obtain 620 mg of compound 78 with yield of 68.2%.

Weighing 392 mg of compound SN38, dissolving in 30 mL of DMF, cooling to 0° C., adding 320 mg of DiPEA and 266 mg of p-nitrophenyl chloroformate, further reacting at the temperature for 0.5 h, reacting at room temperature 3 h to obtain the intermediate 64, adding 320 mg of DiPEA and 224 mg of the compound 78, reacting at room temperature overnight while monitoring the reaction well proceeded by TLC, removing DMF by concentration, separating by column chromatography to obtain crude compound 79, dissolving 220 mg of the compound 79 and 214 mg of the compound 32 in 16 mL of THF-H$_2$O, adding 166 mg of anhydrous copper sulfate and 206 mg of sodium ascorbate in sequence, stirring at room temperature overnight, concentrating, and separating by column chromatography to obtain 70 mg of compound 80 with two-step yield of 19.0%.

$^1$H NMR (400 Hz, DMSO-d$_6$) δ 8.30 (s, 1H), 8.16 (d, J=9.2 Hz, 1H), 7.94-7.97 (m, 2H), 7.64 (dd, J=9.2, 2.4 Hz, 1H), 7.32 (s, 1H), 6.51 (s, 1H), 5.53 (d, J=9.2 Hz, 1H), 5.44 (s, 2H), 5.37 (d, J=5.6 Hz, 1H), 5.31 (s, 2H), 5.28 (d, J=4.8 Hz, 1H), 5.15 (d, J=5.6 Hz, 1H), 4.62 (t, J=5.6 Hz, 1H), 4.55 (s, 2H), 3.68-3.79 (m, 2H), 3.55-3.58 (m, 2H), 3.37-3.41 (m, 3H), 3.17-3.27 (m, 5H), 1.77-1.91 (m, 4H), 1.30 (t, J=7.6 Hz, 3H), 0.89 (t, J=7.4 Hz, 3H).

Example 14 Synthesis of Compound 81

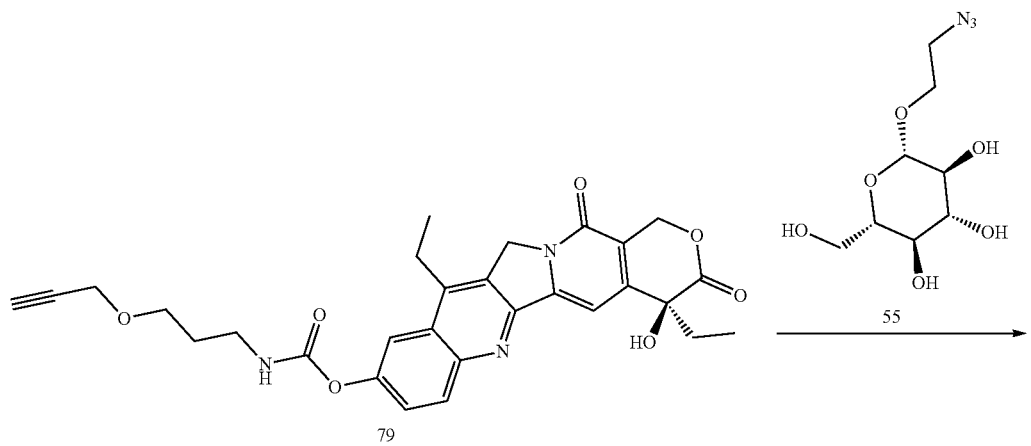

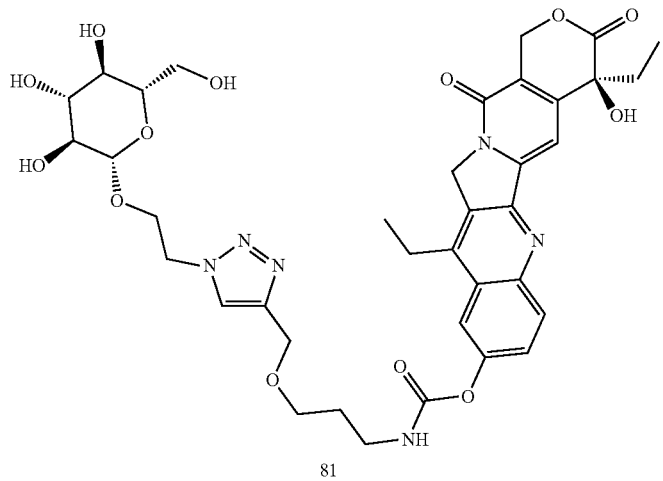

Dissolving 220 mg of the crude compound 79 and 224 mg of the compound 55 in 16 mL of THF-H$_2$O, adding 166 mg of anhydrous copper sulfate and 206 mg of sodium ascorbate in sequence, stirring at room temperature overnight, concentrating, and separating by column chromatography to obtain 100 mg of compound 81 with two-step yield of 25.6%.

$^1$H NMR (400 Hz, DMSO-d$_6$) δ 8.16-8.18 (m, 2H), 7.96-7.99 (m, 2H), 7.65 (dd, J=9.0, 2.2 Hz, 1H), 7.32 (s, 1H), 6.54 (s, 1H), 5.44 (s, 2H), 5.34 (s, 2H), 5.11 (d, J=4.8 Hz, 1H), 4.97 (dd, J=15.2, 4.8 Hz, 2H), 4.52-4.57 (m, 5H), 4.23 (d, J=7.6 Hz, 1H), 4.07-4.12 (m, 1H), 3.89-3.92 (m, 1H), 3.66-3.70 (m, 1H), 3.54 (t, J=6.0 Hz, 2H), 3.40-3.46 (m, 1H), 3.10-3.18 (m, 6H), 2.94-3.06 (m, 2H), 1.84-1.91 (m, 2H), 1.75-1.80 (m, 2H), 1.29 (t, J=7.6 Hz, 3H), 0.88 (t, J=7.2 Hz, 3H).

Example 15 Synthesis of Compound 87

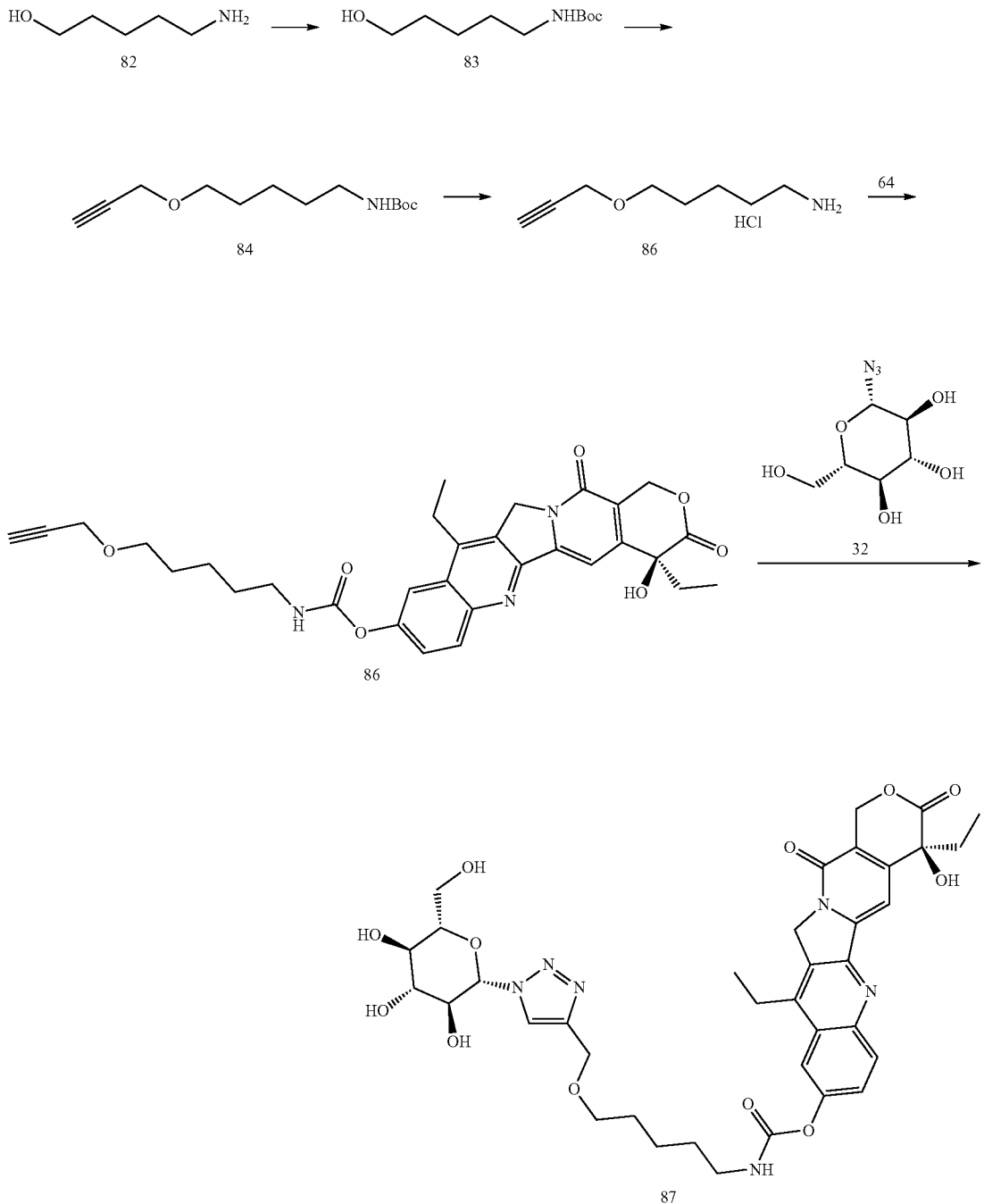

Dissolving 2.09 g of compound 82 and 5.6 mL of triethylamine in 50 mL of dichloromethane, cooling to 0° C., slowly and dropwise adding 4.43 g of di-tert-butyl dicarbonate, reacting at room temperature overnight, washing the reaction liquid with 1N HCl (100 mL×3), drying organic layers with anhydrous sodium sulfate, filtering, and concentrating to obtain 4 g of compound 83 with yield of 97.3%.

$^1$H NMR (400 Hz, CDCl$_3$) δ 4.56 (s, 1H), 3.64 (t, J=6.4 Hz, 2H), 3.10-3.15 (m, 2H), 1.27-1.61 (m, 15H).

Weighing 4 g of the compound 83, dissolving in 60 mL of tetrahydrofuran, adding 812 mg of tetrabutylammonium iodide, 660 mg of sodium iodide and 3.92 g of 3-bromo-1-propyne, stirring at room temperature, adding 2.48 g of potassium hydroxide in small batches, reacting at room temperature overnight, removing tetrahydrofuran by concentration, adding 30 mL of water, extracting with ethyl acetate (30 mL×3), drying organic layers with anhydrous sodium sulfate, filtering, concentrating, and separating by column chromatography to obtain 2.8 g of compounds 84 with yield of 59.1%.

$^1$H NMR (400 Hz, CDCl$_3$) δ 4.54 (s, 1H), 4.13 (d, J=2.4 Hz, 2H), 3.51 (t, J=6.4 Hz, 2H), 3.09-3.14 (m, 2H), 2.42 (t, J=2.4 Hz, 1H), 1.58-1.63 (m, 2H), 1.35-1.54 (m, 13H).

Weighing 2.8 g of the compound 84, dissolving in 40 mL of methanol, adding 40 mL of 3N HCl solution, stirring at room temperature overnight, and concentrating to obtain 1.7 g of compound 85 with yield of 86.7%.

$^1$H NMR (400 Hz, D$_2$O) δ 4.09 (d, J=2.4 Hz, 2H), 3.52 (t, J=6.8 Hz, 2H), 2.89 (t, J=7.6 Hz, 2H), 2.77 (t, J=2.2 Hz, 1H), 1.48-1.58 (m, 4H), 1.24-1.36 (m, 2H).

Weighing 392 mg of compound SN38, dissolving in 30 mL of DMF, cooling to 0° C., adding 320 mg of DiPEA and 266 mg of p-nitrophenyl chloroformate, further reacting at the temperature for 0.5 h, reacting at room temperature for 3 h to obtain the intermediate 64, adding 320 mg of DiPEA and 266 mg of the compound 85, reacting at room temperature overnight while monitoring the reaction well proceeded by TLC, removing DMF by concentration, separating by column chromatography to obtain 400 mg of crude compound 86, dissolving 200 mg of the compound 86 and 200 mg of the compound 32 in 16 mL of THF-H$_2$O, adding 166 mg of anhydrous copper sulfate and 206 mg of sodium ascorbate in sequence, stirring at room temperature overnight, concentrating, and separating by column chromatography to obtain 70 mg of compound 87 with two-step yield of 18.3%.

$^1$H NMR (400 Hz, DMSO-d$_6$) δ 8.29 (s, 1H), 8.17 (d, J=9.2 Hz, 1H), 7.93-7.95 (m, 2H), 7.64 (dd, J=9.0, 2.2 Hz, 1H), 7.33 (s, 1H), 6.51 (s, 1H), 5.52 (d, J=9.2 Hz, 1H), 5.44 (s, 2H), 5.36 (d, J=6.0 Hz, 1H), 5.33 (s, 2H), 5.26 (d, J=4.8 Hz, 1H), 5.13 (d, J=5.6 Hz, 1H), 4.62 (t, J=5.6 Hz, 1H), 4.52 (s, 2H), 3.68-3.78 (m, 2H), 3.36-3.51 (m, 6H), 3.20-3.25 (m, 2H), 3.10-3.15 (m, 2H), 1.85-1.92 (m, 2H), 1.51-1.59 (m, 4H), 1.36-1.42 (m, 2H), 1.30 (t, J=7.6 Hz, 3H), 0.89 (t, J=7.2 Hz, 3H).

Example 16 Synthesis of Compound 88

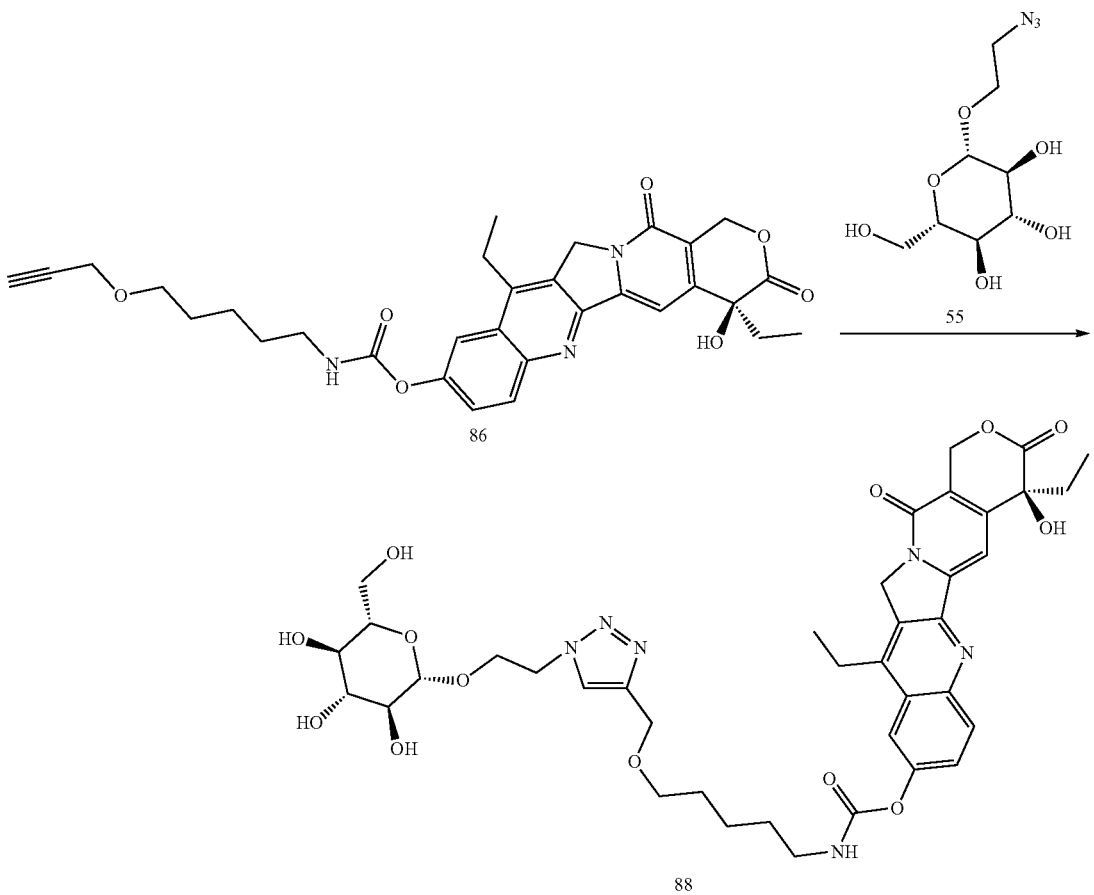

Dissolving 200 mg of the crude compound 86 and 210 mg of the compound 55 in 16 mL of THF-$H_2O$, adding 166 mg of anhydrous copper sulfate and 206 mg of sodium ascorbate in sequence, stirring at room temperature overnight, concentrating, and separating by column chromatography to obtain 70 mg of compound 88 with two-step yield of 17.3%.

$^1$H NMR (400 Hz, DMSO-$d_6$) δ 8.16 (d, J=9.2 Hz, 1H), 8.14 (s, 1H), 7.91-7.94 (m, 2H), 7.63 (dd, J=9.2, 2.4 Hz, 1H), 7.32 (s, 1H), 6.51 (s, 1H), 5.44 (s, 2H), 5.33 (s, 2H), 5.06 (d, J=4.8 Hz, 1H), 4.93 (dd, J=13.2, 5.2 Hz, 2H), 4.56 (t, J=5.2 Hz, 2H), 4.49-4.52 (m, 3H), 4.23 (d, J=8.0 Hz, 1H), 4.07-4.08 (m, 1H), 3.89-3.92 (m, 1H), 3.65-3.67 (m, 1H), 3.42-3.48 (m, 3H), 3.09-3.20 (m, 6H), 2.96-3.06 (m, 2H), 1.86-1.89 (m, 2H), 1.50-1.58 (m, 4H), 1.34-1.38 (m, 2H), 1.29 (t, J=7.6 Hz, 3H), 0.89 (t, J=7.4 Hz, 3H).

Example 17 Solubility Test

The solubility test is carried out by equilibrium method. The solubility of the synthesized compounds in water, normal saline, PBS (pH 7.4) and 0.1% aqueous solution of Tween-80 is determined by ultraviolet-visible spectrophotometry according to the fourth part 0401 of Pharmacopoeia of the People's Republic of China, 2015 edition. An appropriate amount of the compound is weighed and dissolved in 1 mL of methanol solution to prepare a control solution with a certain concentration (C0). The concentration of test solution is calculated according to the following formula: Cx=(Ax/A0)C0, wherein Cx is concentration of test solution, Ax is absorbance of test solution, C0 is concentration of control solution, and A0 is absorbance of control solution. The test results are shown in Table 1.

TABLE 1

Results of Compound Solubility Test

| Compound No. | Solubility in Different Solvents (μg/mL) | | | |
|---|---|---|---|---|
| | Water | Normal Saline (NS) | PBS (pH = 7.4) | 0.1% Tween-80 |
| 37 | 158.9 | 724.9 | 54.4 | 359.5 |
| 42 | 161.5 | 5868.1 | 85.2 | 120.13 |
| 47 | 109.3 | 510.9 | 60.8 | 649.6 |
| 52 | 3046.7 | 445.8 | 85.2 | 320.2 |
| 56 | 635.5 | 1107.3 | 85.2 | 2175.7 |
| 57 | 178.1 | 4294.6 | 360.6 | 6456.4 |
| 58 | 2553.8 | 3593.2 | 1575.8 | 5334.8 |
| 59 | 1483.4 | 853.6 | 984.1 | 1204.2 |
| 66 | 979.1 | 1594.5 | 2875.2 | 1143.5 |
| 67 | 1262.7 | 3348.9 | 2108.4 | 1478.9 |
| 73 | 3583.3 | 1441.4 | 414.3 | 1264.3 |
| 74 | 791.8 | 3954.2 | 564.7 | 2752.2 |
| 80 | 82.5 | 641.8 | 792.5 | 960.7 |
| 81 | 985.2 | 985.2 | 895.4 | 1210.4 |
| 87 | 1047.8 | 893.5 | 910.2 | 1106.6 |
| 88 | 1126.4 | 869.7 | 895.3 | 1347.4 |
| CPT-11 | 6297.9 | 1221.5 | 842.8 | 597.4 |
| SN38 | 7.7 | 7.5 | 17.6 | 77.4 |

According to the results in Table 1, SN38 has very low solubility in water, normal saline, PBS (PH 7.4) and 0.1% aqueous solution of Tween-80. After structural modification, the solubility of the obtained compound is greatly higher than that of SN38, and most of the compounds have solubility of significantly higher than or close to that of CPT-11 in normal saline.

Example 18 Cytotoxicity Test

In order to investigate the antitumor activities of the compounds, a variety of tumor cell lines for test are selected. Cells at logarithmic growth period are inoculated in a 96-well plate overnight, then drugs with a certain gradient concentrations are added, and incubation is carried out in a cell culture chamber (5% $CO_2$, 37° C.) for 72 h. The efficacy evaluation is performed by MTT method to investigate 50% inhibiting concentration value ($IC_{50}$) of the drugs on different cells with CPT-11 as control. The evaluation results are shown in Table 2. According to the results of in vitro experiment, the synthesized SN38 derivatives all show excellent antitumor activities in the tested tumor cell lines, and have growth inhibition effect on most tumors better than that of CPT-11.

TABLE 2

Results of in vitro Cytotoxicity Test

| Tumor Cells | 50% Inhibiting Concentration value ($IC_{50}$) (μM) of Compounds on Tumor Cells | | | | | | | | |
|---|---|---|---|---|---|---|---|---|---|
| | 37 | 42 | 47 | 52 | 56 | 57 | 58 | 59 | 66 |
| SW-80 | 0.014 | 0.167 | 0.274 | 0.167 | 0.112 | 0.164 | 0.254 | 1.213 | 0.216 |
| HT-29 | 1.940 | 13.515 | 0.694 | 0.859 | 9.395 | 1.682 | 5.251 | 1.127 | 5.114 |
| HCT-116 | 2.336 | 3.006 | 0.273 | 0.527 | 0.137 | 1.389 | 1.995 | 1.673 | 0.843 |
| A549 | 13.091 | 5.727 | 2.954 | 11.114 | 4.696 | 20.924 | 3.041 | 8.031 | 5.653 |
| H1975 | 21.062 | 12.774 | 10.752 | 21.771 | 8.250 | 12.142 | 9.345 | 10.527 | 8.458 |
| HepG2 | 2.188 | 0.174 | 2.738 | 8.217 | 10.230 | 5.146 | 0.625 | 2.733 | 1.624 |
| BGC-823 | 1.247 | 0.139 | 0.228 | 0.139 | 0.093 | 0.137 | 0.212 | 1.011 | 0.180 |
| ECA-109 | 1.617 | 11.263 | 0.578 | 0.716 | 7.829 | 1.402 | 4.376 | 0.939 | 4.262 |
| K562 | 1.947 | 2.505 | 0.228 | 0.439 | 0.114 | 1.158 | 1.663 | 1.394 | 0.703 |
| PC3 | 10.909 | 4.773 | 2.462 | 9.262 | 3.913 | 17.437 | 2.534 | 6.693 | 4.711 |
| 143B | 17.552 | 10.645 | 8.960 | 18.143 | 6.875 | 10.118 | 7.788 | 8.773 | 7.048 |
| MDA-MB-231 | 1.823 | 0.145 | 2.282 | 6.848 | 8.525 | 4.288 | 0.521 | 2.278 | 1.353 |
| Hela | 12.709 | 6.872 | 3.545 | 13.337 | 5.635 | 15.109 | 3.649 | 9.637 | 6.784 |
| TPC-1 | 18.274 | 15.329 | 12.902 | 26.125 | 9.900 | 14.570 | 11.214 | 12.632 | 10.150 |
| SKOV-3 | 2.626 | 0.209 | 3.286 | 9.860 | 12.276 | 6.175 | 0.750 | 3.280 | 1.949 |
| PANC-1 | 13.709 | 6.872 | 3.545 | 13.337 | 5.635 | 22.109 | 3.649 | 9.637 | 6.784 |

TABLE 2-continued

| | Results of in vitro Cytotoxicity Test | | | | | | | |
|---|---|---|---|---|---|---|---|---|
| | 50% Inhibiting Concentration value (IC$_{50}$) (μM) of Compounds on Tumor Cells | | | | | | | |
| Tumor Cells | 67 | 73 | 74 | 80 | 81 | 87 | 88 | CPT-11 |
| SW-80 | 0.251 | 0.862 | 2.064 | 1.425 | 0.851 | 1.152 | 0.865 | 7.381 |
| HT-29 | 5.186 | 3.156 | 7.956 | 6.941 | 9.422 | 7.364 | 9.102 | 12.842 |
| HCT-116 | 0.235 | 0.879 | 2.517 | 5.152 | 7.241 | 1.521 | 2.725 | 14.061 |
| A549 | 2.424 | 5.824 | 9.421 | 6.134 | 8.321 | 6.352 | 9.134 | 34.970 |
| H1975 | 6.732 | 7.144 | 6.822 | 10.681 | 9.678 | 5.123 | 6.982 | 29.135 |
| HepG2 | 1.051 | 2.423 | 6.354 | 9.331 | 6.253 | 7.350 | 6.218 | 12.114 |
| BGC-823 | 0.209 | 0.718 | 1.720 | 1.118 | 0.709 | 0.960 | 0.721 | 9.151 |
| ECA-109 | 4.322 | 2.630 | 6.630 | 5.784 | 7.852 | 6.137 | 7.585 | 11.702 |
| K562 | 0.196 | 0.733 | 2.098 | 4.293 | 6.034 | 1.268 | 2.271 | 10.718 |
| PC3 | 2.020 | 4.853 | 7.851 | 5.112 | 6.934 | 5.293 | 7.612 | 25.142 |
| 143B | 5.610 | 5.953 | 5.685 | 8.901 | 8.065 | 4.269 | 5.818 | 20.279 |
| MDA-MB-231 | 0.876 | 2.019 | 5.295 | 7.776 | 5.211 | 6.125 | 5.182 | 14.428 |
| Hela | 2.909 | 6.989 | 11.035 | 7.361 | 9.985 | 7.622 | 10.961 | 11.964 |
| TPC-1 | 8.078 | 8.573 | 8.186 | 12.817 | 11.614 | 6.148 | 8.378 | 24.962 |
| SKOV-3 | 1.261 | 2.908 | 7.625 | 11.197 | 7.504 | 8.820 | 7.462 | 16.537 |
| PANC-1 | 2.909 | 6.989 | 11.305 | 7.361 | 9.985 | 7.622 | 10.961 | 21.964 |

Example 19 Study on In Vivo Antitumor Activity

Combining the results of solubility and in vitro cytotoxicity, in vivo antitumor activities of compounds 58 and 67 are studied, including the following steps:

Feeding 4-5-week Balb/c mice in specified-pathogens free (SPF) environment for one week, subcutaneously inoculating colon cancer cells SW-480 in mice with inoculation density of 1.0×10$^7$ cells in each mouse, when the tumor grows to about 100 mm$^3$, randomly dividing into 4 groups: normal saline control group (control group), irinotecan hydrochloride group (CPT-11 group, 15 mg/kg, i.e. 0.024 mmol/kg), compound 58 group (13.73 mg/kg, i.e. 0.016 mmol/kg) and compound 67 group (12.30 mg/kg, i.e. 0.016 mmol/kg), applying administration manner as dissolving the compounds in normal saline (NS) separately and intravenously injecting once every three days for a total of 7 times, measuring tumor size and volume once every three days until administration is completed, killing the nude mice with their necks broken after test, dissecting the nude mice, and preserving the their vital organs for future use.

Figure 2:
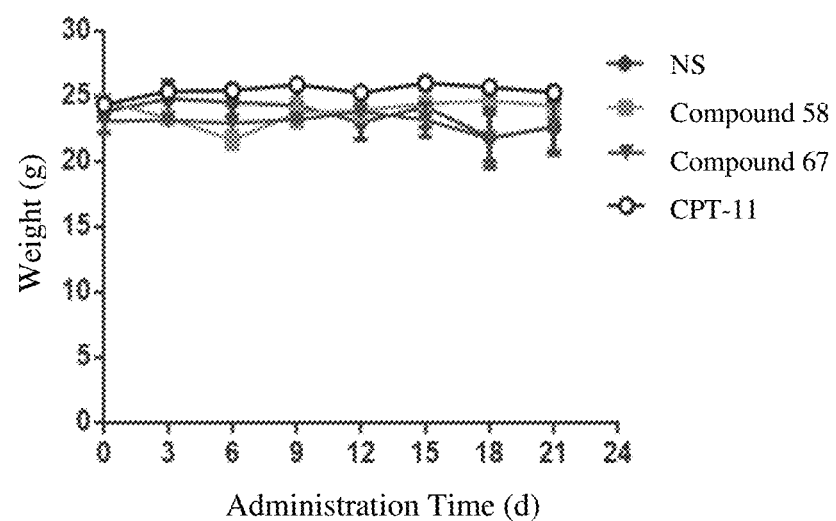
FIG. 2: Nude mouse weight-time change diagram.

Table 3 and Table 4 are mouse tumor volume-time variation data and mouse weight-time variation data, respectively. FIG. 1 and FIG. 2 are mouse tumor volume-time variation diagram and mice eight-time variation diagram, respectively. According to Table 3 and FIG. 1, at a dosage accounting for two-thirds of the molar fraction of CPT-11, compounds 58 and 67 both exhibit significantly higher inhibition rates on colon cancer cell SW-480 than CPT-11. According to Table 4 and FIG. 2, weight loss in mice is not induced at administration dosage, indicating that the compounds have no significant toxicity at administration dosage.

TABLE 3

| Nude Mouse Tumor Volume-Time Variation Data (Average value, n = 6) | | | | |
|---|---|---|---|---|
| | Mouse Tumor Volume (mm$^3$) | | | |
| Time (d) | Normal Saline (NS) | Compound 58 | Compound 67 | CPT-11 |
| 0 | 234.60 | 235.22 | 227.31 | 128.27 |
| 3 | 265.89 | 202.08 | 126.54 | 104.73 |
| 6 | 375.56 | 98.87 | 142.84 | 125.20 |

TABLE 3-continued

| Nude Mouse Tumor Volume-Time Variation Data (Average value, n = 6) | | | | |
|---|---|---|---|---|
| | Mouse Tumor Volume (mm$^3$) | | | |
| Time (d) | Normal Saline (NS) | Compound 58 | Compound 67 | CPT-11 |
| 9 | 499.98 | 118.41 | 104.75 | 222.50 |
| 12 | 1260.73 | 80.63 | 73.72 | 277.50 |
| 15 | 1434.04 | 38.37 | 43.74 | 362.50 |
| 18 | 1458.90 | 40.03 | 12.46 | 477.50 |
| 21 | 1411.61 | 7.16 | 11.38 | 682.50 |

TABLE 4

| Nude Mouse Weight-Time Variation Data | | | | |
|---|---|---|---|---|
| | Mouse Weight (g) | | | |
| Time (d) | Normal Saline (NS) | Compound 58 | Compound 67 | CPT-11 |
| 0 | 23.84 | 23.57 | 23.97 | 24.39 |
| 3 | 24.82 | 23.71 | 23.97 | 25.37 |
| 6 | 24.56 | 24.00 | 23.57 | 25.44 |
| 9 | 24.31 | 24.76 | 23.94 | 25.89 |
| 12 | 23.00 | 24.93 | 23.58 | 25.27 |
| 15 | 24.21 | 24.34 | 24.45 | 26.02 |
| 18 | 21.86 | 24.04 | 24.86 | 25.69 |
| 21 | 22.64 | 24.12 | 25.33 | 25.30 |

In conclusion, the water solubility of SN38 is greatly improved by modification on structure of it. In vivo and in vitro experiment results show that the antitumor activities of the derivatives are better than that of irinotecan hydrochloride.

Example 20 Study on Multi-Dose In Vivo Antitumor Activity

Test Grouping and Treatment Schemes

The successfully inoculated mice are randomly divided into 8 groups with 6 mice in each group: normal saline group (NS), CPT-11 group, compound 58 low-dose group, compound 58 medium-dose group, compound 58 high-dose group, compound 67 low-dose group, compound 67 medium-dose group and compound 67 high-dose group. The drugs are administered through the caudal veins of mice once every 2 days for a total of 7 times.

Administration dosages are as CPT-11 group: 10 mg/kg; the molar ratios of compounds 58 and 67 in high-dose group, medium-dose group and low-dose group to irinotecan of 1/1, 1/2 and 1/4, respectively, namely, the compound 58 high-dose group (H): 13.73 mg/kg, the compound 58 medium-dose group (M): 6.865 mg/kg, the compound 58 low-dose group (L): 3.433 mg/kg, the compound 67 high-dose group (H): 12.30 mg/kg, the compound 67 medium-dose group (M): 6.15 mg/kg, and the compound 67 low-dose group (L): 3.075 mg/kg.

Tumor volume is measured every three days from day 0. The maximum diameter (a) of the tumor is measured first, and then the longest radial line (b) perpendicular to the maximum diameter is measured, using mm as unit. Tumor volume is calculated according to the following formula:

$$V(mm^3) = \frac{a \times b^2}{2}$$

At the end of the treatment cycle, the orbital venous blood of the mice is collected for later blood routine test, the mice are killed by cervical dislocation method, and tumors are removed immediately and photographed. From day 0, the mice in each group are weighed every three days, and the weights are recorded. The weight average value of each group is calculated, and mouse weight variation curve is drawn according to statistical data. At the end of the treatment cycle, tumors are removed from anesthetized mice immediately and weighted, and the tumor weight of each group is recorded. The tumor inhibition rate (%) is calculated according to the following formula:

$$\text{Tumor inhibition rate}(\%) = \left(1 - \frac{\text{average tumor weight of treatment group}}{\text{average tumor weight of negative control group}}\right) \times 100$$

The hearts, livers, spleens, lungs and kidneys of the mice are then removed for later H&E staining of organs and immunohistochemistry of tumor tissues. Tumor volume growth variation curves are drawn with time as x-coordinate and tumor volume as y-coordinate. Mouse weight variation curves are drawn with time as x-coordinate and mouse weight as y-coordinate. The tumor volume growth variation and the mouse weight variation are shown in Table 5 and Table 6. The tumor volume growth variation curves and the mouse weight variation curves are shown in FIGS. 3-5.

Figure 3:
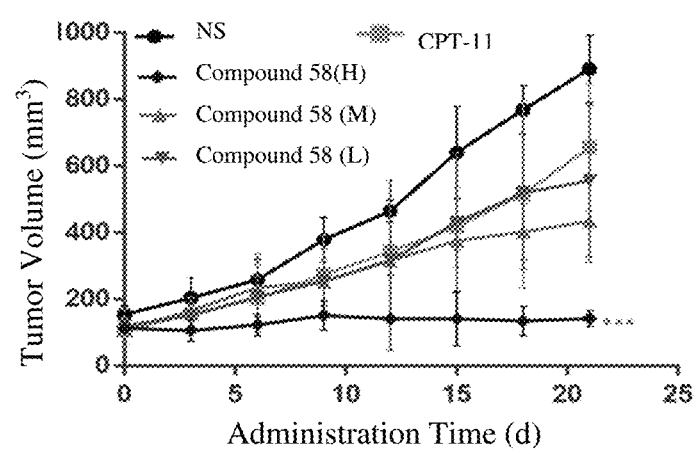
FIG. 3: Nude mouse tumor volume-time variation diagram of compound 58 in study of in vivo antitumor activity of multi-dose compound.
Figure 4:
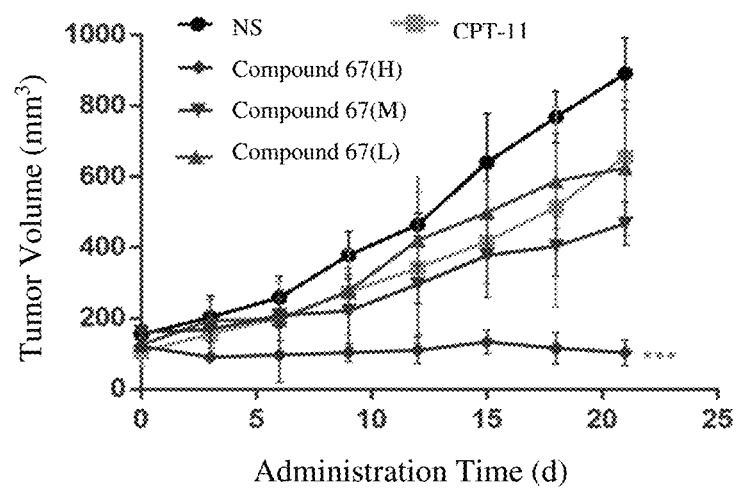
FIG. 4: Nude mouse tumor volume-time variation diagram of compound 67 in study of in vivo antitumor activity of multi-dose compound.
Figure 5:
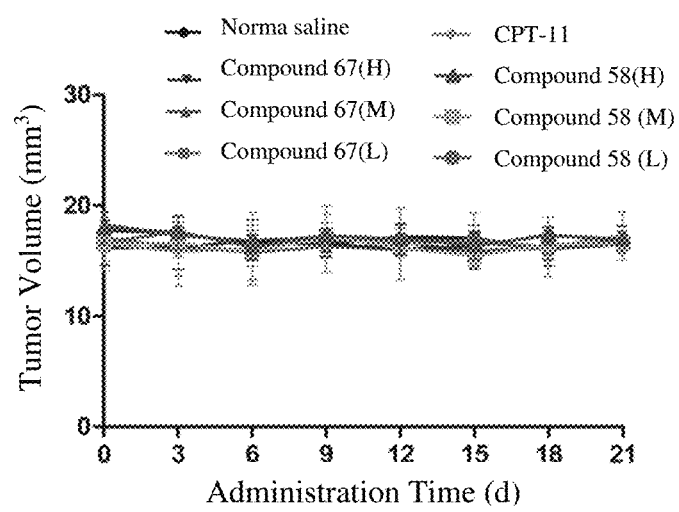
FIG. 5: Weight-time change diagram in study of in vivo antitumor activity of multi-dose compound.

According to Table 5 and the tumor volume growth curves in FIG. 3 and FIG. 4, compounds 58 and 67 both show dose-dependent tolerance for tumor inhibition, and statistical differences ($p<0.05$) are present between the treatment groups and the control group after last administration. The tumor inhibition effects of the high-dose groups of compounds 58 and 67 at the same dosage (10 mg/kg) are better than that of positive control group CPT-11 ($p<0.001$), wherein the tumor volume of the compound 58 high-dose group has the slowest increase, and has significant difference ($p<0.001$) from those of other groups after last administration, indicating that this preparation group has the best antitumor drug effect. According to Table 6 and FIG. 5, the drugs in each dose group have no significant influence on mouse weight, indicating that the compounds have high safety.

TABLE 5

Tumor Volume-Time Variation Data of Study on Multi-Dose in vivo Antitumor Activity of Compounds 58 and 67

| | Mouse Tumor Volume (mm³) | | | | | | | |
| --- | --- | --- | --- | --- | --- | --- | --- | --- |
| Time (d) | Normal Saline | CPT-11 | Compound 58 (L) | Compound 58 (H) | Compound 58 (M) | Compound 67 (L) | Compound 67 (M) | Compound 67 (H) |
| 0 | 154.71 | 105.27 | 110.67 | 120.63 | 113.01 | 125.58 | 161.01 | 121.62 |
| 3 | 204.01 | 156.18 | 164.30 | 151.62 | 106.19 | 194.43 | 168.50 | 91.15 |
| 6 | 258.38 | 202.00 | 235.34 | 206.78 | 122.56 | 197.42 | 208.68 | 96.67 |
| 9 | 378.53 | 273.78 | 252.37 | 254.08 | 151.19 | 278.06 | 220.90 | 103.36 |
| 12 | 464.17 | 342.95 | 316.07 | 317.44 | 141.38 | 420.38 | 295.90 | 110.74 |
| 15 | 640.09 | 417.12 | 375.47 | 430.78 | 141.13 | 498.90 | 378.20 | 133.88 |
| 18 | 769.08 | 580.03 | 401.94 | 519.79 | 134.18 | 587.60 | 404.02 | 116.64 |
| 21 | 891.53 | 656.60 | 433.61 | 555.67 | 142.06 | 624.45 | 394.44 | 103.48 |

TABLE 6

Weight-Time Variation Data of Study on Multi-Dose Compound in vivo Antitumor Activity

| | Mouse Weight (g) | | | | | | | |
| --- | --- | --- | --- | --- | --- | --- | --- | --- |
| Time (d) | Normal Saline (NS) | CPT-11 | Compound 58 (L) | Compound 58 (H) | Compound 58 (M) | Compound 67 (L) | Compound 67 (M) | Compound 67 (H) |
| 0 | 18.21 | 16.53 | 17.94 | 16.69 | 16.55 | 16.18 | 18.28 | 17.04 |
| 3 | 18.21 | 15.87 | 16.34 | 17.60 | 16.61 | 16.28 | 17.29 | 16.15 |
| 6 | 18.21 | 16.10 | 16.36 | 16.26 | 15.81 | 15.76 | 16.82 | 16.88 |
| 9 | 18.21 | 16.96 | 17.00 | 17.28 | 17.23 | 16.28 | 17.18 | 16.57 |
| 12 | 18.21 | 16.53 | 16.96 | 16.88 | 16.17 | 16.03 | 16.74 | 16.06 |
| 15 | 18.21 | 16.86 | 16.41 | 16.61 | 15.46 | 16.04 | 15.82 | 16.32 |

TABLE 6-continued

Weight-Time Variation Data of Study on Multi-Dose Compound in vivo Antitumor Activity

| Time (d) | Normal Saline (NS) | CPT-11 | Compound 58 (L) | Compound 58 (H) | Compound 58 (M) | Compound 67 (L) | Compound 67 (M) | Compound 67 (H) |
|---|---|---|---|---|---|---|---|---|
| | | | | Mouse Weight (g) | | | | |
| 18 | 18.21 | 16.27 | 17.28 | 16.06 | 16.47 | 16.17 | 16.27 | 17.36 |
| 21 | 18.21 | 17.28 | 16.97 | 16.50 | 16.65 | 16.48 | 16.84 | 16.78 |

What is claimed is:

1. A camptothecin derivative, wherein: the camptothecin derivative has the structure shown as Formula II:

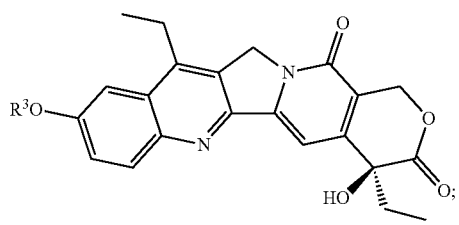

Formula II $R^3$ represents

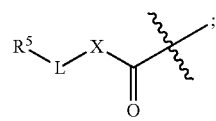

X represents N or O;
L represents

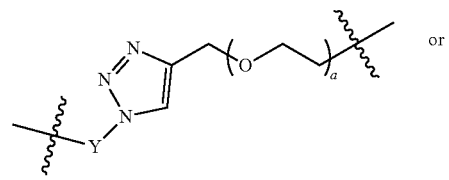
or
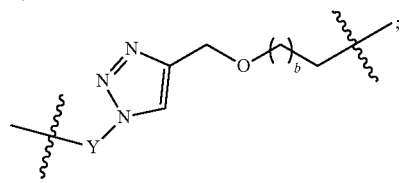
;

Y is

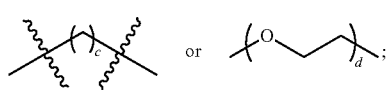 or 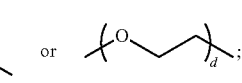;

a is an integer of 1-20;
b is an integer of 1-20;
c is an integer of 0-20;
d is an integer of 0-20; and
$R^5$ is selected from monoglycosyl residue.

2. The camptothecin derivative in claim 1, wherein $R^5$ is selected from one of monoglycosyl residues shown as Formulas 5-28:

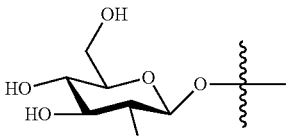
5

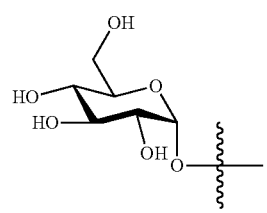
6

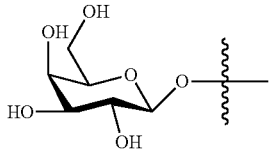
7

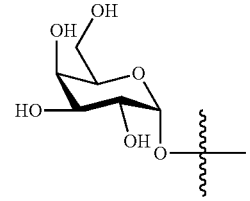
8

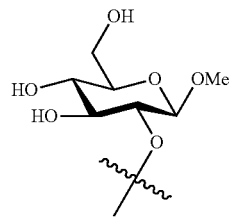
9

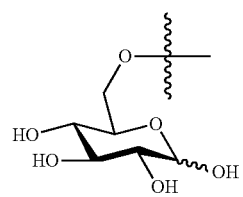
10

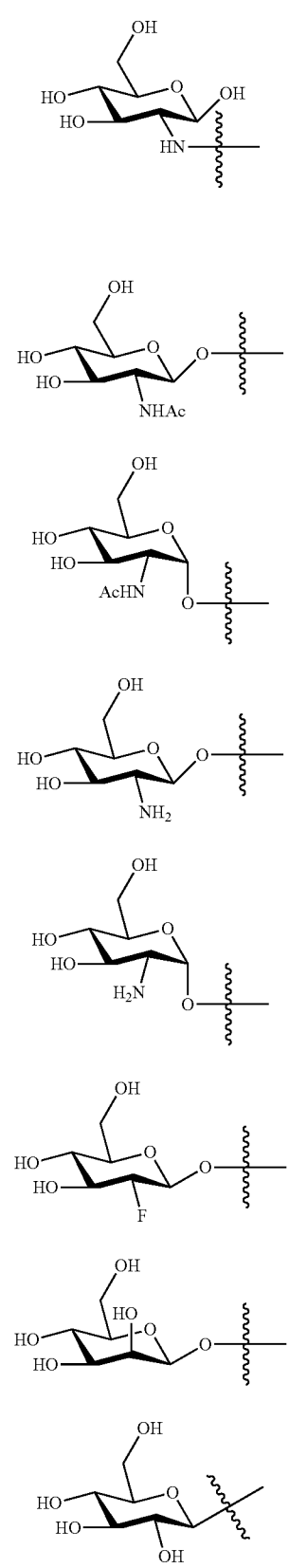
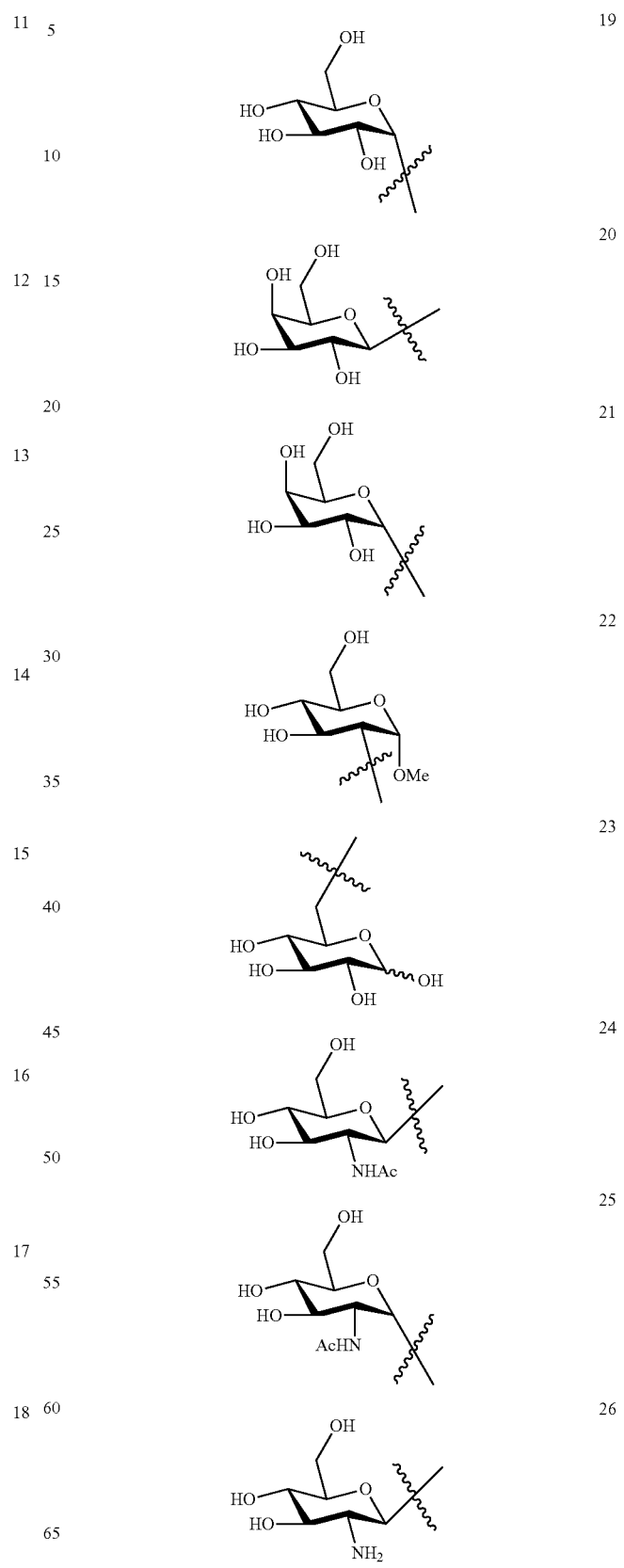

27
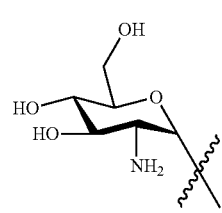
28
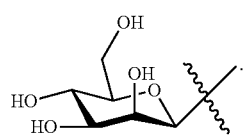
3. The camptothecin derivative in claim 2, wherein $R^5$ is selected from one of monoglycosyl residues shown as Formulas 5, 6, 18 and 19:
5
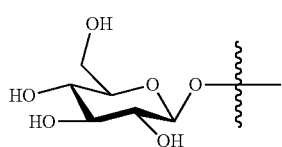
6
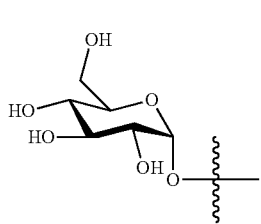
18
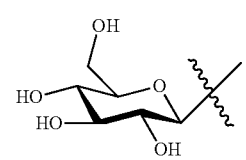
19
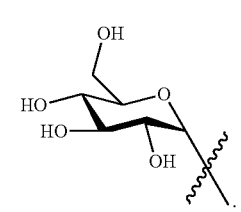
4. The camptothecin derivative in claim 1, wherein the camptothecin derivative is one of the following compounds:
37
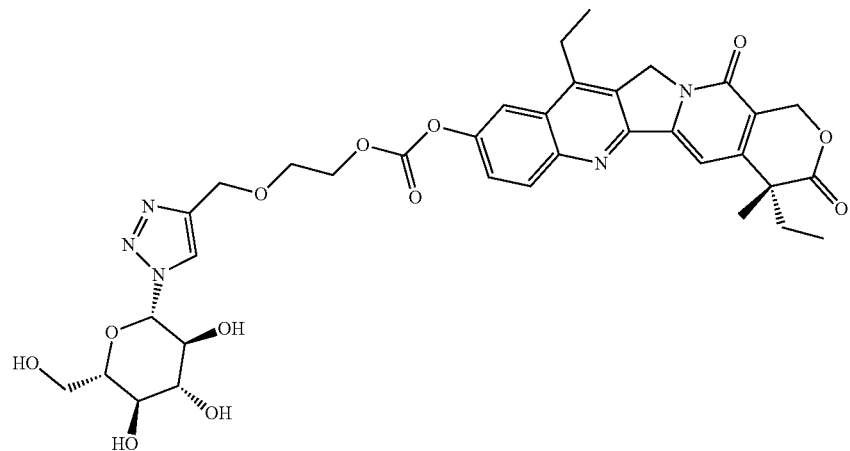
42
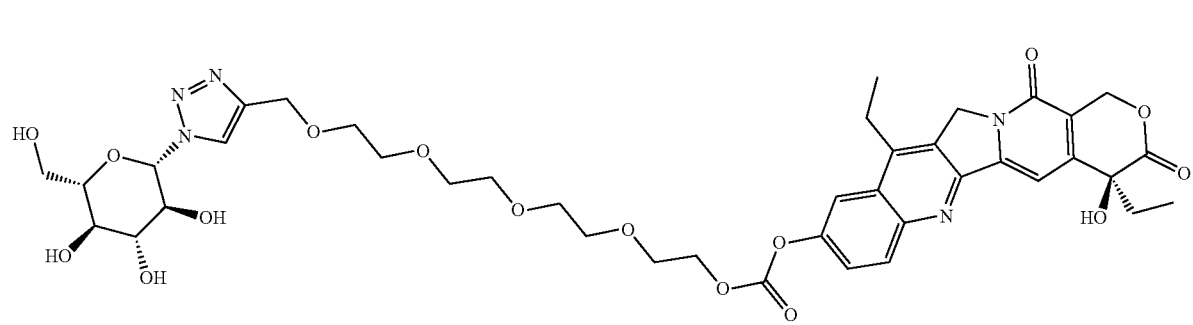

-continued
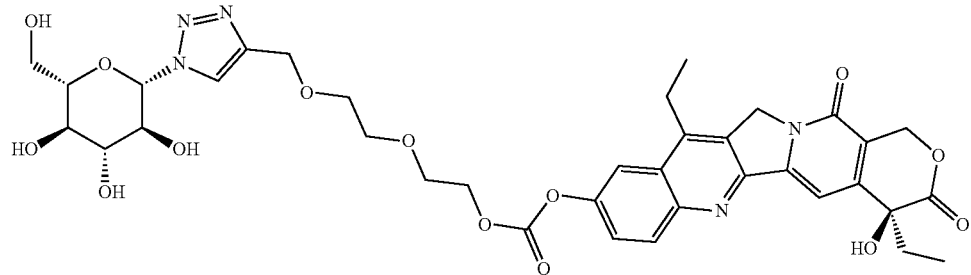
47
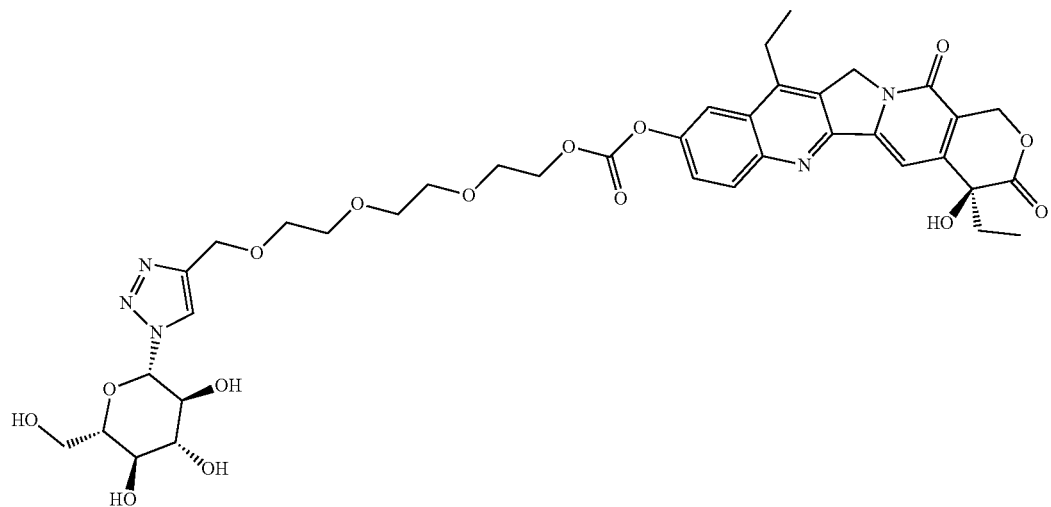
52
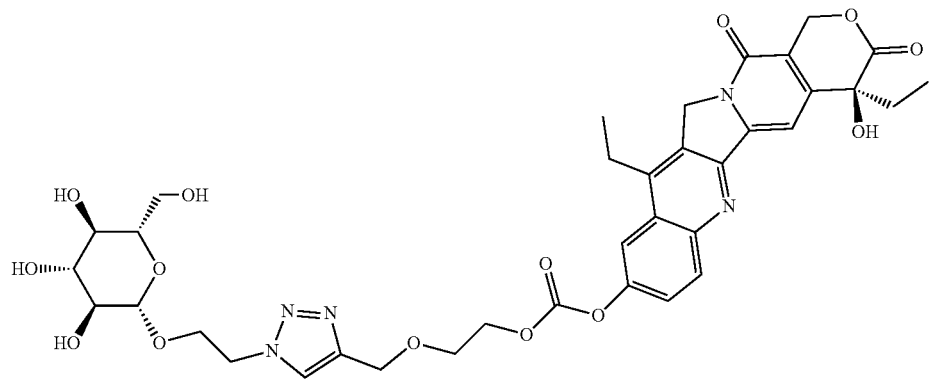
56
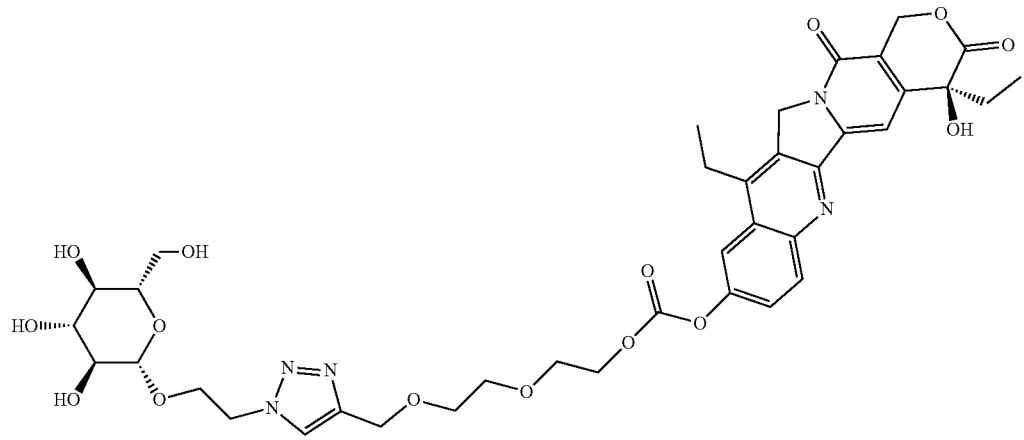
57

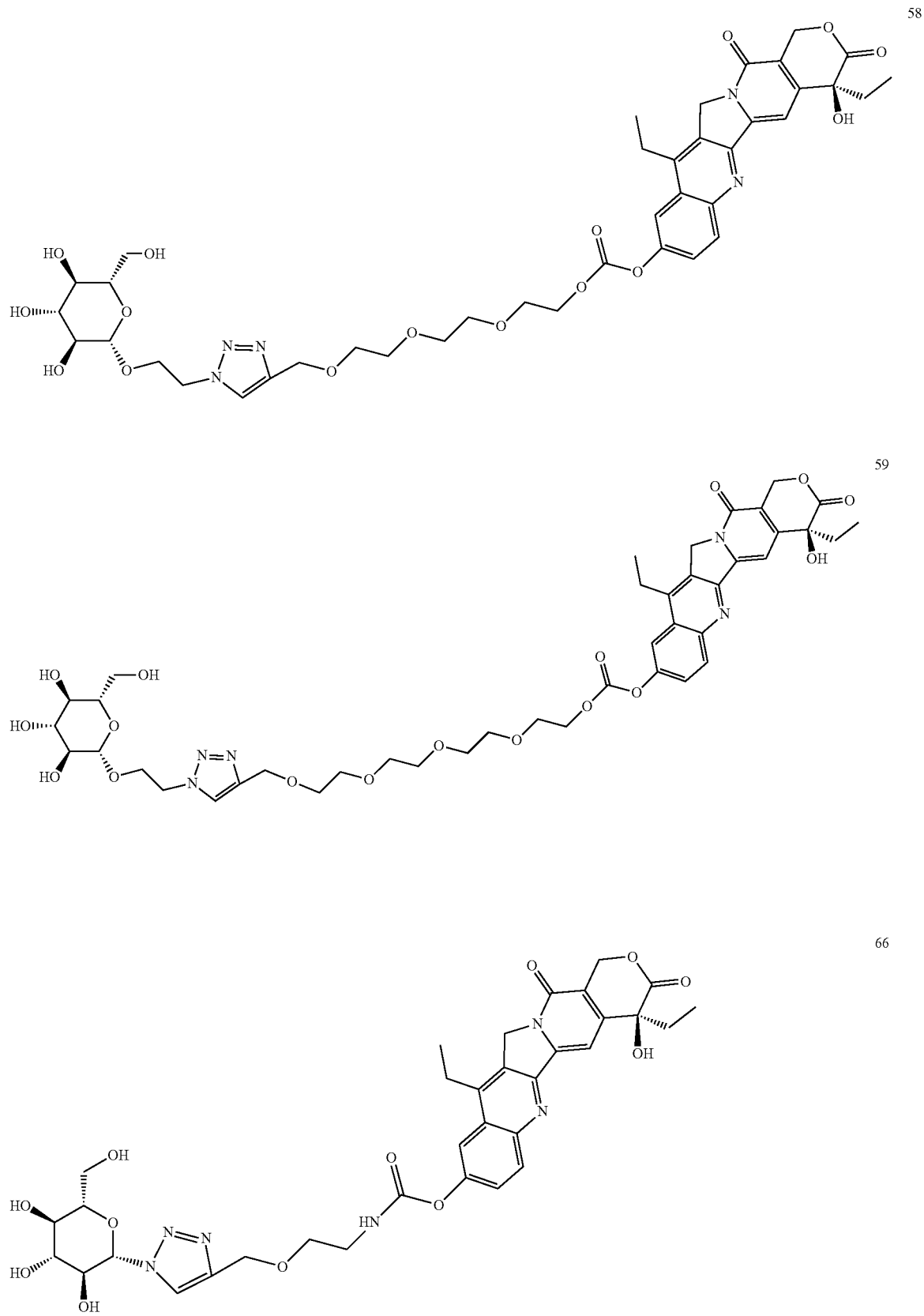

-continued
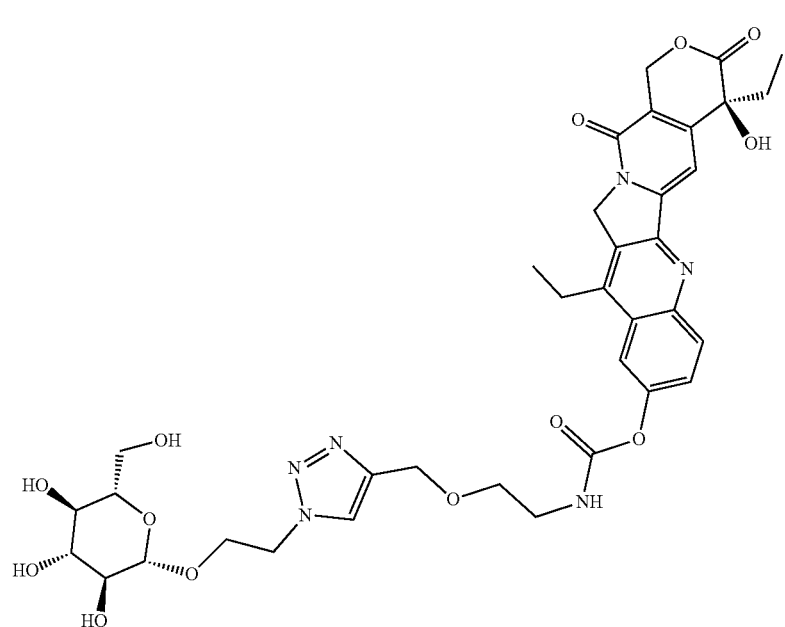
67
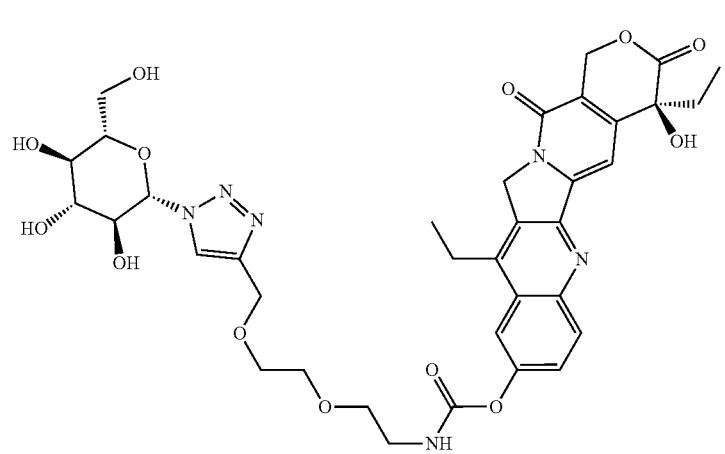
73
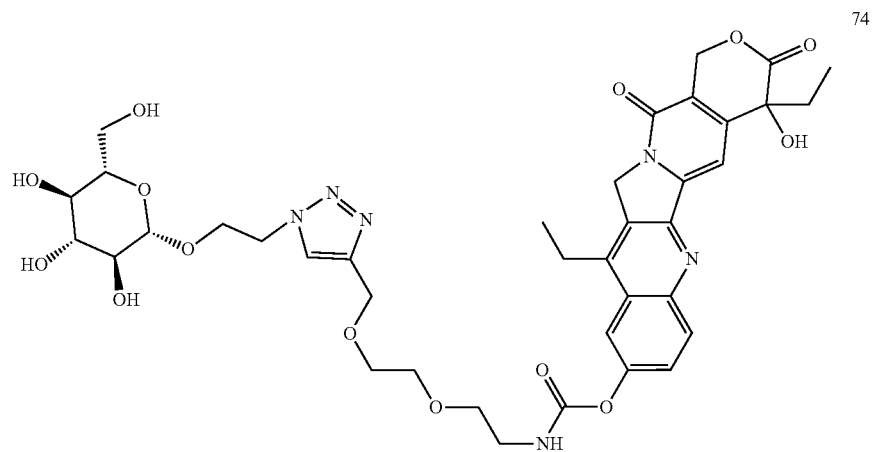
74

80
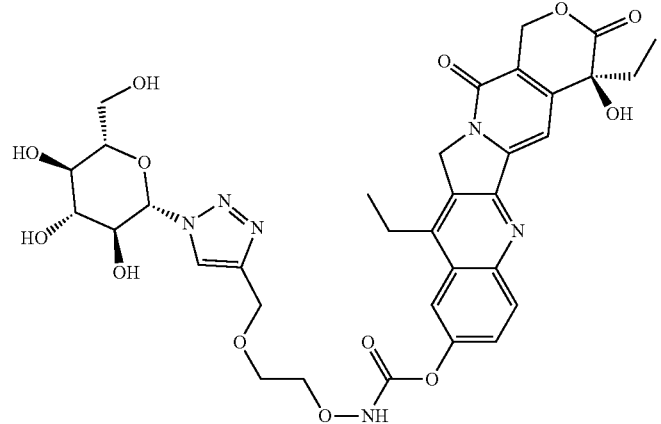
81
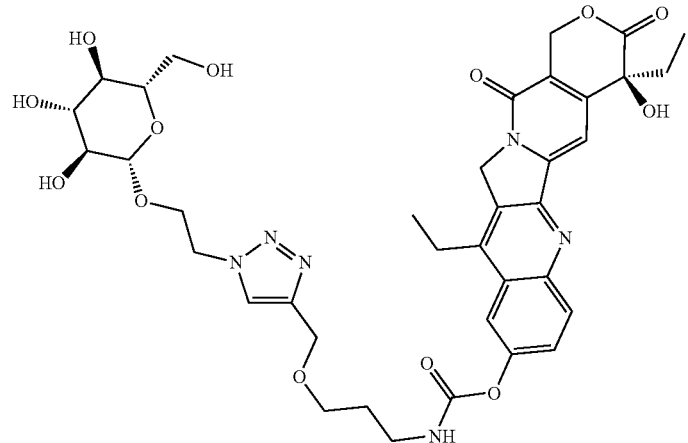
87
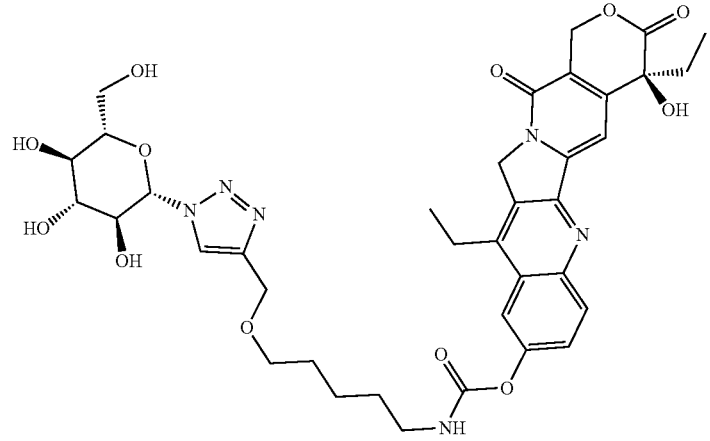

-continued

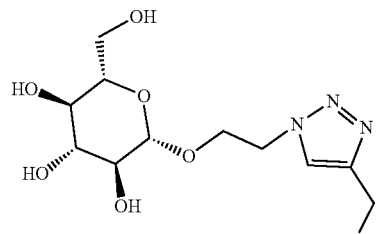 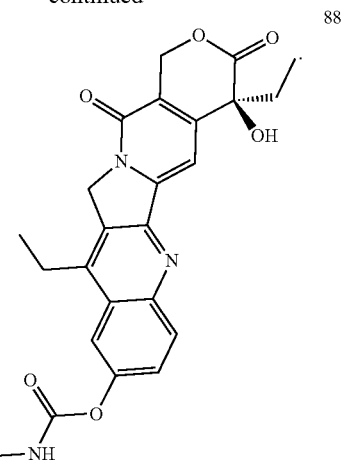

88

5. The camptothecin derivative in claim 1, wherein:
Y is

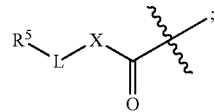

and
d is an integer of 0-20.

6. The camptothecin derivative in claim)d wherein d is an integer of 0-1.

7. The camptothecin derivative in claim 1, wherein:
a is 1; and
b is an integer of 1-4.

8. A method for synthesizing the camptothecin derivative in claim 1, comprising the steps of:
1) synthesizing azide compound of Formula 32 by chemical reaction;
2) synthesizing terminated alkyne by chemical reaction; and
3) dissolving the azide compound of Formula 32 and the terminated alkyne in THF-H$_2$O, adding anhydrous copper sulfate and sodium ascorbate in sequence for click reaction, stirring at room temperature overnight, concentrating, and separating by column chromatography to obtain the camptothecin derivative of Formula II, wherein:

the azide compound of Formula 32 is

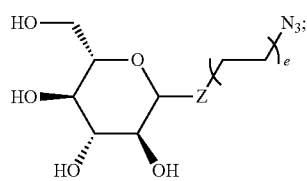

Z is none or O;
e is 0-20;

the camptothecin derivative of Formula II is

Formula II

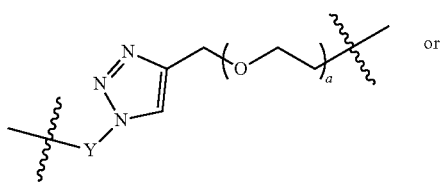

$R^3$ represents

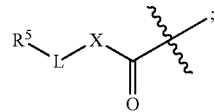

X represents N or O;
L represents

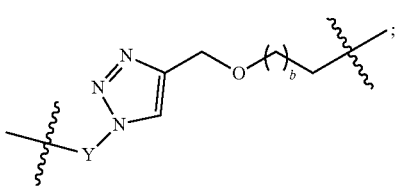

Y is
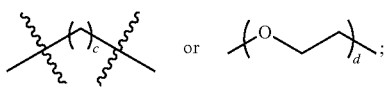
a is an integer of 1-20;
b is an integer of 1-20;
c is an integer of 0-20;
d is an integer of 0-20; and
$R^5$ is selected from monoglycosyl residue.
9. The method in claim 8, wherein $R^5$ has the structure shown as one of Formulas 5-28:
5
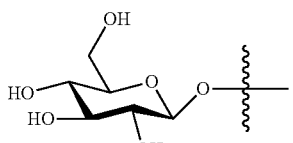
6
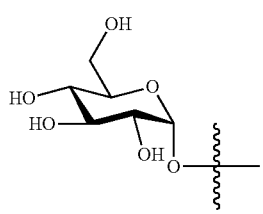
7
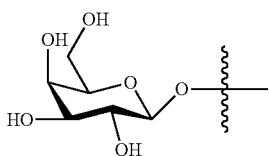
8
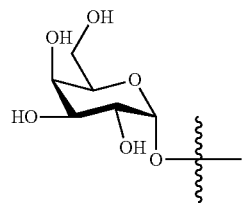
9
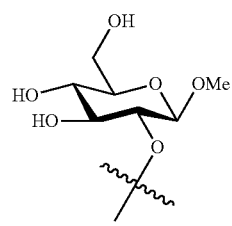
10
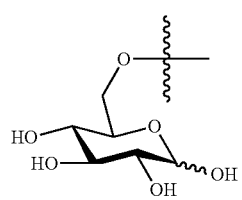
11
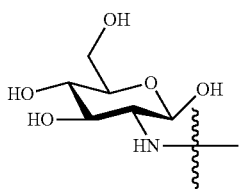
12
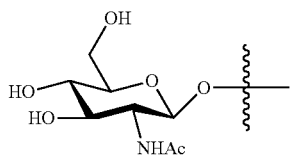
13
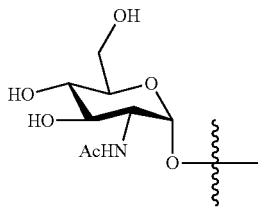
14
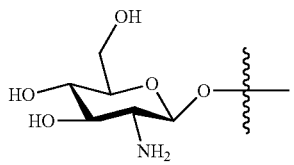
15
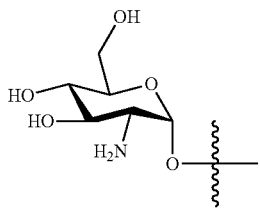
16
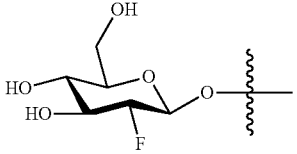
17
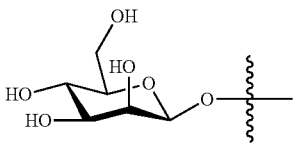
18
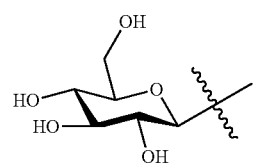

-continued
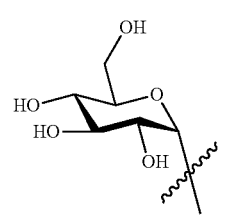
19
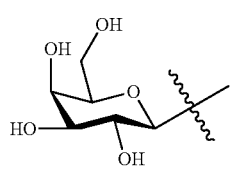
20
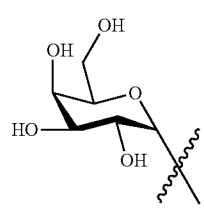
21
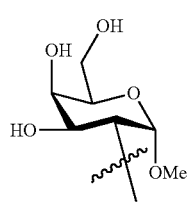
22
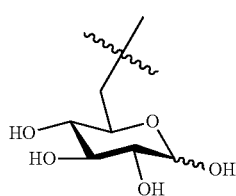
23
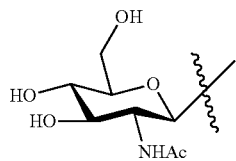
24
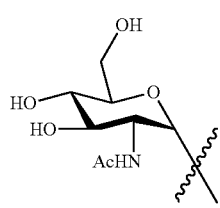
25
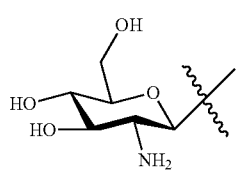
26
-continued
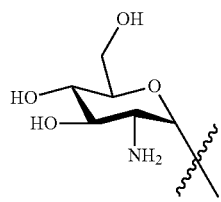
27
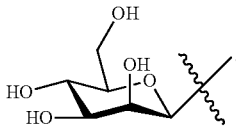
28
10. The method in claim 8, wherein $R^5$ is selected from one of monoglycosyl residues shown as Formulas 5, 6, 18 and 19:
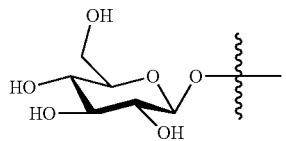
5
6
18
19
11. The method in claim 8, wherein:
a is 1; and
b is an integer of 1-4.
12. The method in claim 8, wherein:
Y is
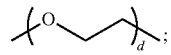
and
d is an integer of 0-20.
13. The method in claim 12, wherein d is an integer of 0-1.
* * * * *